(12) United States Patent
Ho et al.

(10) Patent No.: US 8,692,017 B2
(45) Date of Patent: Apr. 8, 2014

(54) CARBON LINKED MODULATORS OF GAMMA-SECRETASE

(75) Inventors: Chih Yung Ho, Lansdale, PA (US); Yan Zhang, Fort Washington, PA (US); Svenja Burckhardt, Newmarket (GB); Alison Jones, Cambridge (GB)

(73) Assignees: Janssen Pharmaceutica, N.V., Beerse (BE); Cellzone Limited, Cambridge (GB)

( * ) Notice: Subject to any disclaimer, the term of this patent is extended or adjusted under 35 U.S.C. 154(b) by 950 days.

(21) Appl. No.: 12/253,264

(22) Filed: Oct. 17, 2008

(65) Prior Publication Data

US 2009/0105288 A1   Apr. 23, 2009

Related U.S. Application Data

(60) Provisional application No. 60/981,209, filed on Oct. 19, 2007.

(51) Int. Cl.
C07C 63/33 (2006.01)
A01N 43/40 (2006.01)
A61K 31/435 (2006.01)

(52) U.S. Cl.
USPC .......................................... 562/491; 514/277

(58) Field of Classification Search
None
See application file for complete search history.

(56) References Cited

U.S. PATENT DOCUMENTS

| | | | |
|---|---|---|---|
| 3,876,636 A | 4/1975 | Fauran et al. | |
| 4,013,768 A | 3/1977 | Fauran et al. | |
| 4,252,951 A * | 2/1981 | Jackson et al. | 540/220 |
| 5,391,817 A * | 2/1995 | Springer et al. | 562/469 |
| 5,877,399 A | 3/1999 | Hsiao et al. | |
| 7,825,160 B2 | 11/2010 | Wilson et al. | |
| 7,897,643 B2 | 3/2011 | Ho | |
| 7,951,843 B2 | 5/2011 | Ho | |
| 7,968,725 B2 | 6/2011 | Lu | |
| 2002/0128319 A1 | 9/2002 | Koo et al. | |
| 2008/0300261 A1* | 12/2008 | Blurton et al. | 514/255.03 |
| 2009/0105275 A1 | 4/2009 | Ho | |
| 2009/0105300 A1 | 4/2009 | Ho | |
| 2009/0306392 A1 | 4/2009 | Ho | |

FOREIGN PATENT DOCUMENTS

| | | |
|---|---|---|
| CN | 101903347 | 12/2010 |
| EP | 1650183 A1 | 4/2004 |
| EP | 1650183 | 4/2006 |
| EP | 2212287 | 8/2010 |
| EP | 2215043 | 8/2010 |
| WO | WO 01/78721 A1 | 10/2001 |
| WO | WO 03/008635 A2 | 1/2003 |
| WO | WO 2006/004555 | 1/2006 |
| WO | WO 2006/005554 | 1/2006 |
| WO | WO 2006/008558 | 1/2006 |
| WO | WO 2006/008558 A1 | 1/2006 |
| WO | WO 2006/045554 A1 | 5/2006 |
| WO | WO 2007/124351 | 11/2007 |
| WO | WO 2007/124394 | 11/2007 |
| WO | WO 2007/146838 | 12/2007 |
| WO | WO 2009/052126 | 4/2009 |
| WO | WO 2009/052334 | 4/2009 |

OTHER PUBLICATIONS

Silverman (The Organic Chemistry of Drug Design and Drug Action, 1992, Academic Press Inc.).*
Braga et al., "Making crystals from crystals: a green route to crystal engineering and polymorphism" ChemComm 2005, 3635- 3645.*
Vippagunta et. al., Advanced Drug Del. Rev., 48, pp. 3-26, (2001).*
Buchwald, H., et al. "Long-Term, Continuous Intravenous Heparin Administration by an Implantable Infusion Pump in Ambulatory Patients with Recurrent Venous Thrombosis", Surgery 88, p. 507 (1980).
During, M., et al. "Controlled Release of Dopamine from a Polymeric Brain Implant: In Vivo Characterization", Ann. Neurol. 25, p. 351 (1989).
Eriksen, J., et al. "NSAIDs and Enanatiomers of Flurbiprofen Target Gamma-Secretase and Lower A-beta-42 in vivo", Journal of Clinical Investigation, New York, NY US vol. 112, No. 3, (2003), XP002311406.
Frautschy, S., et al. "Microglial Response to Amyloid Plaques in APPsw Transgenic Mice", Am. J. of Pathology, VI. 52, No. 1 p. 307 (1998).
Goodson, J., "Medical Applications of Controlled Release", vol. I, Chapter 6, pp. 115 (Table of Contents) (1984).
Howard, M., et al. "Acute Subdural Hematomas: An Age-Dependent Clinical Entity", J. Neurosurgery, vol. 71, p. 858 (1989).
Hsiao, K., et al. "Correlative Memory Deficits, Aβ Elevation and Amyloid Plaques in Transgenic Mice", Science 274, p. 99 (1996).
Ida, N., et al. "Analysis of Heterogeneous βA4 Peptides in Human Cerebrospinal Fluid and Blood by a Newly Developed Sensitive Western Blot Assay", J. Biol. Chem. 271, p. 22908 (1996).

(Continued)

*Primary Examiner* — Johann R Richter
*Assistant Examiner* — Jennifer C Sawyer
(74) *Attorney, Agent, or Firm* — Baker & Hostetler LLP

(57) ABSTRACT

The present invention relates to compounds of Formula I as shown below, wherein the definitions of A, X, $R^1$, $R^3$, $R^4$, $R^5$, $R^6$, $R^7$, $R^8$, and $R^9$ are provided in the specification. Compounds of Formula I are useful for the treatment of diseases associated with γ-secretase activity, including Alzheimer's disease.

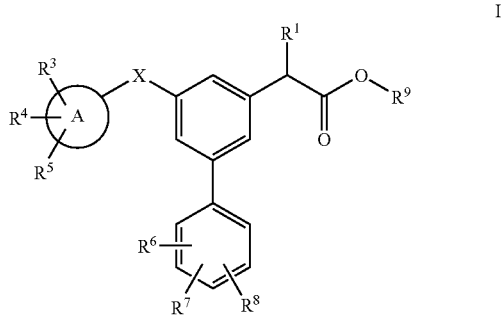

10 Claims, No Drawings

(56) References Cited

OTHER PUBLICATIONS

Irizarry, M., et al. "APP$_{sw}$Transgenic Mice Develop Age-Related Aβ Deposits and Neuropil Abnormalities, but no Neuronal Loss in CA1", J. Of Neuropathology and Experimental Neurology, vol. 56(9), p. 965 (1997).
Jensen, M., et al. "Quantification of Alzheimer Amyloid Peptides Ending at Residues 40 and 42 by Novel ELISA Systems", Mol. Med. 6 p. 291 (2000).
Kawarabayahsi, T., et al. "Age-Dependent Changes in Brain, CSF, and Plasma Amyloid βProtein in the Tg2576 Transgenic Mouse Model of Alzheimer's Disease", J. Neurosci. 21 p. 372 (2001).
Langer, R., "New Methods of Drug Delivery", Science 249, p. 1527 (1990).
Langer and Peppas "Chemical and Physical Structure of Polymers as Carriers for Controlled Release of Bioactive Agents: A Review", Macromol. Chem. Phys. C23(1), 61-126 (1983) (Article Listed As Ranger and Pappas).
Larner, A., "Secretases as Therapeutic Targets in Alzheimer's Disease: Patents 2000-2004", Exp. Opinion Ther. Patents 14, p. 1403 (2004).
Lehman, J., et al. "Alterations in β-Amyloid Production and Deposition in Brain Regions of Two Transgenic Models", Neurobiol. Aging 24, p. 645 (2003).
Levy, R., et al. "Inhibition of Calcification of Bioprosthetic Heart Valves by Local Controlled Release Diphosphonate", Science 228, p. 190 (1985).
Lim, G., et al. Ibuprofen Effects on Alzheimer Pathology and Open Field Activity in APPsw Transgenic Mice, Neuroibol. Aging 22, p. 645 (2001).
Lim, G., et al. Ibuprofen Suppresses Plaque Pathology and Open Field Activity in APPsw Transgenic Mice, Journal of Neuroscience, vol. 20(15), p. 5709 (2000).
Marjaux, E., et al. "γ-Secretase Inhibitors: Still in the Running as Alzheimer's Therapeutics", Drug Discovery Today: Therapeutics Strategies 1, p. 1 (2004).
Morihara, T., et al. "Selective Inhibition of Aβ42 Production b NSAID R- Enantiomer", J., Neurochem. 83, p. 1009 (2002).
Myers, A., et al. "Use of Pseudo Ephedrine as a Practical Chiral Auxiliary for Asymmetric Synthesis", Journal of American Chemical Society, 116 (20), p. 9361 (1994).
Peretto, D., et al. "Synthesis and Biological Activity of Fluriprofen Analogues as Selective Inhibitors of β-Amylid 1-42 Secretion", J. Med. Chem. 48 p. 5705 (2005).
Saudek, C., et al. "A Preliminary Trial of the Programmable Implantable Medication System for Insulin Delivery", N. Engl. J. Med. P. 321 (1989).
Schweisguth, F., et al. Regulation of Notch Signaling Activity, Curr. Biol. 14, p. R129 (2004).
Sefton, M., "Implantable Pumps", CRC Crit. Ref. Biomed. Eng. 14, p. 201 (1987).
Shimizu, K., et al. "Binding of Delta1, Jagged1, and Jagged2 to Notch2 Rapidly Induces Cleavage, Nuclear Translocation, and Hyperphosphorylation of Notch2", Mol. Cell. Biol. 20, p. 6913 (2000).
Steiner, H., "Uncovering γ-Sucretase", Curr. Alzheimer Research 1(3), p. 175 (2004).
Tanzi, R., et al. "Twenty Years of the Alzlheimer's Disease Amyloid Hypothesis: A Genetic Perspective", Cell, vol. 120, (2005) p. 545-555.
Vassar, R., et al. "β-Secretese Cleavage of Alzheimer's Amyloid Precursor Protein by the Transmembrane Aspartic Protease BACE", science 286, p. 735 (1999).
Wang, R., et al. "The Profile of Soluble Amyloid βProtein in Cultured Cell Media", J. Biol. Chem. 271 p. 31894 (1996).
Weggen, S., et al. "A Subset of NSAIDs Lower Amylidogenic Aβ42 Independently of Cyclooxygenase Activity", Nature 414, p. 212 (2001).
Xia, W., et al. "Preseilin 1 Regulates the Processing of β-Amyloid Precursor Protein C-Terminal Fragments and the Generation of Amyloid β-Protein in Endoplasmic Reticulum and Golgi", Biochemistry 3, 16465 (1998).

Yan, R., et al. "Membrane Anchored Aspartyl Protease with Alzheimer's Disease βSecretase Activity", Nature 402, p. 533 (1999).
Yan, Q., et al. "Anti-Inflammatory Drug Therapy Alters β-Amyloid Processing and Deposition in an Animal Model of Alzheimer's Disease", Journal of Neuroscience 23(20), p. 7504 (2003).
Caplus Accession No. 1973:124623, "Pharmacologically active ethyl 4-amino-2-(p-chlorophenyl)pyrimidin-6-yl acetate", 2011, 4 pages.
Caplus Accession No. 2007:1201441, "Preparation of terphenylcarboxylates for treatment of Alzheimer's disease", 2010, 3 pages.
Citron, M., et al., "Mutant Preseniliines of Alzheimer's Disease Increase Production of 42-Residue Amyloid β-protein in Both Transfected Cells and Transgenic Mice", Nature Medicine, vol. 3, No. 1, Jan. 1997, p. 67-72.
Curtis, W., et al., 1,6,13,8,25,30-Hexaoxa[6.6.6.](1,3,5)cyclophane. Attempted Synthesis of a [4] Cyptand Journal of the Chemical Society, Perkin Transactions 1:Oranic and Bio-Organic Chemistry (7), 1977, p. 785-788, XP-002508187.
Evans, D., et al., "Synthesis of Diaryl Ethers through the Cooper-Promoted arylation of Phenols with Arylbornic Acids. An Expedient Synthesis of Thyroxine", Tetrahedron Letter 39, No. 19, May 7, 1998, 2937-2940.
HCaplus Accession No. 1974:47782, "Pyrylium salts from pyrones and some organometallic compounds", 2009, 2 pages.
Hendrickson, J., et al., "A New Synthesis of Depsidones>Diplocin and Gangaleoidin", Jornal of the American Chemical Society 94:19, 1972, p. 6834-6843, XP-002508189.
International Patent Application No. PCT/US2008/079905: International Search Report dated Aug. 1, 2009, 2 pages.
Kaminski, T., et al., "Side-Chain Retention During Lithiation of 4-Picoline and 3,4-Lutidine:Easy Access to Moledular Diversity in Pyridin Series", European Journal Organic Chemistry, 2003, p. 3855-3860.
Lin et al., "Structure-Activity Studies on a Novel series of Cholinergic Channel Activiators Based on a Heteroaryl Ether Framework", Bioorganic and Medicinal Chemistry Letters, Perfamon, vol. 9, 1999, pp. 2747-2752.
Nesmeyanov, E., et al. "Immediate Cyanization of Ferricinium Salts", Department for Organic Chemistry of the Moscow State University, Jul. 1960, 7 pages.
Patani et al., "Biososterism: A rational approach in drug Design", Chem. Rev. 96, Jul. 1996, pp. 3147-3176.
Shih, I-M., et al. Cancer Research, 2007, vol. 67, pp. 1879-1882.
Shu, Y., et al. "Novel Potent Antagonist of Transient Receptor Potential Channel, Vanilloid Subfamily Member1: Structure-Activity Relationship of 1,2-Diarylalkyl Thioureas Possessing New Vanilloid Equivalents", Journal of Medicinal Chemistry, 18, 2005, p. 7434.
Silverman, R. "The Organic Chemistry of Drug Design and Drug Action," 2004, Elsevier, pp. 29-32.
Tagat, et al., Bioorganic and Medicinal Chemistry Letters, Pergamon, vol. 5, No. 18, 1995, pp. 2143-2146.
Thompson (Huffman), et al. "The Conversion of Phenols to the Corresponding Aryl Halides Under Mild Conditions", Synthesis No. 4, 2005, Jan. 18, 2005, 4 pages.
Vippagunta et al., "Crystalline Solids" Advanced Drug Delivery Reviews, Elsevier, vol. 48, 2001, pp. 3-26.
Vu, B., et al., "A Simple Method for the Preparation of 2-Arylbenzofurans and the Synthesis of Moracind A and B", Liebigs Annalen Der Chemie, 1984, p. 734-741, XP-00250818, (with English Abstract).
West, "Solid State Chemistry and its Applications", Wiley New York, Mar. 3, 1988, pp. 358 and pp. 365.
International Patent Application No. PCT/US2008/080241: International Search Report dated Feb. 20, 2009, 2 pages.
Krivun et al, "Pyrylium salts from pyrones and some organometallic compounds" Chemistry of Heterocyclic Compounds, 1973, 9, 1191-1194, (Abstract only).

* cited by examiner

CARBON LINKED MODULATORS OF GAMMA-SECRETASE

CROSS REFERENCE TO RELATED APPLICATIONS

This application claims priority of the benefits of the filing of U.S. Provisional Application Ser. No. 60/981,209, filed Oct. 19, 2007. The complete disclosures of the aforementioned related U.S. patent application is/are hereby incorporated herein by reference for all purposes.

FIELD OF THE INVENTION

The present invention relates the use of compounds having the general Formula I, wherein the definitions or A, X, $R^1$ $R^3$, $R^4$, $R^5$, $R^6$, $R^7$, $R^8$, and $R^9$ are provided in the specification. Compounds of Formula I are useful for the treatment of diseases associated with γ-secretase activity, including Alzheimer's disease.

BACKGROUND OF THE INVENTION

Alzheimer's Disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. There is currently no effective treatment for AD. The total net cost related to AD in the U.S. exceeds $100 billion annually.

AD does not have a simple etiology, however, it has been associated with certain risk factors including (1) age, (2) family history (3) and head trauma; other factors include environmental toxins and low level of education. Specific neuropathological lesions in the limbic and cerebral cortices include intracellular neurofibrillary tangles consisting of hyperphosphorylated tau protein and the extracellular deposition of fibrillar aggregates of amyloid beta peptides (amyloid plaques). The major component of amyloid plaques are the amyloid beta (A-beta, Abeta or Aβ) peptides of various lengths. A variant thereof, which is the Aβ1-42-peptide (Abeta-42), is believed to be the major causative agent for amyloid formation. Another variant is the Aβ1-40-peptide (Abeta-40). Amyloid beta is the proteolytic product of a precursor protein, beta amyloid precursor protein (beta-APP or APP).

Familial, early onset autosomal dominant forms of AD have been linked to missense mutations in the β-amyloid precursor protein (β-APP or APP) and in the presenilin proteins 1 and 2. In some patients, late onset forms of AD have been correlated with a specific allele of the apolipoprotein E (ApoE) gene, and, more recently, the finding of a mutation in alpha2-macroglobulin, which may be linked to at least 30% of the AD population. Despite this heterogeneity, all forms of AD exhibit similar pathological findings. Genetic analysis has provided the best clues for a logical therapeutic approach to AD. All mutations, found to date, affect the quantitative or qualitative production of the amyloidogenic peptides known as Abeta-peptides (Aβ), specifically Aβ42, and have given strong support to the "amyloid cascade hypothesis" of AD (Tanzi and Bertram, 2005, Cell 120, 545). The likely link between Aβ peptide generation and AD pathology emphasizes the need for a better understanding of the mechanisms of Aβ production and strongly warrants a therapeutic approach at modulating Aβ levels.

The release of Aβ peptides is modulated by at least two proteolytic activities referred to as β- and γ-secretase cleaving at the N-terminus (Met-Asp bond) and the C-terminus (residues 37-42) of the Aβ peptide, respectively. In the secretory pathway, there is evidence that β-secretase cleaves first, leading to the secretion of s-APPβ (sβ) and the retention of a 11 kDa membrane-bound carboxy terminal fragment (CTF). The latter is believed to give rise to Aβ peptides following cleavage by γ-secretase. The amount of the longer isoform, Aβ42, is selectively increased in patients carrying certain mutations in a particular protein (presenilin), and these mutations have been correlated with early-onset familial Alzheimer's disease. Therefore, Aβ42 is believed by many researchers to be the main culprit of the pathogenesis of Alzheimer's disease.

It has now become clear that the γ-secretase activity cannot be ascribed to a single particular protein, but is in fact associated with an assembly of different proteins.

The gamma-secretase activity resides within a multiprotein complex containing at least four components; the presenilin (PS) heterodimer, nicastrin, aph-1 and pen-2. The PS heterodimer consists of the amino- and carboxyterminal PS fragments generated by endoproteolysis of the precursor protein. The two aspartates of the catalytic site are at the interface of this heterodimer. It has recently been suggested that nicastrin serves as a gamma-secretase-substrate receptor. The functions of the other members of gamma-secretase are unknown, but they are all required for activity (Steiner, 2004. Curr. Alzheimer Research 1(3): 175-181).

Thus, although the molecular mechanism of the second cleavage-step has remained elusive until present, the γ-secretase-complex has become one of the prime targets in the search for compounds for the treatment of Alzheimer's disease.

Various strategies have been proposed for targeting gamma-secretase in Alzheimer's disease, ranging from targeting the catalytic site directly, developing substrate-specific inhibitors and modulators of gamma-secretase activity (Marjaux et al., 2004. Drug Discovery Today Therapeutic Strategies, Volume 1, 1-6). Accordingly, a variety of compounds were described that have secretases as targets (Lamer, 2004. Secretases as therapeutics targets in Alzheimer's disease: patents 2000-2004. Expert Opin. Ther. Patents 14, 1403-1420.)

Indeed, this finding was recently supported by biochemical studies in which an effect of certain NSAIDs on γ-secretase was shown (Weggen et al (2001) Nature 414, 6860, 212 and WO 01/78721 and US 2002/0128319; Morihara et al (2002) J. Neurochem. 83, 1009; Eriksen (2003) J. Clin. Invest. 112, 440). Potential limitations for the use of NSAIDs to prevent or treat AD are their inhibition activity of Cox enzymes, which can lead to unwanted side effects, and their low CNS penetration (Peretto et al., 2005, J. Med. Chem. 48, 5705-5720).

Thus, there is a strong need for novel compounds which modulate γ-secretase activity thereby opening new avenues for the treatment of Alzheimer's disease.

The object of the present invention is to provide such compounds.

SUMMARY OF THE INVENTION

The invention comprises the compounds having the general Formula (I)

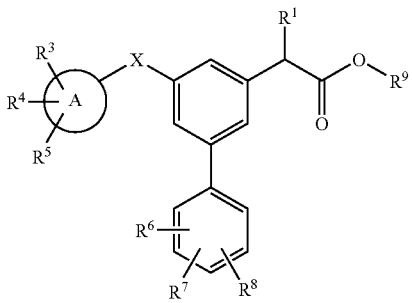

wherein A is phenyl, pyridyl, or biphenyl;
X is $CH_2$, $CH_2CH_2$, $C(O)$, $CH=CH$, $C\equiv C$, or CHOH;
$R^1$ is selected from the group consisting of H, F, alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$; alkenyl selected from $C_2H_3$, i-$C_3H_5$, n-$C_3H_5$, n-$C_4H_7$, i-$C_4H_7$, sec-$C_4H_7$; wherein said alkyl and alkenyl groups are optionally substituted with one, two, or three substituents independently selected from the group consisting of F, Cl, Br, I and $CF_3$;
$R^3$ is H, $CF_3$, $OCF_3$, F, Cl, $OCH_3$, $C_{(1-4)}$alkyl, or CN;
$R^6$ is selected from the group consisting of H, F, Cl, Br, I, CN, OH, $C(O)N(C_{(1-4)}alkyl)_2$, $S(O)_2C_{(1-4)}alkyl$, $SO_2N(C_{(1-4)}alkyl)_2$, $S(O)N(C_{(1-4)}alkyl)_2$, $N(C_{(1-4)}alkyl)S(O)_2C_{(1-4)}alkyl$, $N(C_{(1-4)}alkyl)S(O)C_{(1-4)}alkyl$, $S(O)_2C_{(1-4)}alkyl$, $N(C_{(1-4)}alkyl)S(O)_2N(C_{(1-4)}alkyl)_2$, $SC_{(1-4)}alkyl$, $N(C_{(1-4)}alkyl)_2$, $N(C_{(1-4)}alkyl)C(O)C_{(1-4)}alkyl$, $N(C_{(1-4)}alkyl)C(O)N(C_{(1-4)}alkyl)_2$, $N(C_{(1-4)}alkyl)C(O)OC_{(1-4)}alkyl$, $OC(O)N(C_{(1-4)}alkyl)_2$, $C(O)C_{(1-4)}alkyl$, $C_1$-$C_4$-alkyl, and $C_1$-$C_4$-alkoxy; wherein said alkyl and alkoxy are optionally substituted with one, two, or three substituents selected from the group consisting of F, Cl, Br, and I;
$R^4$, $R^5$, $R^7$, and $R^8$ are independently selected from the group consisting of $CF_3$, H, F, Cl, $OCH_3$, $C_{(1-4)}$alkyl, and CN;
$R^9$ is selected from the group consisting of H, alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$; alkenyl selected from $C_2H_3$, i-$C_3H_5$, n-$C_3H_5$, n-$C_4H_7$, i-$C_4H_7$, sec-$C_4H_7$; wherein said alkyl and alkenyl groups are optionally substituted with one, two, or three substituents independently selected from the group consisting of F, Cl, Br, I and $CF_3$;
and solvates, hydrates, esters, and pharmaceutically acceptable salts thereof.

DETAILED DESCRIPTION OF THE INVENTION

The invention comprises the compounds having the general Formula (I)

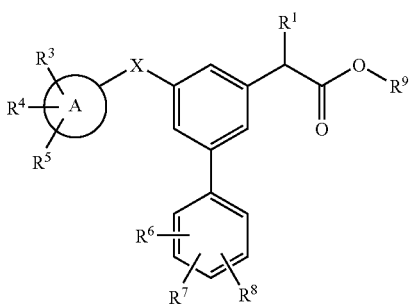

wherein A is phenyl, pyridyl, or biphenyl;
X is $CH_2$, $CH_2CH_2$, $C(O)$, $CH=CH$, $C\equiv C$, or CHOH;
$R^1$ is selected from the group consisting of H, F, alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$; and alkenyl selected from $C_2H_3$, i-$C_3H_5$, n-$C_3H_5$, n-$C_4H_7$, i-$C_4H_7$, sec-$C_4H_7$;
$R^3$ is H, $CF_3$, $OCF_3$, F, Cl, $OCH_3$, $C_{(1-4)}$alkyl, or CN;
$R^4$, $R^5$, $R^6$, $R^7$, and $R^8$ are independently selected from the group consisting of $CF_3$, H, F, Cl, $OCH_3$, $C_{(1-4)}$alkyl, and CN;
$R^9$ is selected from the group consisting of H, $CH_3$, $C_2H_5$, i-$C_3H_7$, n-$C_3H_7$, i-$C_4H_9$, n-$C_4H_9$, sec-$C_4H_9$, and tert-$C_4H_9$;
and solvates, hydrates, esters, and pharmaceutically acceptable salts thereof.

In another embodiment of the invention
A is phenyl, pyridyl, or biphenyl;
X is $CH_2$, $CH_2CH_2$, $C(O)$, $CH=CH$, $C\equiv C$, or CHOH;
$R^1$ is selected from the group consisting of H, F, alkyl selected from the group $CH_3$, $C_2H_5$, i-$C_3H_7$, n-$C_3H_7$, i-$C_4H_9$, n-$C_4H_9$, sec-$C_4H_9$, and tert-$C_4H_9$; and alkenyl selected from $C_2H_3$, i-$C_3H_5$, n-$C_3H_5$, n-$C_4H_7$, i-$C_4H_7$, and sec-$C_4H_7$;
$R^3$ is H, $CF_3$, F, Cl, $OCH_3$, $C_{(1-4)}$alkyl, or CN;
$R^4$, $R^5$, $R^6$, $R^7$, and $R^8$ are H, $CF_3$, Cl, and F;
$R^9$ is selected from the group consisting of H, $CH_3$, $C_2H_5$, i-$C_3H_7$, n-$C_3H_7$, i-$C_4H_9$, n-$C_4H_9$, sec-$C_4H_9$, and tert-$C_4H_9$;

and solvates, hydrates, esters, and pharmaceutically acceptable salts thereof.

In another embodiment of the invention

A is phenyl, pyridyl, or biphenyl;

X is $CH_2$, $CH_2CH_2$, $C(O)$, $CH=CH$, $C\equiv C$, or $CHOH$;

$R^1$ is selected from the group consisting of H, F, alkyl selected from the group $CH_3$, $C_2H_5$, $i\text{-}C_3H_7$, $n\text{-}C_3H_7$, $i\text{-}C_4H_9$, $n\text{-}C_4H_9$, $sec\text{-}C_4H_9$, and $tert\text{-}C_4H_9$; and alkenyl selected from $C_2H_3$, $i\text{-}C_3H_5$, $n\text{-}C_3H_5$, $n\text{-}C_4H_7$, $i\text{-}C_4H_7$, and $sec\text{-}C_4H_7$;

$R^3$ is H, $CF_3$, F, Cl, $OCH_3$, $C_{(1-4)}$alkyl, or CN;

$R^9$ is H;

and solvates, hydrates, esters, and pharmaceutically acceptable salts thereof.

In another embodiment of the invention

A is phenyl, pyridyl, or biphenyl;

X is $CH_2$, $CH_2CH_2$, $C(O)$, $CH=CH$, $C\equiv C$, or $CHOH$;

$R^1$ is $CH_2CH(CH_3)_2$;

$R^3$ is H, $CF_3$, F, Cl, $OCH_3$, $C_{(1-4)}$alkyl, or CN;

$R^4$ and $R^5$ are $CF_3$, Cl, F, or H;

$R^6$ is $CF_3$;

$R^7$ and $R^8$ are H;

$R^9$ is H;

and solvates, hydrates, esters, and pharmaceutically acceptable salts thereof.

6. A compound selected from the group consisting of:

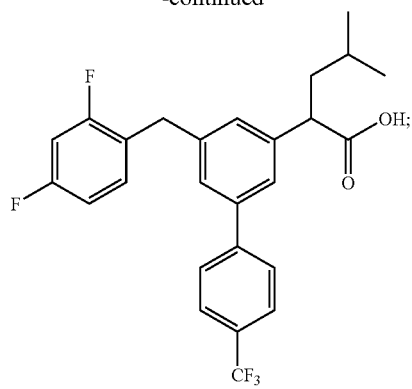

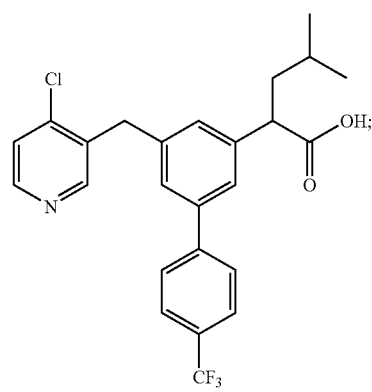

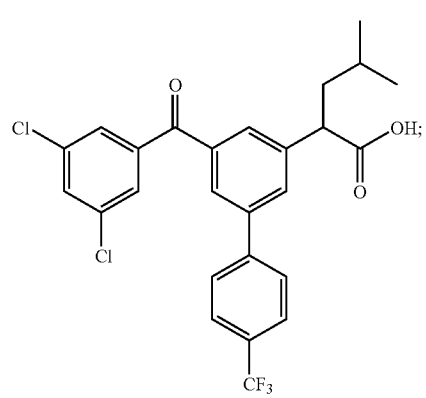

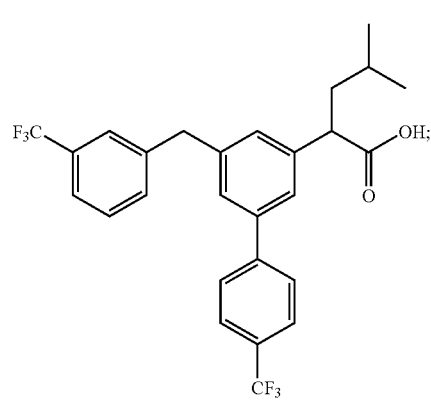

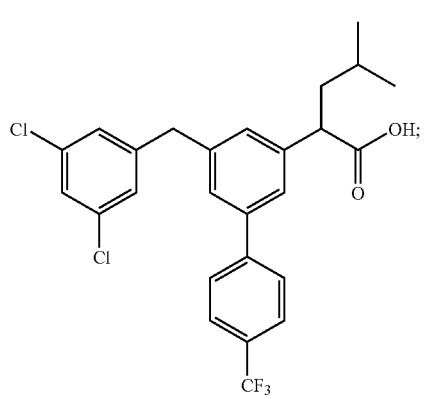

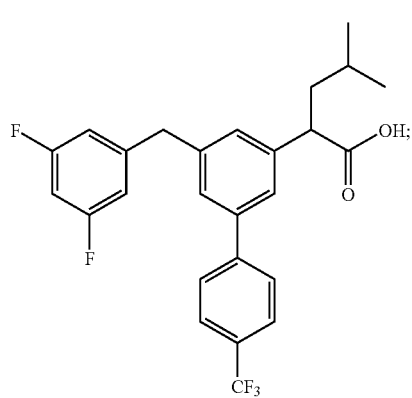

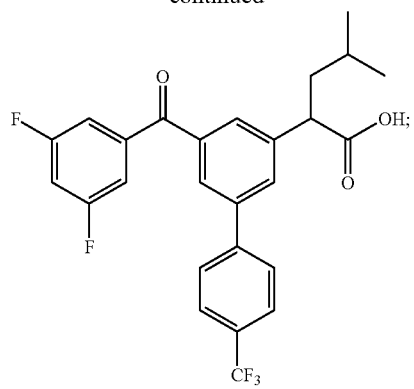
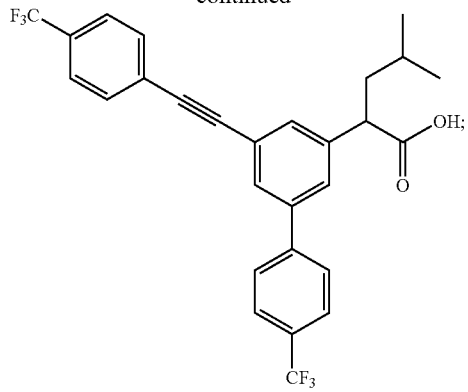
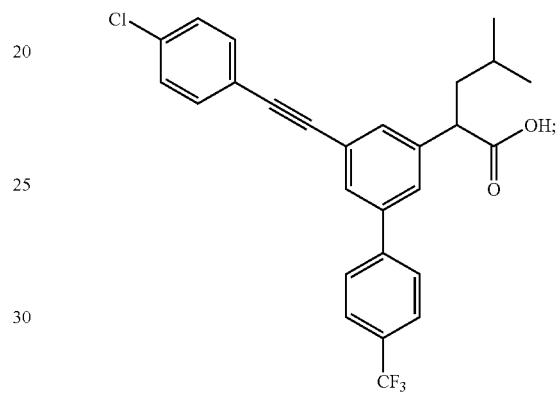
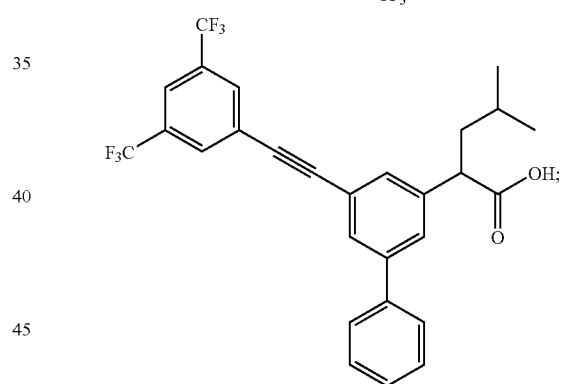
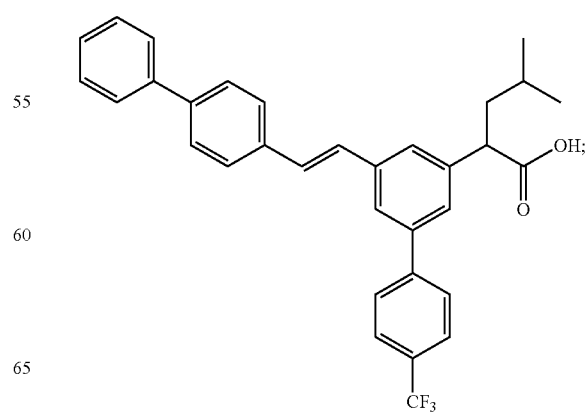

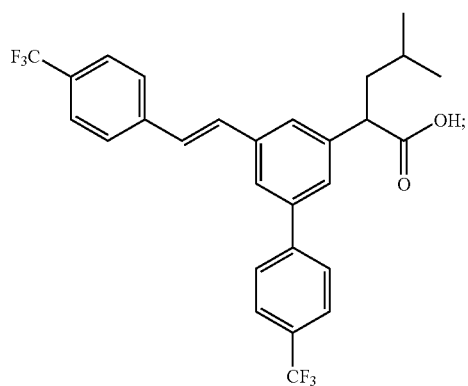
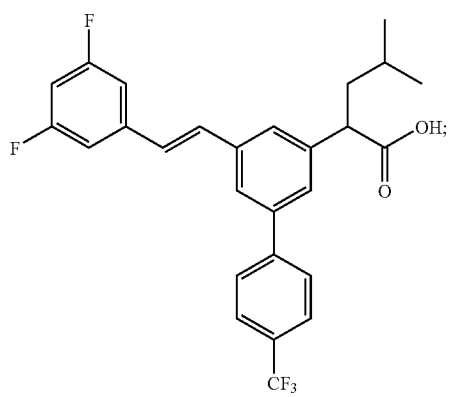 [SMILES: CC(C)CC(C(=O)O)c1cc(CCc2cc(F)cc(F)c2)cc(-c2ccc(C(F)(F)F)cc2)c1]
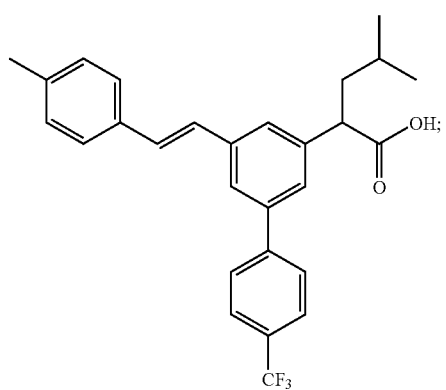
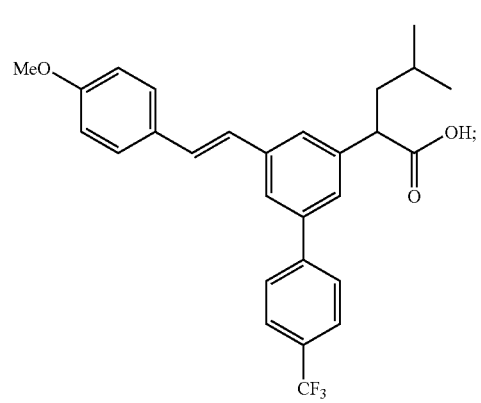
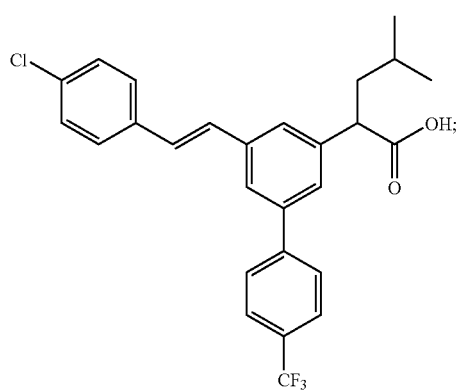
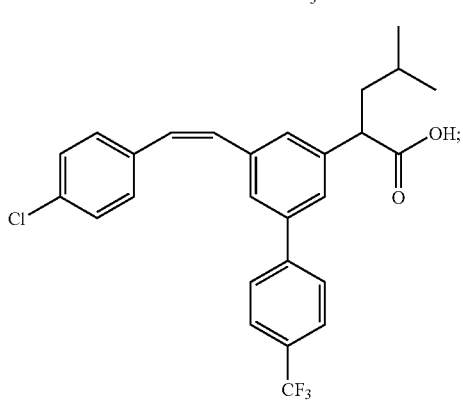
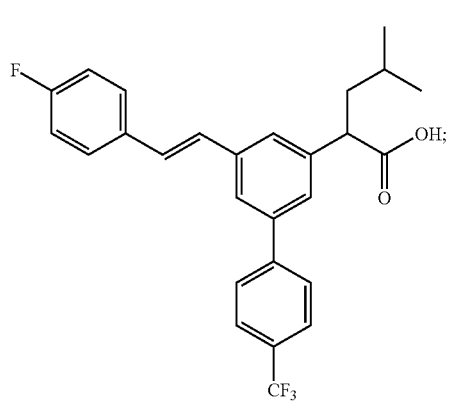
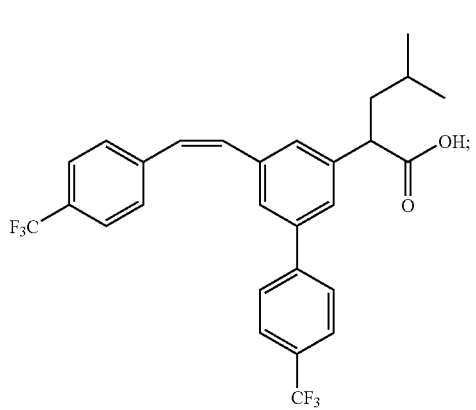

-continued

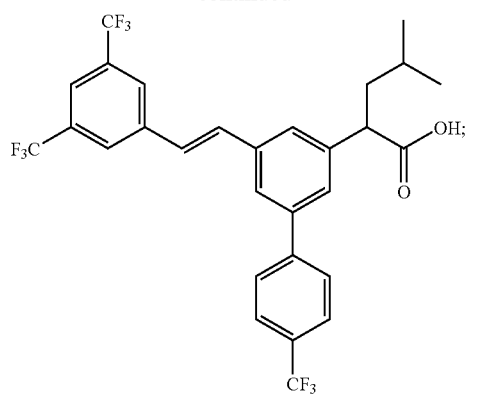

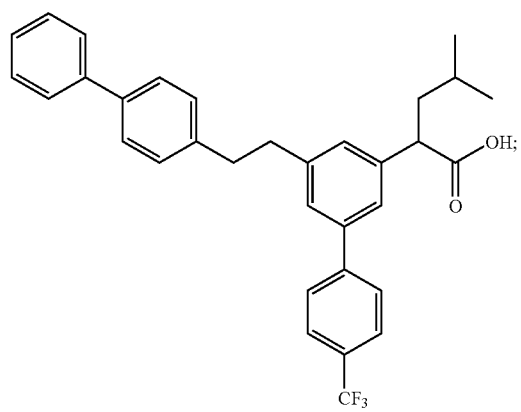

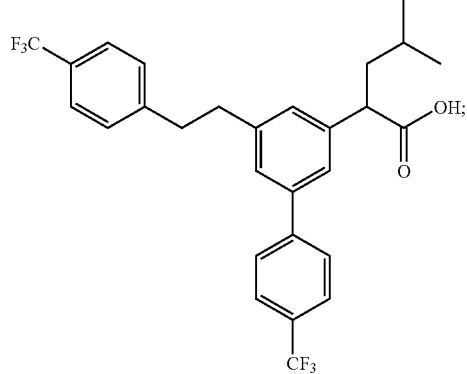

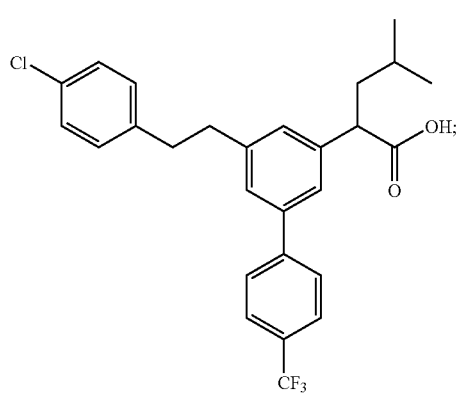

-continued

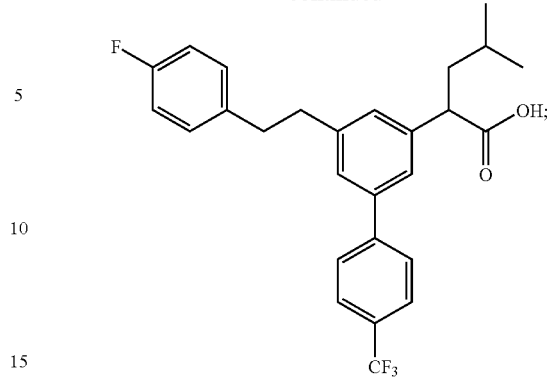

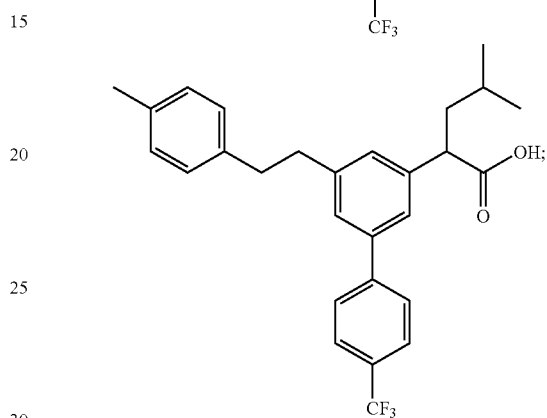

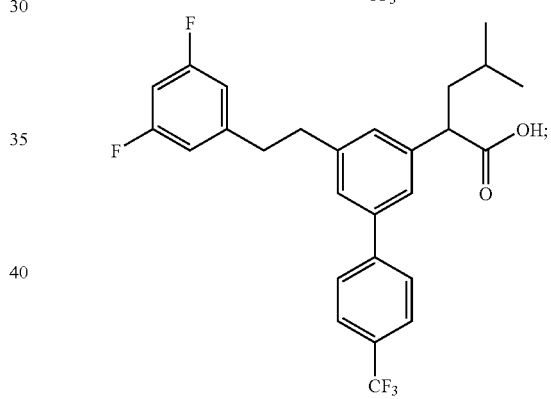

and solvates, hydrates, esters, and pharmaceutically acceptable salts thereof.

In another embodiment, the invention relates to a compound as described in the above examples or Formula I for use as a medicament.

In another embodiment, the invention relates to the use of a compound according to the above examples or Formula I for the preparation of a medicament for the modulation of γ-secretase.

In another embodiment, the invention relates to the use of a compound according to the above examples or Formula I for the preparation of a medicament for the treatment of a disease associated with an elevated level of Aβ42-production.

In another embodiment, the invention relates to the use of a compound according to the above examples or Formula I for the preparation of a medicament for the treatment of Alzheimer's disease.

In another embodiment, the invention relates to a method of treating a mammal for the modulation of γ-secretase, wherein said method comprises administering to the mammal a therapeutically effective amount of a compound of Formula I.

In another embodiment, the invention relates to a method of treating in a mammal a disease associated with an elevated level of Aβ42-production, wherein said method comprises administering to the mammal a therapeutically effective amount of a compound of Formula I.

One skilled in the art will recognize that the compounds of Formula I may have one or more asymmetric carbon atoms in their structure. It is intended that the present invention include within its scope single enantiomer forms of the compounds, racemic mixtures, and mixtures of enantiomers in which an enantiomeric excess is present.

Some of the compounds of the inventions and/or salts or esters thereof will exist in different stereoisomeric forms. All of these forms are subjects of the invention.

Described below are exemplary salts of the compounds according to the invention which are included herein. The list of the different salts stated below is not meant to be complete and limiting.

Compounds according to the invention which contain one or more acidic groups can be used according to the invention, e.g. as their alkali metal salts, alkaline earth metal salts or ammonium salts. More precise examples of such salts include sodium salts, potassium salts, calcium salts, magnesium salts or salts with ammonia or organic amines such as, e.g. ethylamine, ethanolamine, triethanolamine or amino acids.

The term "pharmaceutically acceptable" means approved by a regulatory agency such as the EMEA (Europe) and/or the FDA (US) and/or any other national regulatory agency for use in animals, preferably in humans.

The respective salts of the compounds according to the invention can be obtained by customary methods which are known to the person skilled in the art, for example by contacting these with an organic or inorganic base in a solvent or dispersant, or by cation exchange with other salts.

Furthermore, the invention includes all salts of the compounds according to the invention which, owing to low physiological compatibility, are not directly suitable for use in pharmaceuticals but which can be used, for example, as intermediates for chemical reactions or for the preparation of pharmaceutically acceptable salts or which might be suitable for studying γ-secretase modulating activity of a compound according to the invention in any suitable manner, such as any suitable in vitro assay.

The invention is considered to include prodrugs, i.e., derivatives of an acting drug that possess superior delivery capabilities and therapeutic value as compared to the acting drug. Prodrugs are transformed into active drugs by in vivo enzymatic or chemical processes.

The present invention furthermore includes all solvates of the compounds according to the invention.

The present invention furthermore includes derivatives/prodrugs (including the salts thereof) of the compounds according to the invention which contain physiologically tolerable and cleavable groups and which are metabolized in animals, preferably mammals, most preferably humans into a compound according to the invention.

The present invention furthermore includes the metabolites of the compounds according to the invention.

The term "metabolites" refers to all molecules derived from any of the compounds according to the invention in a cell or organism, preferably mammal.

Preferably the term "metabolites" relates to molecules which differ from any molecule which is present in any such cell or organism under physiological conditions.

The structure of the metabolites of the compounds according to the invention will be obvious to any person skilled in the art, using the various appropriate methods.

The invention also relates to compounds of the invention for use as medicaments. The compounds are as defined above, furthermore with respect to the medicaments the embodiments as described below with respect to the use of the invention, e.g. formulation, application and combination, also apply to this aspect of the invention.

In particular the compounds according to the invention are suitable for the treatment of Alzheimer's disease.

Details relating to said use are further disclosed below.

The compounds can be used for modulation of γ-secretase activity.

As used herein, the term "modulation of γ-secretase activity" refers to an effect on the processing of APP by the γ-secretase-complex. Preferably it refers to an effect in which the overall rate of processing of APP remains essentially as without the application of said compounds, but in which the relative quantities of the processed products are changed, more preferably in such a way that the amount of the Aβ42-peptide produced is reduced. For example a different Abeta species can be produced (e.g. Abeta-38 or other Abeta peptide species of shorter amino acid sequence instead of Abeta-42) or the relative quantities of the products are different (e.g. the ratio of Abeta-40 to Abeta-42 is changed, preferably increased).

Gamma secretase activity can e.g. be measured by determining APP processing, e.g. by determining the levels of Abeta peptide species produced, most importantly levels of Abeta-42 (see Example section, infra).

It has been previously shown that the γ-secretase complex is also involved in the processing of the Notch-protein. Notch is a signaling protein which plays a crucial role in developmental processes (e.g. reviewed in Schweisguth F (2004) Curr. Biol. 14, R129). With respect to the use of said compounds for the modulation of γ-secretase activity in therapy, it seems particularly advantageous not to interfere with the Notch-processing activity of the γ-secretase activity in order to avoid putative undesired side-effects. Thus, compounds are preferred which do not show an effect on the Notch-processing activity of the γ-secretase-complex.

Within the meaning of the invention, "effect on the Notch processing activity" includes both an inhibition or an activation of the Notch-processing activity by a certain factor.

A compound is defined as not having an effect on the Notch processing activity, if said factor is smaller than 20, preferably smaller than 10, more preferably smaller than 5, most preferably smaller than 2 in the respective assay as described in Shimizu et al (2000) Mol. Cell. Biol, 20: 6913 at a concentration of 30 μM.

Such a γ-secretase modulation can be carried out, e.g. in animals such as mammals. Exemplary mammals are mice, rats, guinea pigs, monkeys, dogs, cats. The modulation can also be carried out in humans. In a particular embodiment of the invention, said modulation is performed in vitro or in cell culture. As known to the person skilled in the art, several in vitro and cell culture assays are available.

Exemplary assays useful for measuring the production of C-terminal APP fragments in cell lines or transgenic animals by Western blot analysis include but are not limited to those described in Yan et al., 1999, Nature 402, 533-537.

An example of an in vitro γ-secretase assay is described in WO-03/008635. In this assay a suitable peptide substrate is contacted with a γ-secretase preparation and the ability to cleave the substrate is measured.

Concentrations of the various products of the γ-secretase cleavage (the Aβ-peptides) can be determined by various methods known to a person skilled in the art. Examples for such methods include determination of the peptides by mass-spectrometry or detection by antibodies.

Exemplary assays useful for the characterization of the profile of soluble Aβ peptides in cultured cell media and biological fluids include but are not limited to those described by Wang et al., 1996, J. Biol. Chem. 271, 31894-31902. In this assay a combination of immunoprecipitation of Abeta-peptides with specific antibodies and detection and quantification of the peptide species with matrix-assisted laser desorption ionization time-of-flight mass spectrometry is used.

Exemplary assays useful for measuring the production of Abeta-40 and Abeta-42 peptides by ELISA include but are not limited to those described in Vassar et al, 1999, Science 286, 735-741. Further information is disclosed for example in N. Ida et al. (1996) J. Biol. Chem. 271, 22908, and M. Jensen et al. (2000) Mol. Med. 6, 291. Suitable antibodies are available for example from The Genetics Company, Inc., Switzerland. Antibody-based kits are also available from Innogenetics, Belgium.

Cells which can be employed in such assays include cells which endogenously express the γ-secretase complex and transfected cells which transiently or stably express some or all interactors of the γ-secretase complex. Numerous available cell lines suitable for such assays are known to the skilled person. Cells and cell lines of neuronal or glial origin are particularly suitable. Furthermore, cells and tissues of the brain as well as homogenates and membrane preparations thereof may be used (Xia et al., 1998, Biochemistry 37, 16465-16471).

Such assays might be carried out for example to study the effect of the compounds according to the invention in different experimental conditions and configurations.

Furthermore, such assays might be carried out as part of functional studies on the γ-secretase complex.

For example, either one or more interactors (either in their wild-type form or carrying certain mutations and/or modifications) of the γ-secretase complex of an animal, preferably a mammal, more preferably humans, might be expressed in certain cell lines and the effect of the compounds according to the invention might be studied.

Mutated forms of the interactor(s) used can either be mutated forms which have been described in certain animals, preferably mammals, more preferably humans or mutated forms which have not previously been described in said animals.

Modifications of the interactors of the γ-secretase complex include both any physiological modification of said interactors and other modifications which have been described as modifications of proteins in a biological system.

Examples of such modifications include, but are not limited to, glycosylation, phosphorylation, prenylation, myristylation and farnesylation.

Furthermore, the compounds according to the invention can be used for the preparation of a medicament for the modulation of γ-secretase activity.

The activity of the γ-secretase can be modulated in different ways, i.e. resulting in different profiles of the various Aβ-peptides.

Respective dosages, routes of administration, formulations etc are disclosed further below.

The invention further relates to the use of the compounds of Formula I for the treatment of a disease associated with an elevated level of Aβ42-production. The disease with elevated levels of Abeta peptide production and deposition in the brain is typically Alzheimer's disease (AD), cerebral amyloid angiopathy, multi-infarct dementia, dementia pugilistica or Down syndrome, preferably AD.

As used herein, the term "treatment" is intended to refer to all processes, wherein there may be a slowing, interrupting, arresting, or stopping of the progression of a disease, but does not necessarily indicate a total elimination of all symptoms.

As used herein, the term "elevated level of Aβ42-production" refers to a condition in which the rate of production of Aβ42-peptide is increased due to an overall increase in the processing of APP or, preferably, it refers to a condition in which the production of the Aβ42 peptide is increased due to a modification of the APP-processing profile in comparison to the wild-type APP and non-pathological situation.

As outlined above, such an elevated Aβ42-level is a hallmark of patients developing or suffering from Alzheimer's disease.

One advantage of the compounds or a part of the compounds of the present invention may lie in their enhanced CNS-penetration.

Furthermore the invention relates to a pharmaceutical composition comprising a compound of Formula I in a mixture with an inert carrier.

Modulators of γ-secretase derived from compounds of Formula I can be formulated into pharmaceutical compositions comprising a compound of Formula I in a mixture with an inert carrier, where said inert carrier is a pharmaceutical carrier.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

The compounds according to the invention and their pharmaceutically acceptable salts, optionally in combination with other pharmaceutically active compounds are suitable to treat or prevent Alzheimer's disease or the symptoms thereof. Such additional compounds include cognition-enhancing drugs such as acetylcholinesterase inhibitors (e.g. Donepezil, Tacrine, Galantamine, Rivastigmin), NMDA antagonists (e.g. Memantine) PDE4 inhibitors (e.g. Ariflo) or any other drug known to a person skilled in the art suitable to treat or prevent Alzheimer's disease. Such compounds also include cholesterol-lowering drugs such as statins (e.g. simvastatin). These compounds can be administered to animals, preferably to mammals, and in particular humans, as pharmaceuticals by themselves, in mixtures with one anther or in the form of pharmaceutical preparations.

Preservatives and other additives can also be present, such as, for example, antimicrobials, antioxidants, chelating agents, inert gases and the like. All carriers can be mixed as needed with disintegrants, diluents, granulating agents, lubricants, binders and the like using conventional techniques known in the art.

This invention further provides a method of treating a subject having a condition ameliorated by modulation of γ-secretase activity, which comprises administering to the subject a therapeutically effective dose of the instant pharmaceutical composition.

As used herein, the term "subject" includes, without limitation, any animal or artificially modified animal having a disorder ameliorated by modulation of γ-secretase activity. In a preferred embodiment, the subject is a human.

As used herein, a "therapeutically effective dose" of a pharmaceutical composition is an amount sufficient to stop, reverse or reduce the progression of a disorder. A "prophylactically effective dose" of a pharmaceutical composition is an amount sufficient to prevent a disorder, i.e., eliminate, ameliorate and/or delay the disorder's onset.

Methods are known in the art for determining therapeutically and prophylactically effective doses for the instant pharmaceutical composition. The effective dose for administering the pharmaceutical composition to a human, for example, can be determined mathematically from the results of animal studies.

Various delivery systems are known and can be used to administer a compound of the invention for the treatment of Alzheimer's disease or for the modulation of the γ-secretase activity, e.g. encapsulation in liposomes, microparticles, and microcapsules:

If not delivered directly to the central nervous system, preferably the brain, it is advantageous to select and/or modify methods of administration in such a way as to allow the pharmaceutical compound to cross the blood-brain barrier.

Methods of introduction include, but are not limited to, intradermal, intramuscular, intraperitoneal, intravenous, subcutaneous, intranasal, epidural, and oral routes.

The compounds may be administered by any convenient route, for example by infusion, by bolus injection, by absorption through epithelial or mucocutaneous linings and may be administered together with other biologically active agents.

Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g. by use of an inhaler or nebulizer, and formulation with an aerosolizing agent.

Modulators of γ-secretase derived from compounds of Formula I can be delivered in a vesicle, in particular a liposome (Langer (1990) Science 249, 1527.

Modulators of γ-secretase derived from compounds of Formula I can be delivered via a controlled release system. In one embodiment, a pump may be used (Sefton (1987) CRC Crit. Ref. Biomed. Eng. 14, 201; Buchwald et al. (1980) Surgery 88, 507; Saudek et al. (1989) N. Engl. J. Med. 321, 574). In another embodiment, polymeric materials can be used (Ranger and Peppas (1983) Macromol. Sci. Rev. Macromol. Chem. 23, 61; Levy et al. (1985) Science 228, 190; During et al. (1989) Ann. Neurol. 25, 351; Howard et al. (1989) J. Neurosurg. 71, 858). In yet another embodiment, a controlled release system can be placed in proximity of the therapeutic target, i.e., the brain, thus requiring only a fraction of the systemic dose (e.g. Goodson, 1984, In: Medical Applications of Controlled Release, supra, Vol. 2, 115). Other controlled release systems are discussed in the review by Langer (1990, Science 249, 1527).

In order to select an appropriate way of administration, the person skilled in the art will also consider routes of administration which have been selected for other known Anti-Alzheimer-drugs.

For example, Aricept/Donepezil and Cognex/Tacrine (all acetylcholinesterase-inhibitors) are being taken orally, Axura/Memantine (an NMDA-receptor antagonist) has been launched both as tablets/liquid and as an i.v.-solution.

Furthermore, the skilled person in the art will take into account the available data with respect to routes of administration of members of the NSAID-family in clinical trials and other studies investigating their effect on Alzheimer's disease.

In order to select the appropriate dosage, the person skilled in the art will choose a dosage which has been shown to be not toxic in preclinical and/or clinical studies and which can be in accordance with the values given beforehand, or which may deviate from these.

The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 mg/kg body weight to 1 mg/kg body weight. Effective doses may be extrapolated from dose-response curves derived from in vitro or animal model test systems.

An exemplary animal model is the transgenic mouse strain "Tg2576" containing an APP695-form with the double mutation KM670/671NL. For reference see e.g. patent U.S. Pat. No. 5,877,399 and Hsiao et al. (1996) Science 274, 99 and also Kawarabayahsi T (2001) J. Neurosci. 21, 372; Frautschy et al. (1998) Am. J. Pathol. 152, 307; Irizarry et al. (1997) J. Neuropathol. Exp. Neurol. 56, 965; Lehman et al. (2003) Neurobiol. Aging 24, 645.

Substantial data from several studies are available to the skilled person in the art, which are instructive to the skilled person to select the appropriate dosage for the chosen therapeutic regimen.

Numerous studies have been published in which the effects of molecules on the γ-secretase activity are described. Exemplary studies are Lim et al. (2001) Neurobiol. Aging 22, 983; Lim et al. (2000) J Neurosci. 20, 5709; Weggen et al. (2001) Nature 414, 212; Eriksen et al. (2003) J Clin Invest. 112, 440; Yan et al. (2003) J Neurosci. 23, 7504.

Definitions

The term "alkenyl," whether used alone or as part of a substituent group, for example, "$C_{1-4}$alkenyl(aryl)," refers to a partially unsaturated branched or straight chain monovalent hydrocarbon radical having at least one carbon-carbon double bond, whereby the double bond is derived by the removal of one hydrogen atom from each of two adjacent carbon atoms of a parent alkyl molecule and the radical is derived by the removal of one hydrogen atom from a single carbon atom. Atoms may be oriented about the double bond in either the cis (Z) or trans (E) conformation. Typical alkenyl radicals include, but are not limited to, ethenyl, propenyl, allyl (2-propenyl), butenyl and the like. Examples include $C_{2-8}$alkenyl or $C_{2-4}$alkenyl groups.

The term "$C_{a-b}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{1-4}$ denotes a radical containing 1, 2, 3 or 4 carbon atoms.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, n-butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "heteroaryl" refers to 5- to 7-membered mono- or 8- to 10-membered bicyclic aromatic ring systems, any ring of which may consist of from one to four heteroatoms selected from N, O or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heterocyclyl" refers to a saturated or partially unsaturated monocyclic ring radical derived by the removal of one hydrogen atom from a single carbon or nitrogen ring atom. Typical heterocyclyl radicals include 2H-pyrrolyl, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, piperidinyl, 1,4-dioxanyl, morpholinyl, 1,4-dithianyl, thiomorpholinyl, piperazinyl, azepanyl, hexahydro-1,4-diazepinyl and the like.

The term "substituted," refers to a core molecule on which one or more hydrogen atoms have been replaced with one or more functional radical moieties. Substitution is not limited to a core molecule, but may also occur on a substituent radical, whereby the substituent radical becomes a linking group.

General Synthesis Description

The following general description is for illustrative purposes only and is in no way meant to limit the invention.

Compounds of Formula I wherein X, A, $R^1$, $R^3$, $R^4$, $R^5$, $R^6$, $R^7$, and $R^8$ are defined as in Formula I, and $R^9$ is H, may be obtained by hydrolysis of esters II under standard acidic or basic hydrolysis conditions, including reaction with NaOH, at room temperature, for several hours, in an appropriate solvent mixture such as water, tetrahydrofuran (THF), and methanol or ethanol. For illustrative purposes, esters II are shown with $R^9$ as alkyl, but those skilled in the art will recognize that esters hydrolysis will work for all $R^9$ as defined in Formula I.

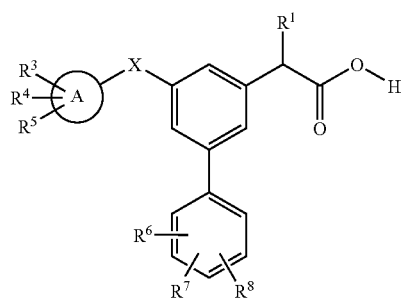

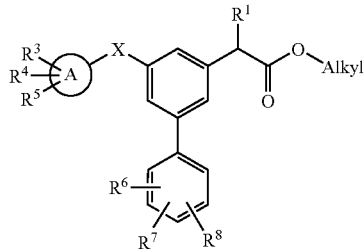

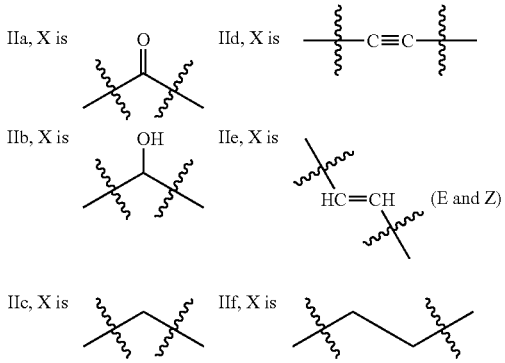

Compounds of Formula IIa, where X is a carbonyl group can be obtained by coupling of compounds IIIa or IIIb with arylboronic acids and carbon monoxide in the presence of Pd(II) catalysts such as Pd(dppf)$_2$Cl$_2$ and potassium carbonate and potassium iodide at elevated temperature (60 to 150 degrees C.).

Compounds of Formula IIb can be prepared by reduction of compounds IIa with hydride reducing agents such as sodium borohydride. Alternatively, Compounds IIb can be prepared by the addition of Grignard reagents or lithium reagents ($R^9$MgX or $R^9$Li) to compounds IIa under the general conditions for alkylation of ketones.

Compounds of Formula IIc, IId, and IIe can be prepared from the coupling of Compounds IIIa or IIIb with aryl acetylene boronic acids under Suzuki coupling conditions, e.g. in aqueous sodium carbonate in DME in the presence of Pd(PPh$_3$)$_4$ at elevated temperature (60-180 degrees C.).

Alternatively, Compounds of Formula IIc, IId, and IId can be prepared by coupling Compounds IIIa or IIIb with aryl vinyl zinc chlorides or arylmethylene zinc chlorides under Nigishi coupling reactions, e.g. in THF in the presence of a catalytic amount of Pd(dppf)$_2$Cl$_2$.

Compounds of Formula IIf can be obtained by reduction of compounds IId and IIe under the catalytic hydrogenation conditions using Pd—C, platinum oxide, or other catalysts. Alternatively, compounds of Formula IIc can be prepared from reduction of alcohol IIb with trimethylsilane in TFA-THF or catalytic hydrogenation in acid medium.

Compounds of Formula IIIa may be obtained from the reaction of phenols IV with trifluoromethanesulfonic anhydride in DCM in the presence of a base such as pyridine, or triethylamine at 0° C. Intermediates IIIb can be obtained from reactions of phenols IV with concentrated HCl, or HBr, or HI at elevated temperature (ranges from 25 to 120° C.). Alternatively, compounds IIIb can be obtained under mild conditions by treatment of the corresponding triflates IIIa with pinacoborane in dioxane in the presence of triethylamine catalyzed with PdCl$_2$ to give pinacol boronate esters which are then treated with copper (II) halide in methanol-water, procedure described by Nesmejanow et al. (Chem. Ber. 1960, 2729).

The aforementioned pinacolboronate esters could also be reacted with NaI in aqueous THF in the presence of chloramines-T to give aryl iodides described by J. W. Huffman et. al. (Synthesis, 2005, 547).

III

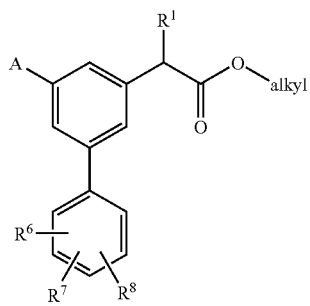

wherein:
IIIa, A = OTf
IIIb, A = Br, Cl, I

IV

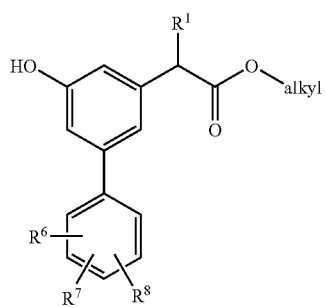

Compounds IV may be prepared by debenzylation of compounds V by hydrogenation in alcohol, e.g. MeOH or EtOH in the presence of Pd—C. Debenzylation can also be achieved with other methods, such as BBr₃ in DCM, NaCN in DMSO/ 120-200° C. or LiCl in DMF/120-200° C.

V

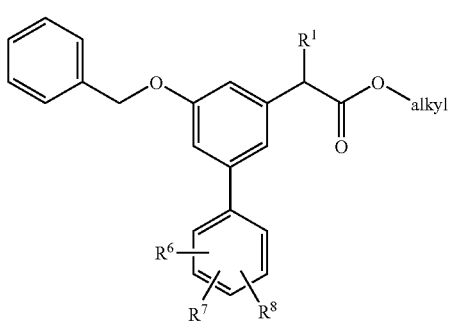

Compounds V may be prepared from alkylation of compounds VI with either alkyl or alkenyl halides. Treatment of compounds VI in THF or other aprotic solvent with a base, e.g. lithium bis(trimethylsilyl) amide, sodium bis(trimethylsilyl) amide, or lithium diisopropylamide at −78° C., followed by the addition of an electrophile, e.g. an alkyl or alkenyl halides, yields alkylated compounds V.

VI

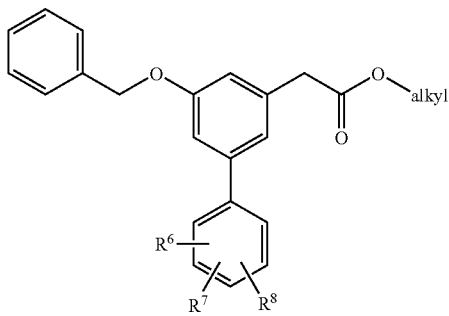

Alternatively, compounds VI may be prepared from compounds VII through a coupling reaction with an arylboronic acids under Suzuki conditions of aqueous sodium carbonate in DME in the presence of Pd(PPh₃)₄. Alternatively, the triflates can be converted to boronate esters under the conditions described above and then can be coupled with aryl bromides or aryl chlorides to give compounds VI.

VII

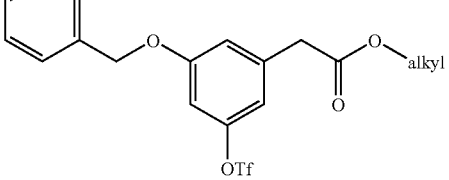

Intermediate triflate compounds VII may be prepared from compounds VIII with trifluoromethanesulfonic anhydride in DCM in the presence of one equivalent of pyridine at 0° C.

VIII

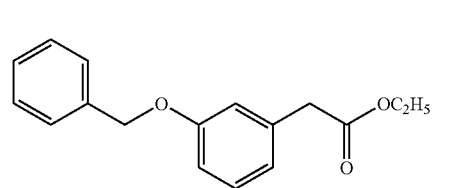

Intermediate compound VIII can be prepared from monodebenzylation of compound IX. Selective mono-debenzylation of compound IX can be achieved by selective hydrogenolysis of compound IX in ethanol or methanol with an addition of 1.1 equivalents of base, e.g. sodium hydroxide or potassium hydroxide in the presence of Pd—C catalyst in a Parr shaker. The reaction is allowed to proceed until one equivalent of hydrogen consumed

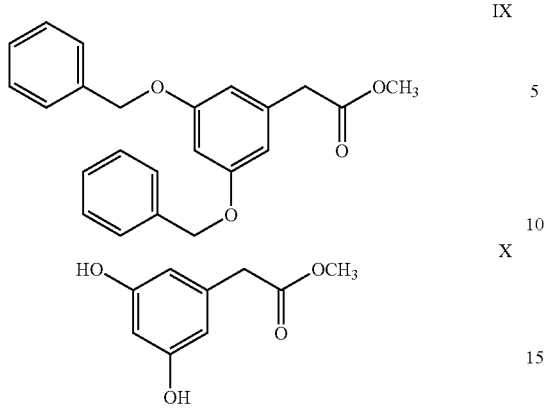

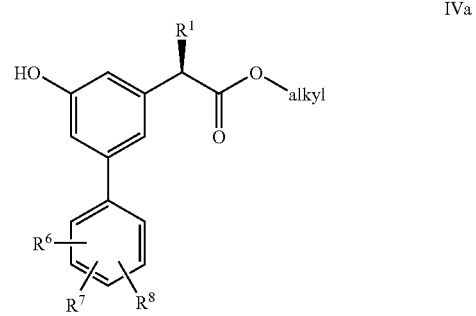

Intermediate IX can be easily prepared from reaction of 3,5-dihydroxyphenyl acetic acid methyl ester, compound X, (commercially available) with benzyl bromide and potassium carbonate in DMF at room temperature.

Compounds of Formula I have a chiral center a to the carboxylic group, and can exist as one of two enantiomers (or a mixture thereof, wherein an enantiomeric excess may or may not be present). The enantiomers Ia (R enantiomer) and Ib (S enantiomer) are shown. The pure enantiomers Ia and Ib may be obtained by chiral separation using chiral columns. The enantiomers Ia and Ib may also be separated by resolutions through forming chiral amine salts by fractional recrystallizations. The enantiomers Ia and Ib also may be obtained from kinetic resolution of the racemate of corresponding esters using lipase enzymes, e.g. Amano lipase Ak, Amano lipase PS, Amano lipaseA, Amano lipase M, Amano lipase F-15 Amano lipase G (from Biocatalytics Inc) in aqueous organic solvents, e.g. aqueous DMF, DMSO, t-butyl-ethyl ether or triton X-100 aqueous solutions.

and Ib may be obtained from reactions starting with chiral phenolic compounds IVa and IVb as described above.

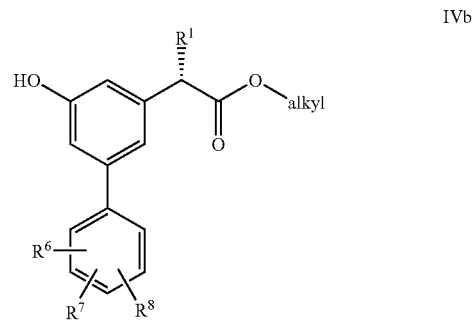

Chiral compounds IVa and IVb may be obtained from the removal of the chiral auxiliary groups from compounds XIIIa and XIIIb respectively, with lithium hydroxide/hydrogen peroxide in aqueous THF, followed by esterification.

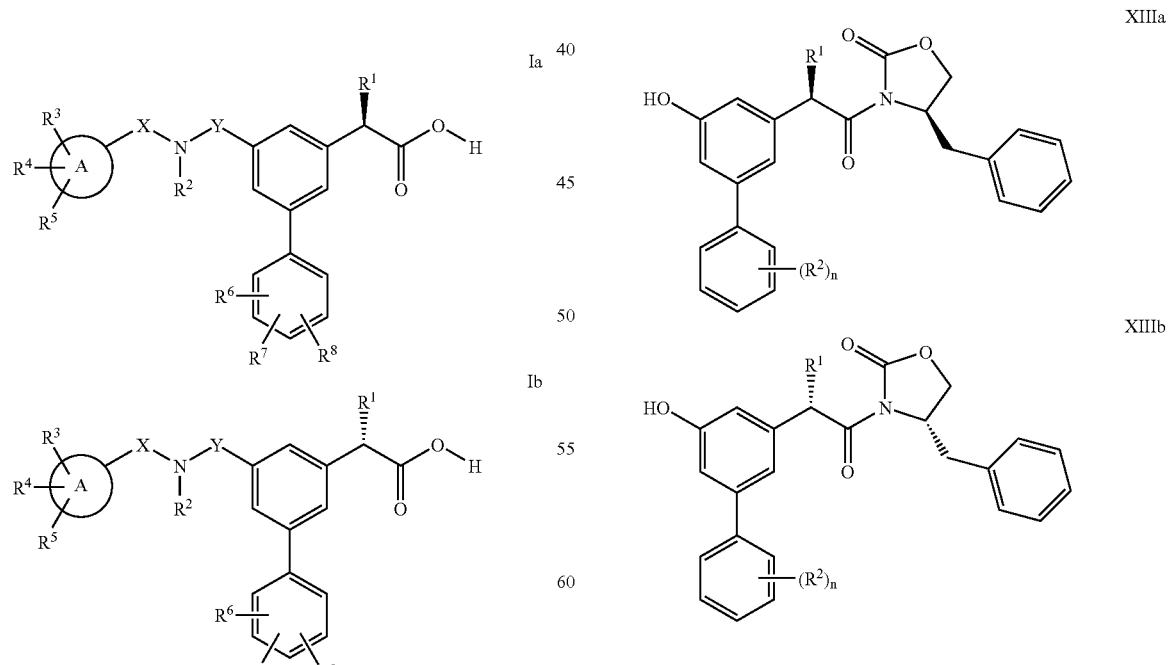

Alternatively, compounds of Formula Ia and Ib may be prepared from chiral syntheses. Compounds of Formula Ia Compounds XIIIa and XIIIb may be prepared by debenzylation of compounds XIVa and XIVb respectively by hydrogenation in an alcohol solvent, e.g. MeOH or EtOH, in the presence of Pd—C.

XIVa

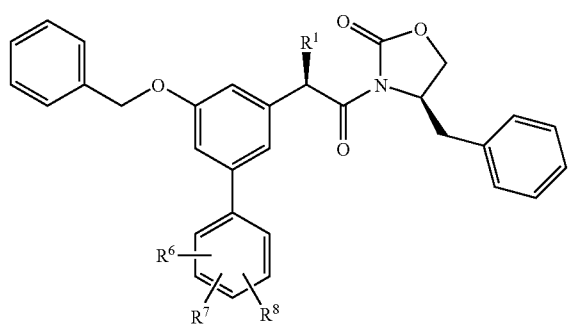

XIVb

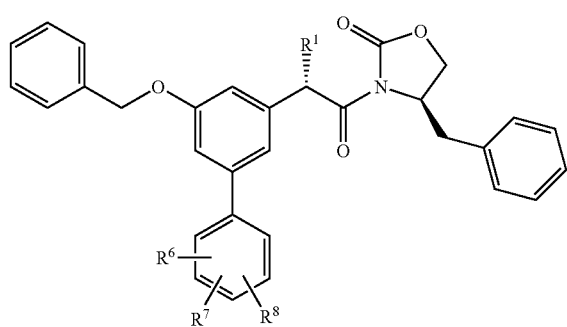

Compounds XIVa and XIVb may be prepared from the alkylation of compounds XVa and XVb respectively with an appropriate alkyl bromide, including sec-butyl bromide or sec-butenyl bromide for introducing $R^1$ group on the carbon atom a to the carboxylic group. Treatments of compounds XVa and XVb in THF or other aprotic solvents with bases, e.g. lithium bis(trimethylsilyl) amide, sodium bis(trimethylsilyl) amide, or lithium diisopropylamide at −78° C., followed by the addition of electrophiles, sec-butyl bromide or sec-butenyl bromide will give alkylated compounds XIVa and XIVb respectively.

XVa

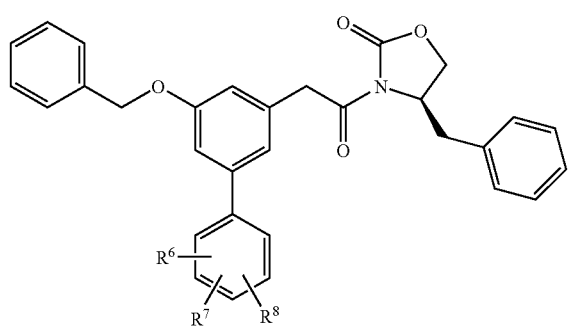

XVb

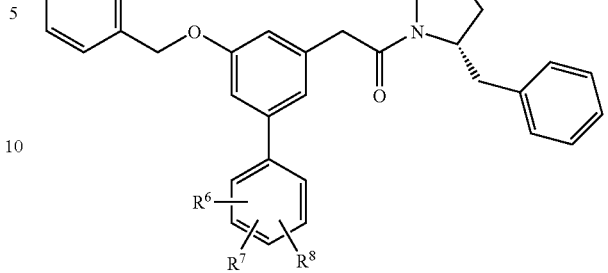

Compounds XVa and XVb may be prepared by coupling intermediates XVI with either the R-isomer of 4-benzyl-oxazolidin-one (XVIIa) or the S-isomer of 4-benzyl-oxazolidin-one (XVIIb) by Evans's procedures. Intermediates XVI may be reacted with pivaloyl chloride, oxalyl chloride or isopropyl chloroformate in THF in the presence of a base, e.g. triethylamine or N-methylmorpholine, to generate the mixed anhydrides or acid chlorides which then are reacted with the lithium salt of XVIIa or XVIIb in THF.

Alternatively, other chiral auxiliary groups may also be used for the chiral syntheses of compounds IVa and IVb, e.g. pseudoephedrine via the A. G. Myers conditions (J. Am. Chem. Soc. 1994, 116, 9361-9362). For example, treatment of either the carboxylic acid chlorides or anhydride with (+) or (−) pseudoephedrine will give compounds XVIIIa and XVIIIb. The amides are then treated with a strong base, e.g. lithium diisopropyl amide in the presence of lithium chloride, followed by the addition of an alkylating agent to yield the corresponding alkylated products XIXa and XIXb.

XVI

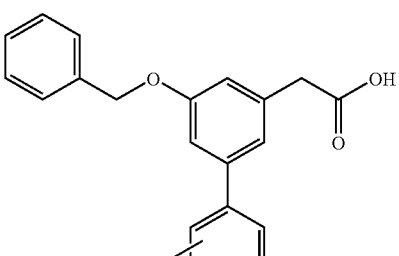

XVIIa

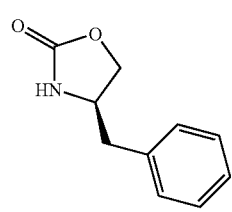

XVIIb

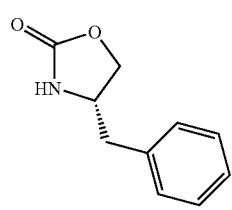

XVIIIa

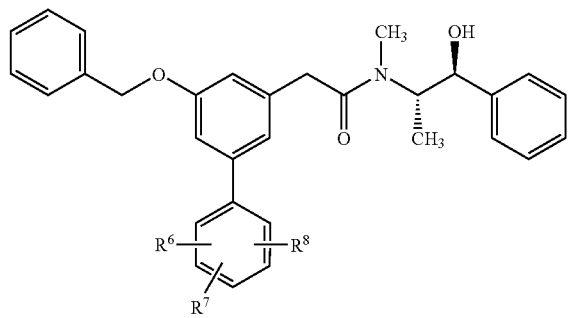

XVIIIb

XIXa

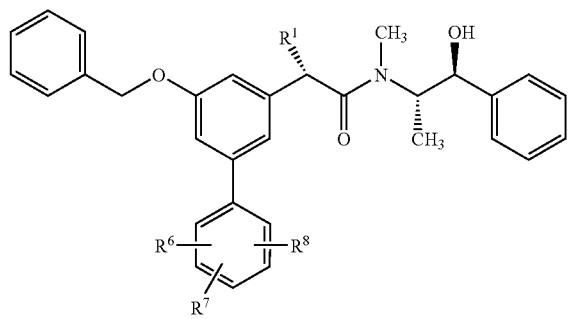

XIXb

XXa

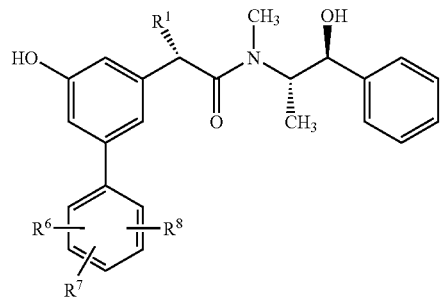

XXb

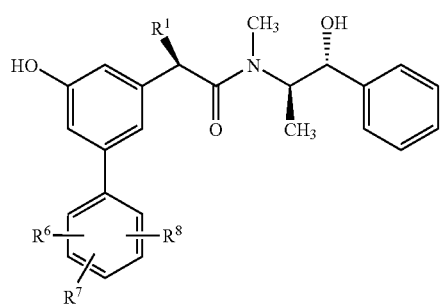

Alternatively, the chiral phenolic compounds XIIIa, XIIIb, XXa and XXb can serve as chiral intermediates for preparing chiral compounds of Formula Ia and Ib. The chiral auxiliary groups are then removed at the final stage of synthesis under the conditions described above.

XXIa

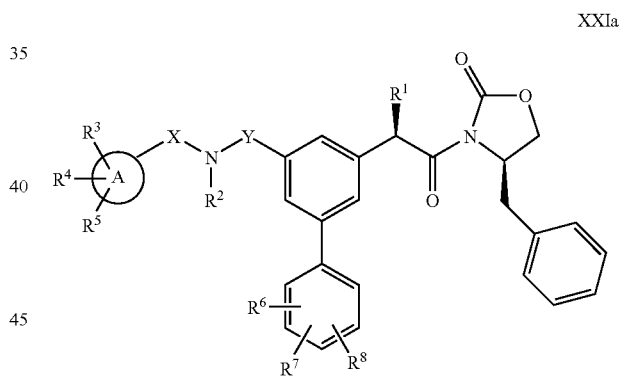

XXIb

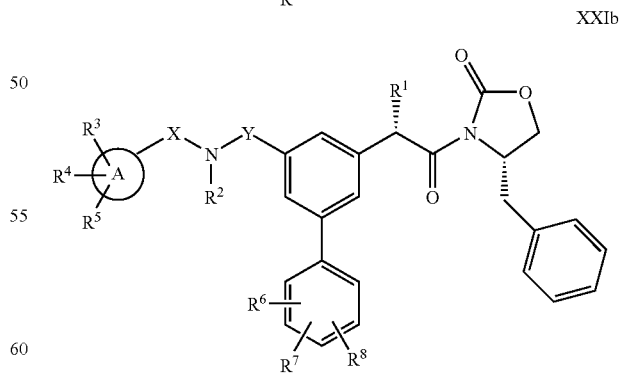

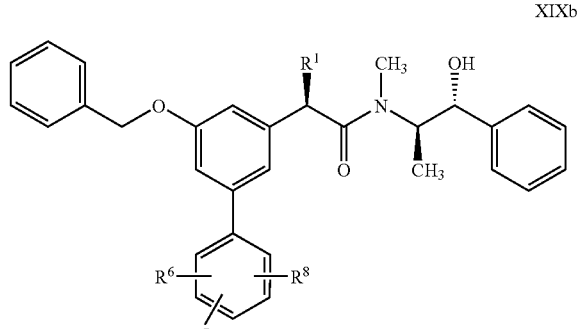

Chiral phenolic compounds IVa and IVb can also be prepared from compounds XIXa and XIXb by removal of the chiral auxiliary pseudoephedrine in sulfuric acid aqueous solution and followed by treatment of $BBr_3$/DCM to remove the benzyl protecting group.

Compounds XXIa and XXIb can be prepared from chiral phenolic compounds XIIIa and XIIIb under the similar aforementioned conditions. For example, the triflate compounds XXIIa and XXIIb, prepared from phenolic compounds XIIIa and XIIIb by reacting with trifluoromethylsulfonyl anhydride in pyridine-methylene chloride solution, can give the coupling compounds XXIa and XXIb under Buckwald or Hartwig conditions as described above.

XXIIa
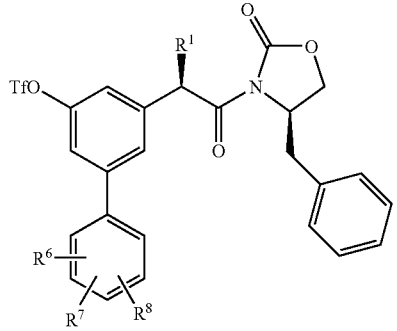

XXIIb
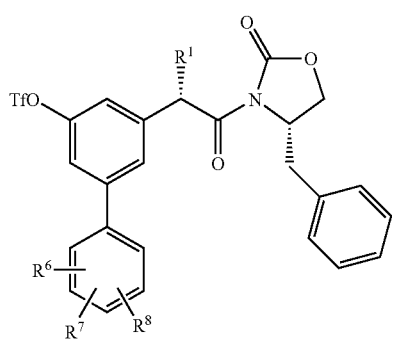

Under similar conditions, compounds XXIIIa and XXIIIb may be prepared from compounds XXIIa and XXIIb by reacting with benzophenone imine in the presence of triphenylphosphine and a catalytic amount of tetrakistriphenylphosphine palladium (0) as mentioned previously. Reductive amination of compounds XXIIIa and XXIIIb with aryl carboxyaldehydes or heteroarylcarboxyaldehydes and followed by alkylation of the nitrogen via reductive amination or alkyl halide alkylations and then removal of the chiral auxiliary groups with lithium hydroxide and hydrogen peroxide in aqueous THF gives chiral compounds Ia and Ib.

XXIIIa
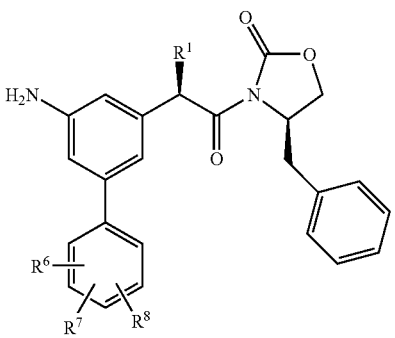

XXIIIb
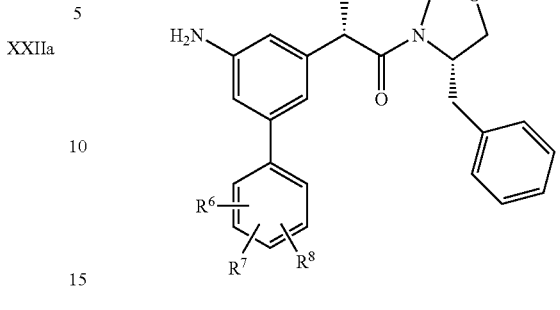

Alternatively, Compounds XXIVa and XXIVb can be prepared from XXIIa and XXIIb as described previously using zinc cyanide and tetrakistriphenylphosphine palladium followed by reduction of the cyano compounds with platinum oxide in acid alcohol medium. The chiral amine compounds XXIVa and XXIVb can be used to prepare the final target compounds of Formula Ia and Ib in similar routes as described previously.

XXIVa
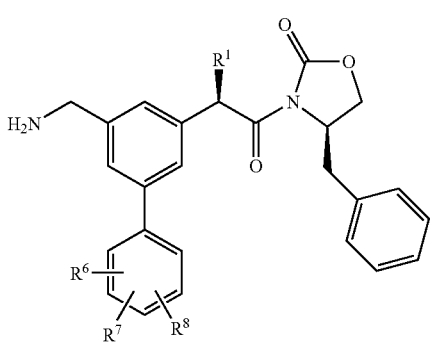

XXIVb
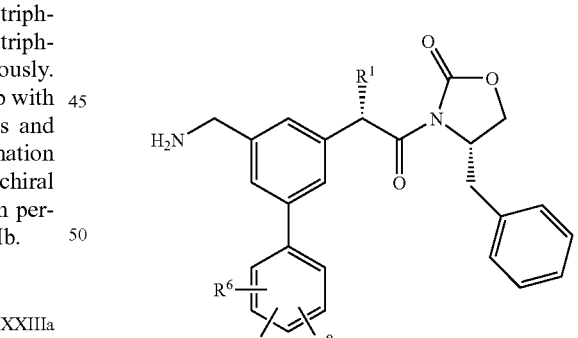

Synthetic Procedures

All reactions were carried out under inert atmosphere unless otherwise stated. NMR spectra were obtained on a Bruker dpx400. LCMS was carried out on an Agilent 1100 using a ZORBAX® SB-C18, 4.6×75 mm, 3.5 micron column for method A. Column flow was 1 ml/min and solvents used were water and acetonitrile (0.1% TFA) with an injection volume of 10 ul. Wavelengths were 254 and 210 nm. Methods are described below:

| Method | Flow Rate | Solvent |
|--------|-----------|---------|
| A | 1 ml/min | 0-1.5-95% MeCN |
|   |   | 1.5-6 min 95% |
|   |   | 4.5-5 min 95%-5% MeCN |

Abbreviations

| | |
|---|---|
| Ac | Acetyl |
| d | Doublet |
| DCM | Dichloromethane |
| DME | 1,2-dimethoxyethane |
| DMF | N,N-dimethylformamide |
| DMSO | Dimethyl sulfoxide |
| e.e. | enantiomeric excess |
| Eq | Equivalents |
| Et | Ethyl |
| EtOAc | ethyl acetate |
| g | Gram |
| h | Hour |
| HPLC | high pressure liquid chromatography |
| $K_2CO_3$ | Potassium carbonate |
| l | Litre |
| LCMS | liquid chromatography - mass spectrometry |
| LDA | lithium diisopropylamide |
| M | Molar |
| m | Multiplet |
| Me | Methyl |
| min | Minute |
| mol | Mole |
| NMR | nuclear magnetic resonance |
| q | Quartet |
| RT | Retention time |
| s | Singlet |
| sat | Saturated |
| t | Triplet |
| TFA | Trifluoroacetic acid |
| THF | Tetrahydrofuran |

Example 1

2-[5-(3,5-Dichloro-benzoyl)-4'-trifluoromethyl-biphenyl-3-yl]-4-methyl-pentanoic acid

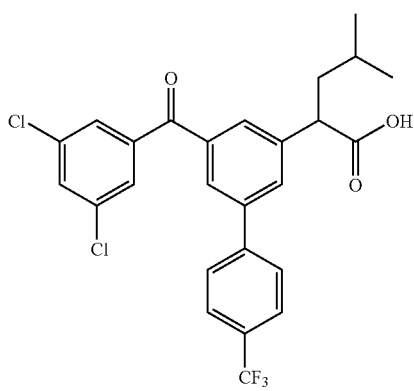 [SMILES: CC(C)CC(C(=O)O)c1cc(C(=O)c2cc(Cl)cc(Cl)c2)cc(-c2ccc(C(F)(F)F)cc2)c1]

a) (3,5-Bis-benzyloxy-phenyl)-acetic acid methyl ester

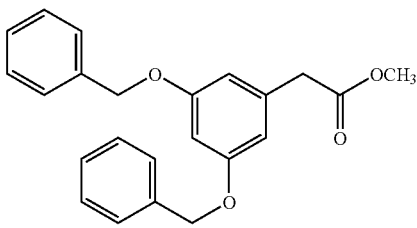 [SMILES: COC(=O)Cc1cc(OCc2ccccc2)cc(OCc2ccccc2)c1]

A mixture of (3,5-dihydroxy-phenyl)-acetic acid methyl ester (from Aldrich, 70 g, 0.385 mol), benzylbromide (137 mL, 1.16 mol), potassium carbonate (160 g, 1.16 mol) and DMF (1.5 L) under $N_2$ was mechanically stirred at room temperature overnight. The resulting reaction mixture was poured into a mixture of 1.5 L of ice-water with stirring. The precipitate was obtained by filtration and washed with heptane successively to remove benzyl bromide to give the title compounds (123.7 g) as a brown solid which was air dried for the next reaction. $^1$H-NMR (CDCl$_3$): δ 3.60 (s, 2H), 3.71 (s, 3H), 5.05 (s, 4H), 6.60 (s, 3H), 7.35-7.50 (m, 10H); Calcd for C23H22O4 (M+H) 363.15, Found 363.

b) 3-Benzyloxy-5-hydroxy-phenyl)-acetic acid ethyl ester

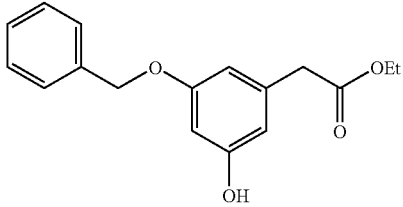 [SMILES: CCOC(=O)Cc1cc(O)cc(OCc2ccccc2)c1]

A solution of 3,5-bis-benzyloxy-phenyl)-acetic acid methyl ester (50 g, 1.38 mol) and NaOH (6.6 g, 1.65 mole) in 1 L of EtOH in the presence of 10% of Pd—C was hydrogenated in a Parr shaker until one equivalent of hydrogen was consumed. The mixture was acidified with concentrated HCl and then the catalyst and solvent were removed to give an oil residue. The crude product was purified by ISCO silica gel column chromatography (ISCO) using EtOAC-heptane as eluents (gradient from 10% to 75% of EtOAc) to give 25 g of (65% yield) the title compound. $^1$H-NMR (CDCl$_3$): δ 1.15-1.20 (t, 3H), 3.4-(s, 2H), 4.05-4.1 (q, 2H), 4.9 (s, 2H), 5.5 (s, 1H), 6.4 (s, 2H), 6.5 (s, 1H), 7.207.35 (m, 5H); Calcd for C17H18O4 (M+H) 287.3, Found 287.

c) (3-Benzyloxy-5-trifluoromethanesulfonyloxy-phenyl)-acetic acid ethyl ester

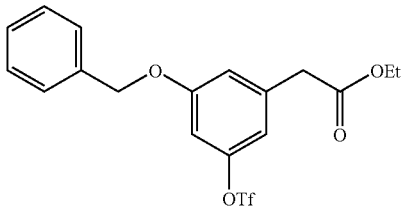 [SMILES: CCOC(=O)Cc1cc(OCc2ccccc2)cc(OS(=O)(=O)C(F)(F)F)c1]

To a solution of 3-(benzyloxy-5-hydroxy-phenyl)-acetic acid ethyl ester (74.4 g, 0.26 mol) in dichloromethane (700 mL) was added pyridine (62.5 mL, 0.78 mol). The mixture was cooled to 0° C. To this cold solution was added trifluoromethanesulfonic anhydride (65.6 mL, 0.39 mol), over 1.5 h, maintaining the internal temperature below 5° C. and stirred for an additional 0.5 h at 0° C. This reaction mixture was poured to a mixture of 1 N HCl (420 mL), and wet-ice (105 g) and stirred for 0.5 h. The aqueous layer was extracted with dichloromethane (2×100 mL). Combined fractions were washed with water (2×100 mL), saturated aqueous NaHCO$_3$ solution (2×100 mL), and brine (2×100 mL). The organics were dried (MgSO$_4$) and concentrated in vacuo to receive a reddish liquid (108 g) which was carried on to the next step without further purification. Calcd for C18H17F3O6S (M+H) 419.07, Found 419.1.

d) (5-Benzyloxy-4'-trifluoromethyl-biphenyl-3-yl)-acetic acid ethyl ester

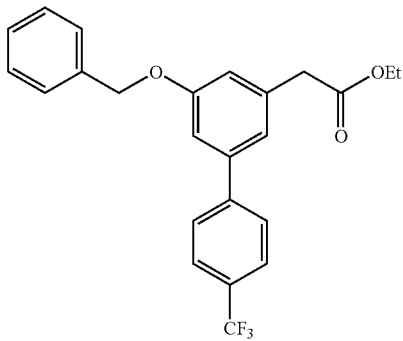 [SMILES: CCOC(=O)Cc1cc(OCc2ccccc2)cc(-c2ccc(C(F)(F)F)cc2)c1]

A mixture of (3-benzyloxy-5-trifluoromethanesulfonyloxy-phenyl)-acetic acid ethyl ester (108 g, 0.26 mol), 4-(trifluoromethyl)phenylboronic acid (55.6 g, 0.29 mol), 1,2-dimethoxyethane (1.1 L) and aqueous Na$_2$CO$_3$ (2 M, 129 mL, 0.26 mol) was mechanically stirred while purging with N$_2$ at room temperature for 10 min. To this system was added Pd(Ph$_3$)$_4$ (480 mg, 0.42 mmol) and heated to reflux (95° C.) for 2.5 h. The red-brown mixture was diluted with EtOAc (0.5 L) and washed with saturated aqueous NaHCO$_3$ solution (3×200 mL) and brine (2×200 mL). The organic fraction was dried (Na$_2$SO$_4$) and concentrated in vacuo. The crude mixture was purified by ISCO column chromatography to obtain (5-benzyloxy-4'-trifluoromethyl-biphenyl-3-yl)-acetic acid ethyl ester (107 g, 100%).
$^1$H-NMR (CDCl$_3$): δ 1.26 (t, 3H), 3.66 (s, 2H), 4.17 (q, 2H), 5.12 (s, 2H), 6.99 (s, 1H), 7.12 (s, 2H), 7.34-7.49 (m, 5H), 7.67 (s, 4H); Calcd for C24H21F3O3 (M+H) 415.14, Found 415.2.

e) 2-(5-Benzyloxy-4'-trifluoromethyl-biphenyl-3-yl)-4-methyl-pent-4-enoic acid ethyl ester

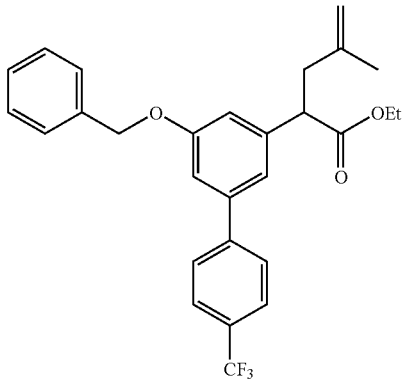 [SMILES: C=C(C)CC(C(=O)OCC)c1cc(OCc2ccccc2)cc(-c2ccc(C(F)(F)F)cc2)c1]

To a solution of compound 1d (4.9 g, 11.8 mmol) in THF (50 mL) at −78° C. was added Li[N(SiMe$_3$)$_2$] (1N in THF, 14.2 mL, 14.2 mmol) dropwise. The reaction mixture was stirred for 1 h at −78° C. and then 3-bromo-2-methyl-propene (1.25 mL, 12.4 mmol) was added dropwise. The solution was slowly warmed up to −35° C. and stirred at −35° C. for 0.5 h. The reaction was quenched with NH$_4$Cl saturated solution and extracted with EtOAc. The organic extracts was dried (Na$_2$SO$_4$), concentrated and purified by column chromatography give compound 1e (5.1 g, 92%) as a clear oil; $^1$H NMR (400 MHz, CHLOROFORM-D) δ ppm 1.19-1.29 (m, 3 H), 1.74 (s, 3 H), 2.47 (m, 1 H), 2.85 (m, 1 H), 3.83 (m, 1 H), 4.11 (m, 2 H), 4.72 (s, 1 H), 4.77 (s, 1 H), 5.12 (s, 2 H), 7.03 (s, 1 H), 7.10 (s, 1 H), 7.15 (s, 1 H), 7.35-7.48 (m, 5 H), 7.67 (s, 4 H); Calcd for C28H27F3O3 (M+H) 469.19, Found 469.

f) 2-(5-Hydroxy-4'-trifluoromethyl-biphenyl-3-yl)-4-methyl-pentanoic acid ethyl ester

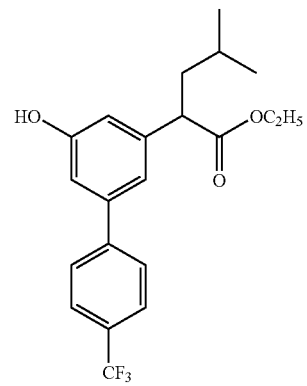 [SMILES: CCOC(=O)C(CC(C)C)c1cc(O)cc(-c2ccc(C(F)(F)F)cc2)c1]

A mixture of compound 1e (5.1 g, 10.9 mmol), 10% Pd/C (500 mg) in EtOH (50 mL) was hydrogenated under H$_2$ (40 psi) in par-shaker for 20 h. The resulting reaction mixture was filtered through a celite pad and the filtrate was concentrated to give the title compound (4.2 g, 100%) as a clear oil; 1H NMR (300 MHz, CHLOROFORM-D) δ ppm 0.92 (d, J=6.6 Hz, 6 H), 1.25 (m, 3 H), 1.49-1.61 (m, 1 H), 1.65-1.70 (m, 1 H), 1.95-2.05 (m, 1 H), 3.67 (t, J=7.7 Hz, 1 H), 4.10-4.29 (m, 2 H), 6.91 (s, 1 H), 6.97 (t, J=2.0 Hz, 1 H), 7.08 (s, 1 H), 7.65 (s, 4 H); Calcd for C21H23F3O3 (M+H) 381.16, Found 381.

g) 4-Methyl-2-(5-trifluoromethanesulfonyloxy-4'-trifluoromethyl-biphenyl-3-yl)-pentanoic acid ethyl ester

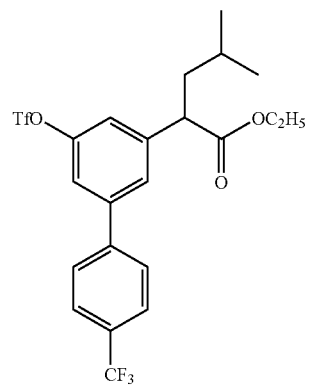 [SMILES: CCOC(=O)C(CC(C)C)c1cc(OS(=O)(=O)C(F)(F)F)cc(-c2ccc(C(F)(F)F)cc2)c1]

To a solution of compound 1f, 2-(5-Hydroxy-4'-trifluoromethyl-biphenyl-3-yl)-4-methyl-pentanoic acid ethyl ester, 2.8 g, 7.36 mmol) and N-phenyl-bis-(trifluoromethanesulfonimide) (3.16 g, 8.83 mmol) in THF (30 mL) under N₂ was added Et₃N (2.05 mL, 14.7 mmol). The reaction mixture was heated to reflux overnight. After cooling to room temperature, the solution was concentrated and purified by column chromatography to give the title compound (3.7 g, 98%) as a colorless thick oil; ¹H NMR (400 MHz, CHLOROFORM-D) δ ppm 0.94 (dd, J=6.60, 1.47 Hz, 6 H), 1.22-1.28 (m, 3 H), 1.46-1.52 (m, 1 H), 1.69 (ddd, J=13.82, 7.09, 6.97 Hz, 1 H), 1.98-2.06 (m, 1 H), 3.75 (t, J=7.83 Hz, 1 H), 4.10-4.21 (m, 2 H), 7.31 (s, 1 H), 7.38 (s, 1 H), 7.57 (s, 1 H), 7.65-7.75 (m, 4 H); Calcd for C22H22F6O5S (M+H) 513.11, Found 513.

h) 2-[5-(3,5-Dichloro-benzoyl)-4'-trifluoromethyl-biphenyl-3-yl]-4-methyl-pentanoic acid ethyl ester

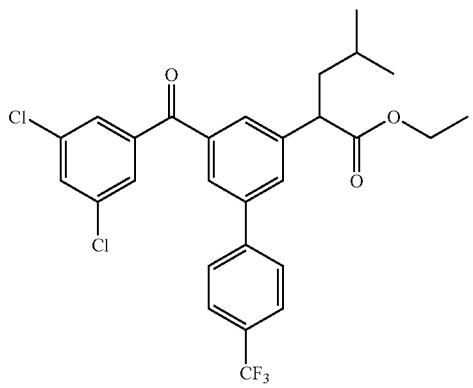 [SMILES: CCOC(=O)C(CC(C)C)c1cc(C(=O)c2cc(Cl)cc(Cl)c2)cc(-c2ccc(C(F)(F)F)cc2)c1]

A mixture of compound 1g (100 mg, 0.195 mmol), 3,5-dichloro-phenyl-boronic acid (63 mg, 0.33 mmol), Pd(dppf)₂Cl₂ (14.3 mg, 0.020 mmol), K₂CO₃ (81 mg, 0.585 mmol) and KI (97 mg, 0.585 mmol) in anisole (2 mL) at 85° C. under a CO atmosphere using a balloon filled with CO gas was heated for 24 h. After cooling to room temperature, the solution was partitioned between EtOAc and H₂O. The organic layer was dried (Na₂SO₄), concentrated and purified by column chromatography to give an ethyl ester intermediate.

i) 2-[5-(3,5-Dichloro-benzoyl)-4'-trifluoromethyl-biphenyl-3-yl]-4-methyl-pentanoic acid A mixture of the above intermediate and NaOH (2N in H₂O, 0.147 mL, 0.294 mmol) in THF-MeOH (0.6 mL-0.6 mL) was stirred for 18 h and concentrated. CH₂Cl₂ and water were added, and the mixture was acidified with 1N HCl. The organic phase was separated and the aqueous phase was extracted with CH₂Cl₂. The combined organic layers were dried, concentrated, and purified by column chromatography to give 45 mg (45%, 2 steps) of compound h as a white solid; ¹H NMR (400 MHz, MeOD) δ 0.96 (dd, J=6.60, 1.47 Hz, 6 H), 1.53 (ddd, J=13.57, 6.72, 6.60 Hz, 1 H), 1.77 (ddd, J=13.82, 7.70, 6.36 Hz, 1 H), 2.00 (dt, J=13.51, 7.67 Hz, 1 H), 3.88 (t, J=7.83 Hz, 1 H), 7.71-7.80 (m, 6 H), 7.83-7.88 (m, 2H), 7.95-7.98 (m, 2 H); Calcd for C26H21Cl2F3O3 (M+H) 509.08, Found 509.1.

Example 2

2-[5-(3,5-Dichloro-benzyl)-4'-trifluoromethyl-biphenyl-3-yl]-4-methyl-pentanoic acid

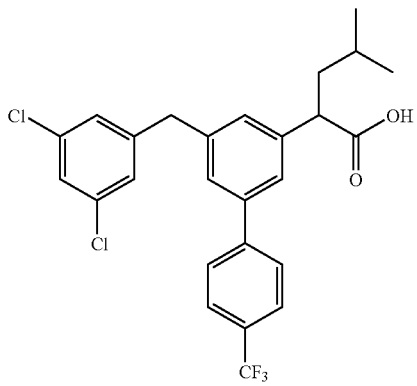 [SMILES: CC(C)CC(C(=O)O)c1cc(Cc2cc(Cl)cc(Cl)c2)cc(-c2ccc(C(F)(F)F)cc2)c1]

A mixture of compound 1g (50 mg, 0.098 mmol), 3,5-dichloro-benzyl zinc chloride (0.5M in THF, 0.588 mL, 0.294 mmol) and Pd(dppf)₂Cl₂ (7.2 mg, 0.0098 mmol) in THF (1.5 mL) was degassed with N₂ for 6 min and heated at 120° C. under microwave irradiation (300 W, 250 psi) for 20 min. After cooling to room temperature, the solution was partitioned between EtOAc and NH₄Cl saturated solution. The organic layer was dried (Na₂SO₄), concentrated and purified by column chromatography to give an ethyl ester intermediate.

The above ester intermediate was hydrolyzed following the same hydrolysis procedure of Example 1, step (2) to give the title compound; 1H NMR (400 MHz, MeOD) δ ppm 0.84 (dd, J=6.48, 3.30 Hz, 6 H), 1.39 (ddd, J=13.57, 6.72, 6.60 Hz, 1 H), 1.58-1.65 (m, 1 H), 1.83-1.91 (m, 1 H), 3.65 (t, J=7.83 Hz, 1 H), 3.97 (s, 2 H), 7.12 (d, J=1.71 Hz, 2 H), 7.16-7.19 (m, 2 H), 7.36 (s, 1 H), 7.43 (s, 1 H), 7.63-7.71 (m, 4 H); Calcd for C26H23Cl2F3O2 (M+Na) 517.1, Found 517.0.

Example 3

2-[5-(2,4-Difluoro-benzyl)-4'-trifluoromethyl-biphenyl-3-yl]-4-methyl-pentanoic acid

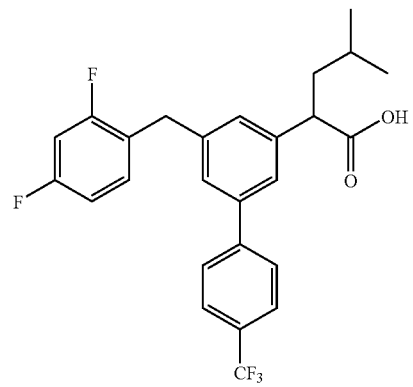 [SMILES: CC(C)CC(C(=O)O)c1cc(Cc2ccc(F)cc2F)cc(-c2ccc(C(F)(F)F)cc2)c1]

The title compound was prepared from a Nigishi coupling of 4-methyl-2-(5-trifluoromethyl-biphenyl-3-yl)pentanoic acid (intermediate compound 1g) with 2,4-difluoro-benzyl zinc chloride under the conditions described in Example 2; 1H NMR (400 MHz, MeOD) δ ppm 0.75-0.85 (m, 6 H), 1.37 (dt, J=13.39, 6.63 Hz, 1 H), 1.54 (ddd, J=13.69, 7.21, 6.97 Hz, 1 H), 1.85 (ddd, J=13.51, 7.52, 7.34 Hz, 1 H), 3.60 (t, J=7.83 Hz, 1 H), 3.92 (s, 2 H), 6.73-6.84 (m, 2 H), 7.12-7.19 (m, 2 H), 7.29 (s, 1 H), 7.37 (s, 1 H), 7.58-7.66 (m, 4 H); Calcd for C26H23F5O2 (M+Na) 485.16, Found 485.1.

Example 4

2-[5-(4-Chloro-pyridin-3-ylmethyl)-4'-trifluoromethyl-biphenyl-3-yl]-4-methyl-pentanoic acid

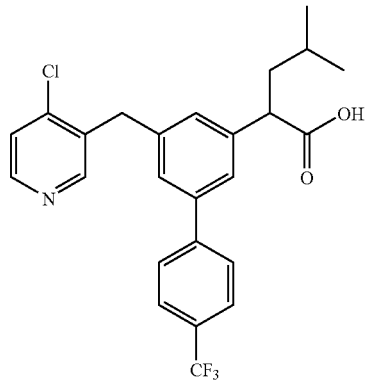 [SMILES: CC(C)CC(C(=O)O)c1cc(Cc2cnccc2Cl)cc(-c2ccc(C(F)(F)F)cc2)c1]

The title compound was prepared from a Nigishi coupling of 4-methyl-2-(5-trifluoromethyl-biphenyl-3-yl)pentanoic acid (intermediate compound 1g) with 4-chloro-pyridyl-3-methyl zinc chloride under the conditions described in Example 2; 1H NMR (400 MHz, MeOD) δ ppm 0.83 (td, J=7.34, 1.96 Hz, 6 H), 1.40 (ddd, J=13.33, 6.60, 6.48 Hz, 1 H), 1.49-1.57 (m, 1 H), 1.87 (ddd, J=13.27, 8.50, 7.09 Hz, 1 H), 3.55-3.61 (m, 1 H), 3.99 (s, 2 H), 7.19 (s, 1 H), 7.26-7.33 (m, 2 H), 7.44 (s, 1 H), 7.58-7.70 (m, 5 H) 8.20 (d, J=2.20 Hz, 1 H); Calcd for C25H23ClF3NO2 (M+H) 462.14, Found 462.1.

Example 5

4-Methyl-2-[4'-trifluoromethyl-5-(3-trifluoromethyl-benzyl)-biphenyl-3-yl]-pentanoic acid

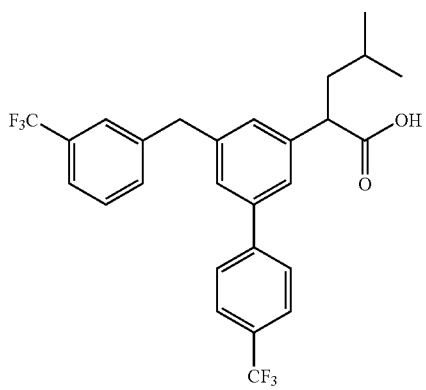 [SMILES: CC(C)CC(C(=O)O)c1cc(Cc2cccc(C(F)(F)F)c2)cc(-c2ccc(C(F)(F)F)cc2)c1]

The title compound was prepared from a Nigishi coupling of 4-methyl-2-(5-trifluoromethyl-biphenyl-3-yl)pentanoic acid (intermediate compound 1g) with 3-trifluoromethylbenzyl zinc chloride under the conditions described in Example 2; 1H NMR (400 MHz, MeOD) δ ppm 0.76-0.86 (m, 6 H), 1.36 (dt, J=13.51, 6.82 Hz, 1 H), 1.54-1.62 (m, 1 H), 1.80-1.91 (m, 1 H), 3.62 (t, J=7.83 Hz, 1 H), 4.05 (s, 2 H), 7.16 (s, 1 H), 7.33-7.44 (m, 6 H), 7.64 (q, J=8.56 Hz, 4 H); Calcd for C27H24F6O2 (M+Na) 517.17, Found 517.2.

Example 6

2-[5-(3,5-Difluoro-benzyl)-4'-trifluoromethyl-biphenyl-3-yl]-4-methyl-pentanoic acid

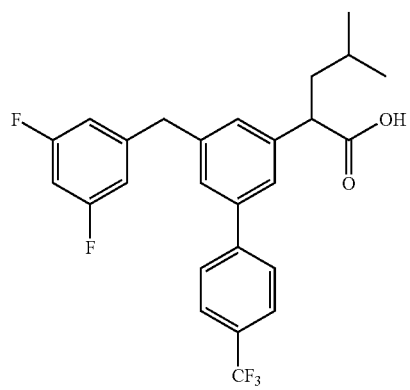 [SMILES: CC(C)CC(C(=O)O)c1cc(Cc2cc(F)cc(F)c2)cc(-c2ccc(C(F)(F)F)cc2)c1]

The title compound was prepared from a Nigishi coupling of 4-methyl-2-(5-trifluoromethyl-biphenyl-3-yl)pentanoic acid (intermediate compound 1g) with 3,5-difluorobenzyl zinc chloride under the conditions described in Example 2; 1H NMR (400 MHz, MeOD) δ ppm 0.83 (dd, J=6.60, 3.18 Hz, 6 H), 1.37-1.41 (m, 1 H), 1.55-1.62 (m, 1 H), 1.86 (dd, J=7.70, 5.99 Hz, 1 H), 3.63 (t, J=7.70 Hz, 1 H), 3.97 (s, 2 H), 6.64-6.67 (m, 1 H), 6.75 (dd, J=8.56, 2.20 Hz, 2 H), 7.17 (s, 1 H), 7.34 (s, 1 H), 7.41-7.42 (m, 1 H), 7.62-7.65 (m, 2 H), 7.67-7.70 (m, 2 H); Calcd for C26H23F5O2 (M+H) 463.16, Found 463.3.

Example 7

2-[5-(3,5-Difluoro-benzoyl)-4'-trifluoromethyl-biphenyl-3-yl]-4-methyl-pentanoic acid

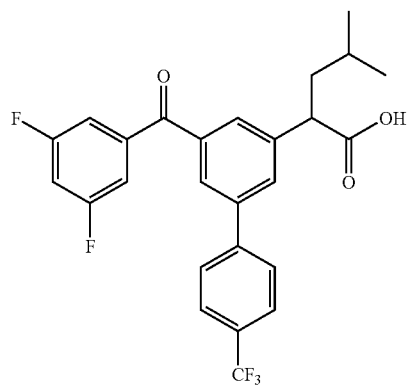 [SMILES: CC(C)CC(C(=O)O)c1cc(C(=O)c2cc(F)cc(F)c2)cc(-c2ccc(C(F)(F)F)cc2)c1]

The title compound was prepared from a Nigishi coupling of 4-methyl-2-(5-trifluoromethyl-biphenyl-3-yl)pentanoic acid (intermediate compound 1g) with 3,5-difluorophenylboronic acid under the conditions described in Example 1; 1H NMR (400 MHz, MeOD) δ ppm 0.96 (dd, J=6.60, 1.71 Hz, 6 H), 1.53 (dt, J=13.51, 6.82 Hz, 1 H), 1.69-1.79 (m, 1 H), 1.96-2.05 (m, 1 H), 3.88 (t, J=7.83 Hz, 1 H), 7.26-7.32 (m, 1 H), 7.39 (ddd, J=12.35, 4.65, 2.32 Hz, 2 H), 7.76-7.86 (m, 5 H), 7.92-8.00 (m, 2 H); Calcd for C26H21F5O3 (M+Na) 499.14, Found 499.0.

Example 8

2-[5-(4-Cyano-benzoyl)-4'-trifluoromethyl-biphenyl-3-yl]-4-methyl-pentanoic acid

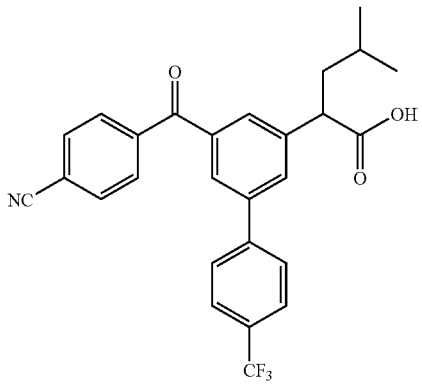

The title compound was prepared from a Nigishi coupling of 4-methyl-2-(5-trifluoromethyl-biphenyl-3-yl)pentanoic acid (intermediate compound 1g) with 4-cyanophenylboronic acid under the conditions described in Example 1; 1H NMR (400 MHz, MeOD) δ ppm 0.96 (dd, J=6.60, 1.47 Hz, 6 H), 1.50-1.57 (m, 1 H), 1.74 (dd, J=13.82, 6.97 Hz, 1 H), 2.02 (dd, J=7.58, 5.87 Hz, 1 H), 3.88 (t, J=7.83 Hz, 1 H), 7.76-7.87 (m, 5 H), 7.91-7.97 (m, 6 H); Calcd for C27H22F3NO3 (M+H) 466.16, Found 466.2.

Example 9

2-{5-[(3,5-Difluoro-phenyl)-hydroxy-methyl]-4'-trifluoromethyl-biphenyl-3-yl}-4-methyl-pentanoic acid

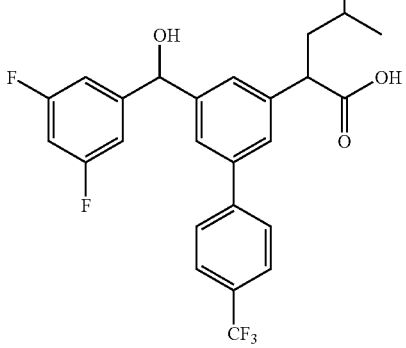

a) 2-{5-[(3,5-Difluoro-phenyl)-hydroxy-methyl]-4'-trifluoromethyl-biphenyl-3-yl}-4-methyl-pentanoic acid ethyl ester

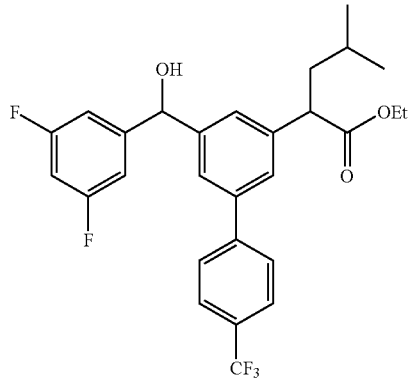 [SMILES: CCOC(=O)C(CC(C)C)c1cc(-c2ccc(C(F)(F)F)cc2)cc(C(O)c2cc(F)cc(F)c2)c1]

Replacing 3,5-dichlorophenylboronic acid with 3,5-difluorophenylboronic acid following the same Suzuki-coupling procedure as in the preparation of compound 1h gave an ester intermediate.

To a solution of the above intermediate (10 mg, 0.02 mmol) in THF-EtOH (0.5 mL-0.5 mL) was added NaBH4 (11 mg, 0.03 mmol). The reaction mixture was stirred at room temperature for 4 h and concentrated. The residue was purified by preparative TLC to get compound 9a; 1H NMR (400 MHz, CHLOROFORM-D) δ ppm 0.77-0.87 (m, 6 H), 1.14 (t, J=7.21 Hz, 3 H), 1.36-1.46 (m, 1 H), 1.60 (dt, J=13.76, 6.94 Hz, 1 H), 1.94 (dt, J=13.69, 7.70 Hz, 1 H), 2.40 (dd, J=6.36, 3.42 Hz, 1 H), 3.64 (t, J=7.83 Hz, 1 H), 3.99-4.11 (m, 2 H), 5.78 (d, J=2.20 Hz, 1 H), 6.63 (tt, J=8.80, 2.32 Hz, 1 H), 6.84-6.90 (m, 2 H), 7.29 (s, 1 H), 7.38 (s, 1 H), 7.42 (s, 1 H), 7.56-7.65 (m, 4 H); Calcd for C28H27F5O3 (M+Na) 529.19, Found 529.2.

b) 2-{5-[(3,5-Difluoro-phenyl)-hydroxy-methyl]-4'-trifluoromethyl-biphenyl-3-yl}-4-methyl-pentanoic acid

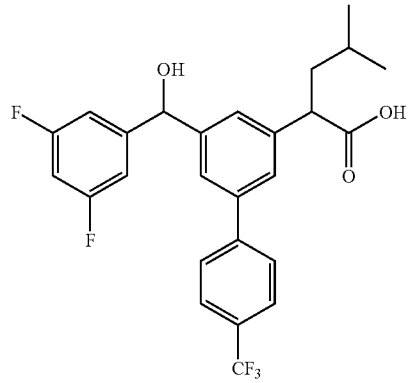

The above intermediate was hydrolyzed following the same hydrolyzation procedure as in Example 1 to give the title compound; 1H NMR (400 MHz, MeOD) δ ppm 0.85-0.94 (m, 6 H), 1.47 (dt, J=13.45, 6.72 Hz, 1 H), 1.68 (ddd, J=13.69, 7.21, 6.97 Hz, 1 H), 1.92-2.02 (m, 1 H), 3.75 (t, J=7.83 Hz, 1

H), 5.84 (s, 1 H), 6.79 (tt, J=9.05, 2.20 Hz, 1 H), 6.99-7.05 (m, 2 H), 7.42 (s, 1 H), 7.57 (d, J=17.12 Hz, 2 H), 7.72-7.80 (m, 4 H).

Example 10

2-[5-(3,5-Difluoro-phenylethynyl)-4'-trifluoromethyl-biphenyl-3-yl]-4-methyl-pentanoic acid

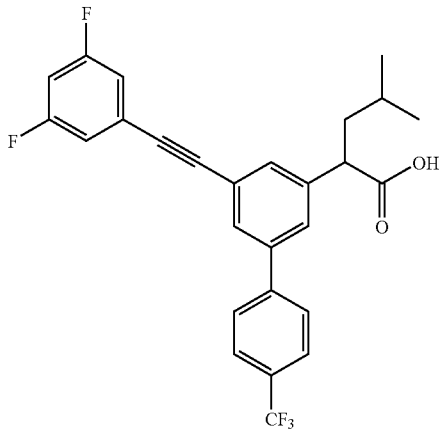 [SMILES: CC(C)CC(C(=O)O)c1cc(C#Cc2cc(F)cc(F)c2)cc(-c2ccc(C(F)(F)F)cc2)c1]

A mixture of compound 1g (50 mg, 0.098 mmol) and Pd(PPh₃)₂Cl₂ (6.9 mg, 0.0098 mmol) in Et₂NH (2 mL) was stirred under N₂ for 20 min and CuI (1 mg, 0.0049 mmol) was added. After stirring for 20 min, 1-ethynyl-3,5-difluoro-benzene (40 mg, 0.29 mmol) was added. The reaction mixture was heated at 85° C. for 24 h. After cooling to room temperature, the solution was partitioned between EtOAc and H₂O. The organic layer was dried (Na₂SO₄), concentrated and purified by preparative TLC to give an ethyl ester intermediate.

The above intermediate was hydrolyzed following the same hydrolyzation procedure as in Example 1 to give the title compound; 1H NMR (400 MHz, MeOD) δ ppm 0.77-0.88 (m, 6 H), 1.43 (dt, J=13.45, 6.72 Hz, 1 H), 1.62 (ddd, J=13.82, 7.09, 6.97 Hz, 1 H), 1.92 (dt, J=13.63, 7.61 Hz, 1 H), 3.69 (t, J=7.83 Hz, 1 H), 6.86-6.95 (m, 1 H), 7.02-7.11 (m, 2 H), 7.48 (s, 1 H), 7.58 (t, J=1.71 Hz, 1 H), 7.65-7.74 (m, 5 H).

Example 11

4-Methyl-2-[4'-trifluoromethyl-5-(4-trifluoromethyl-phenylethynyl)-biphenyl-3-yl]-pentanoic acid

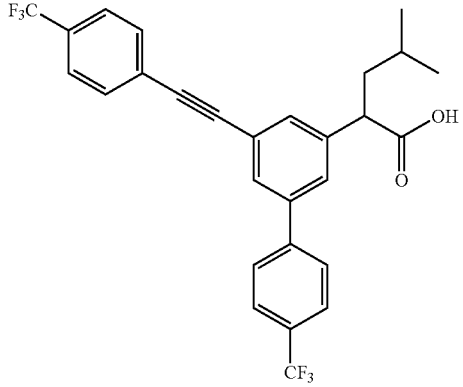 [SMILES: CC(C)CC(C(=O)O)c1cc(C#Cc2ccc(C(F)(F)F)cc2)cc(-c2ccc(C(F)(F)F)cc2)c1]

The title compound was prepared from a Sonogashira coupling of 4-methyl-2-(5-trifluoromethyl-biphenyl-3-yl)pentanoic acid (intermediate compound 1g) with 1-ethynyl-4-trifluoromethyl-benzene under the conditions described in Example 10; 1H NMR (400 MHz, MeOD) δ ppm 0.86 (dd, J=6.60, 1.96 Hz, 6 H), 1.44 (dt, J=13.45, 6.72 Hz, 1 H), 1.62 (ddd, J=13.82, 7.09, 6.97 Hz, 1 H), 1.87-1.97 (m, 1 H), 3.70 (t, J=7.83 Hz, 1 H), 7.49 (d, J=1.47 Hz, 1 H), 7.57-7.73 (m, 9 H).

Example 12

2-[5-(4-Chloro-phenylethynyl)-4'-trifluoromethyl-biphenyl-3-yl]-4-methyl-pentanoic acid

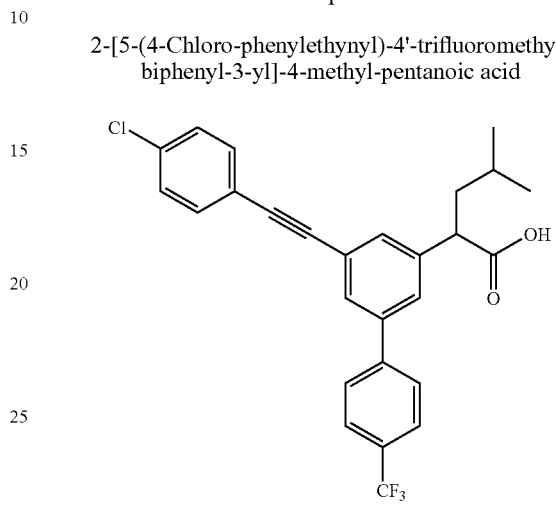

The title compound was prepared from a Sonogashira coupling of 4-methyl-2-(5-trifluoromethyl-biphenyl-3-yl)pentanoic acid (intermediate compound 1g) with 1-ethynyl-4-chloro-benzene under the conditions described in Example 10; 1H NMR (400 MHz, MeOD) δ ppm 0.77-0.87 (m, 6 H), 1.43 (dt, J=13.39, 6.63 Hz, 1 H), 1.61 (ddd, J=13.63, 7.09, 6.91 Hz, 1 H), 1.91 (dt, J=13.51, 7.67 Hz, 1 H), 3.68 (t, J=7.83 Hz, 1 H), 7.23-7.30 (m, 2 H), 7.37-7.46 (m, 3 H), 7.54 (t, J=1.71 Hz, 1 H), 7.60 (t, J=1.47 Hz, 1 H), 7.62-7.71 (m, 4 H).

Example 13

2-[5-(3,5-Bis-trifluoromethyl-phenylethynyl)-4'-trifluoromethyl-biphenyl-3-yl]-4-methyl-pentanoic acid

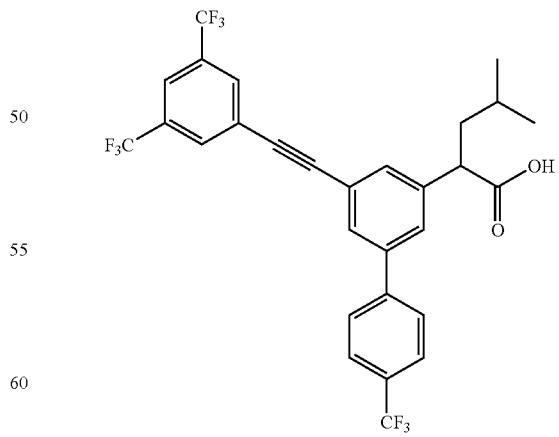

The title compound was prepared from a Sonogashira coupling of 4-methyl-2-(5-trifluoromethyl-biphenyl-3-yl)pentanoic acid (intermediate compound 1g) with 3,5-bis(trifluoromethyl)-benzene under the conditions described in Example 10; 1H NMR (400 MHz, MeOD) δ ppm 0.89-0.99 (m, 6 H), 1.53 (dt, J=13.51, 6.82 Hz, 1 H), 1.73 (ddd, J=13.76, 7.34, 7.03 Hz, 1 H), 2.02 (ddd, J=13.57, 7.83, 7.70 Hz, 1 H), 3.81 (t, J=7.70 Hz, 1 H), 7.64 (s, 1 H), 7.70-7.86 (m, 6 H), 7.94-8.02 (m, 1 H), 8.15 (s, 2 H).

Example 14

2-[5-(2-Biphenyl-4-yl-vinyl)-4'-trifluoromethyl-biphenyl-3-yl]-4-methyl-pentanoic acid

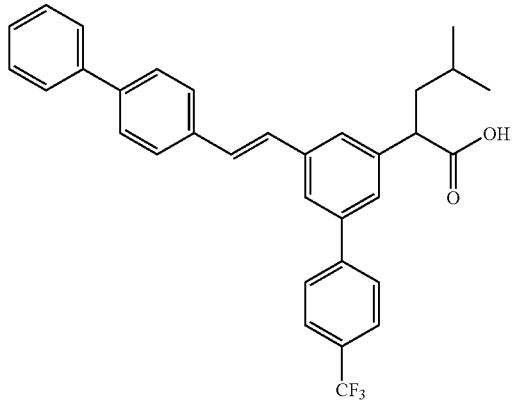 [SMILES: CC(C)CC(C(=O)O)c1cc(/C=C/c2ccc(-c3ccccc3)cc2)cc(-c2ccc(C(F)(F)F)cc2)c1]

A mixture of compound 1 g (60 mg, 0.117 mmol), trans-2-(4-biphenyl)-vinyl-boronic acid (45 mg, 0.199 mmol), Pd(dppf)$_2$Cl$_2$ (10 mg, 0.0117 mmol) and K$_2$CO$_3$ (32.3 mg, 0.234 mmol) in 1,4-dioxane-water (0.8 mL-0.8 mL) was heated to 85° C. for 15 h. After cooling to room temperature, the solution was partitioned between EtOAc and H$_2$O. The organic layer was dried (Na$_2$SO$_4$), concentrated and purified by column chromatography to give an ethyl ester intermediate.

The above ester intermediate was hydrolyzed following the same hydrolysis procedure of Example 1, step (2) to give the title compound; $^1$H NMR (400 MHz, MeOD) δ 0.88-0.99 (m, 6 H), 1.57 (dt, J=13.39, 6.63 Hz, 1 H), 1.74 (ddd, J=13.82, 7.09, 6.97 Hz, 1 H), 1.98-2.09 (m, 2 H), 3.80 (t, J=7.70 Hz, 1 H), 7.26-7.34 (m, 3 H), 7.42 (t, J=7.58 Hz, 2 H), 7.52 (s, 1 H), 7.57-7.65 (m, 7 H), 7.74 (d, J=9.05 Hz, 3 H), 7.78-7.84 (m, 2 H); Calcd for C33H29F3O2 (M+H) 515.21, Found 515.2.

Example 15

4-Methyl-2-{4'-trifluoromethyl-5-[2-(4-trifluoromethyl-phenyl)-vinyl]-biphenyl-3-yl}-pentanoic acid

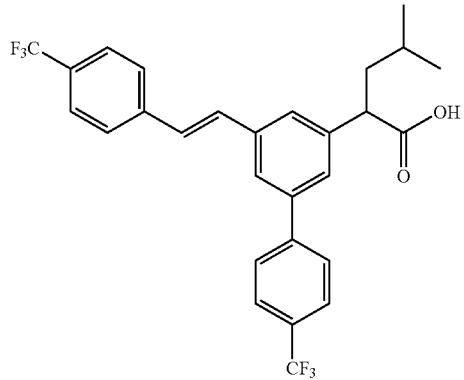 [SMILES: CC(C)CC(C(=O)O)c1cc(/C=C/c2ccc(C(F)(F)F)cc2)cc(-c2ccc(C(F)(F)F)cc2)c1]

The title compound was prepared from a Nigishi coupling of 4-methyl-2-(5-trifluoromethyl-biphenyl-3-yl)pentanoic acid (intermediate compound 1g) with trans-2-(4-trifluoromethylphenyl)-vinyl-boronic acid under the conditions described in Example 14; 1H NMR (400 MHz, MeOD) δ ppm 0.78-0.89 (m, 6 H), 1.47 (dt, J=13.39, 6.63 Hz, 1 H), 1.62 (ddd, J=13.63, 7.09, 6.91 Hz, 1 H), 1.91-1.98 (m, 1 H), 3.68 (t, J=7.83 Hz, 1 H), 7.33 (d, J=16.4 Hz, 1 H), 7.26 (d, J=16.5 Hz, 1 H), 7.48-7.58 (m, 4 H), 7.64-7.70 (m, 5 H), 7.75-7.78 (m, 2 H).

Example 16

4-Methyl-2-[5-(2-p-tolyl-vinyl)-4'-trifluoromethyl-biphenyl-3-yl]-pentanoic acid

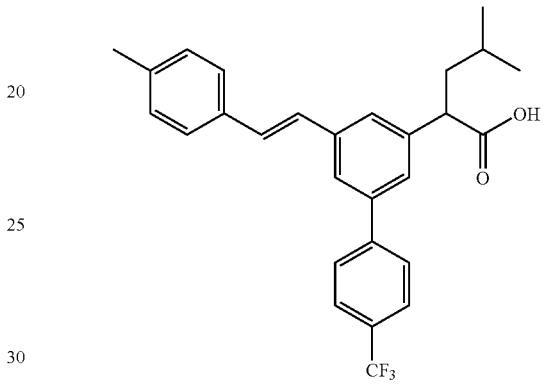

The title compound was prepared from a Nigishi coupling of 4-methyl-2-(5-trifluoromethyl-biphenyl-3-yl)pentanoic acid (intermediate compound 1g) with trans-2-(4-methylphenyl)-vinyl-boronic acid under the conditions described in Example 14; 1H NMR (400 MHz, MeOD) δ ppm 0.87 (dd, J=6.60, 3.18 Hz, 6 H), 1.46 (dt, J=13.39, 6.63 Hz, 1 H), 1.63 (ddd, J=13.63, 7.09, 6.91 Hz, 1 H), 1.88-1.97 (m, 1 H), 2.23 (s, 3 H), 3.68 (t, J=7.83 Hz, 1 H), 7.03-7.12 (m, 4 H), 7.35-7.39 (m, 3 H), 7.46 (s, 1 H), 7.62 (d, J=11.49 Hz, 2 H), 7.66 (s, 1 H), 7.69-7.79 (m, 2 H); Calcd for C28H27F3O2 (M+H) 453.20, Found 453.1.

Example 17

2-{5-[2-(4-Chloro-phenyl)-vinyl]-4'-trifluoromethyl-biphenyl-3-yl}-4-methyl-pentanoic acid

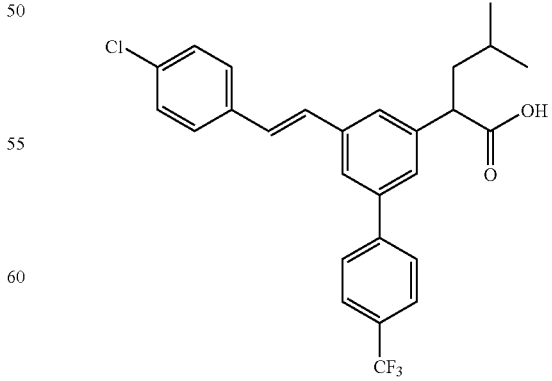

The title compound was prepared from a Nigishi coupling of 4-methyl-2-(5-trifluoromethyl-biphenyl-3-yl)pentanoic acid (intermediate compound 1g) with trans-2-(4-chlorophenyl)-vinyl-boronic acid under the conditions described in Example 14; 1H NMR (300 MHz, MeOD) δ ppm 0.79 (dd, J=6.41, 2.64 Hz, 6 H), 1.25-1.37 (m, 1 H), 1.45 (ddd, J=13.47, 7.16, 6.88 Hz, 1 H), 1.67-1.77 (m, 1 H), 3.51 (t, J=7.72 Hz, 1 H), 6.56-6.65 (m, 2 H), 7.09-7.18 (m, 5 H), 7.34 (d, J=18.09 Hz, 2 H), 7.54-7.63 (m, 4 H); Calcd for C27H24ClF3O2 (M+Na) 495.14, Found 495.3.

Example 18

2-{5-[2-(4-Fluoro-phenyl)-vinyl]-4'-trifluoromethyl-biphenyl-3-yl}-4-methyl-pentanoic acid

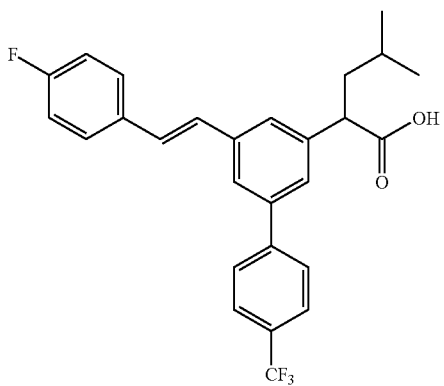 [SMILES: CC(C)CC(C(=O)O)c1cc(/C=C/c2ccc(F)cc2)cc(-c2ccc(C(F)(F)F)cc2)c1]

The title compound was prepared from a Nigishi coupling of 4-methyl-2-(5-trifluoromethyl-biphenyl-3-yl)pentanoic acid (intermediate compound 1g) with trans-2-(4-chlorophenyl)-vinyl-boronic acid under the conditions described in Example 14; 1H NMR (400 MHz, CHLOROFORM-D) δ ppm 0.95 (d, J=6.60 Hz, 6 H), 1.57 (ddd, J=13.33, 6.85, 6.72 Hz, 1 H), 1.76 (ddd, J=13.82, 7.09, 6.97 Hz, 1 H), 2.00-2.10 (m, 1 H), 3.78 (t, J=7.70 Hz, 1 H), 7.03-7.13 (m, 4 H), 7.43-7.54 (m, 4 H), 7.60 (s, 1 H), 7.70 (s, 4 H).

Example 19

2-{5-[2-(3,5-Difluoro-phenyl)-vinyl]-4'-trifluoromethyl-biphenyl-3-yl}-4-methyl-pentanoic acid

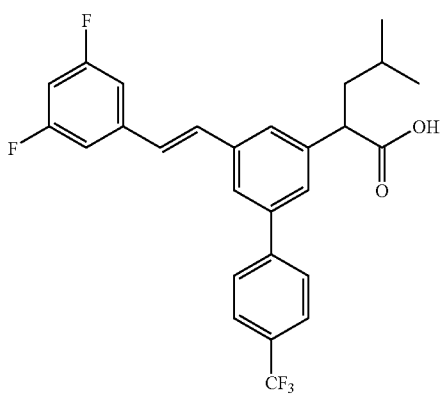 [SMILES: CC(C)CC(C(=O)O)c1cc(/C=C/c2cc(F)cc(F)c2)cc(-c2ccc(C(F)(F)F)cc2)c1]

The title compound was prepared from a Nigishi coupling of 4-methyl-2-(5-trifluoromethyl-biphenyl-3-yl)pentanoic acid (intermediate compound 1g) with trans-2-(3,5-difluorophenyl)-vinyl-boronic acid under the conditions described in Example 14; 1H NMR (400 MHz, MeOD) δ ppm 0.83-0.90 (m, 6 H), 1.45 (dt, J=13.27, 6.69 Hz, 1 H), 1.64 (ddd, J=13.69, 7.21, 6.97 Hz, 1 H), 1.90-1.98 (m, 1 H), 3.70 (t, J=7.83 Hz, 1 H), 6.70-6.76 (m, 1 H), 7.09-7.15 (m, 2 H), 7.20 (d, J=15.90 Hz, 2 H), 7.46-7.54 (m, 2 H), 7.65 (s, 1 H), 7.67 (d, J=1.22 Hz, 2 H), 7.71-7.77 (m, 2 H); Calcd for C27H23F5O2 (M+Na) 497.16, Found 497.1.

Example 20

2-{5-[2-(4-Methoxy-phenyl)-vinyl]-4'-trifluoromethyl-biphenyl-3-yl}-4-methyl-pentanoic acid

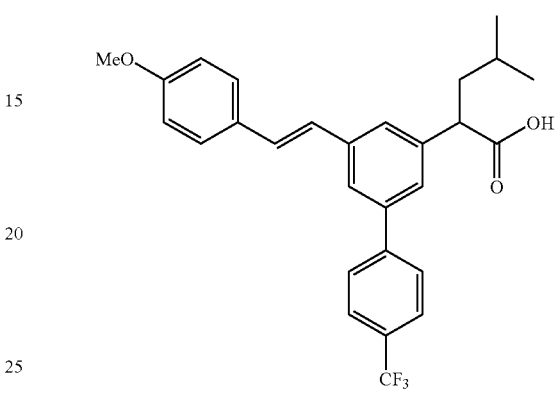

The title compound was prepared from a Nigishi coupling of 4-methyl-2-(5-trifluoromethyl-biphenyl-3-yl)pentanoic acid (intermediate Example 1g) with trans-2-(4-methoxyphenyl)-vinyl-boronic acid under the conditions described in Example 14; 1H NMR (400 MHz, MeOD) δ ppm 0.87 (dd, J=6.60, 3.18 Hz, 6 H), 1.46 (dt, J=13.21, 6.60 Hz, 1 H), 1.63 (ddd, J=13.82, 7.09, 6.97 Hz, 1 H), 1.87-1.98 (m, 1 H), 3.65-3.75 (m, 4 H), 6.81 (d, J=8.80 Hz, 2 H), 6.94-7.03 (m, 1 H), 7.07-7.17 (m, 1 H), 7.37-7.48 (m, 4 H), 7.58 (s, 1 H), 7.61-7.68 (m, 2 H), 7.72 (d, J=8.07 Hz, 2 H); Calcd for C28H27F3O3 (M+H) 469.19, Found 469.2.

Example 21

2-{5-[2-(4-Chloro-phenyl)-vinyl]-4'-trifluoromethyl-biphenyl-3-yl}-4-methyl-pentanoic acid

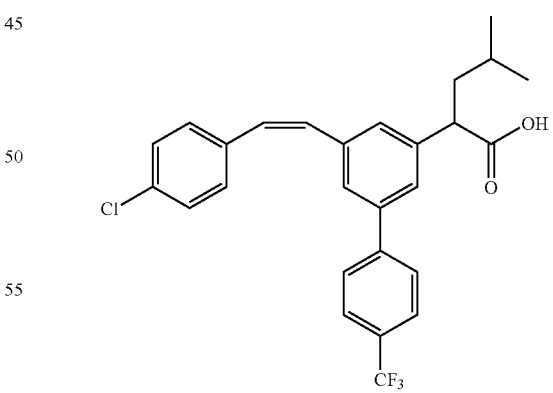

A mixture of compound 12 (20 mg, 0.042 mmole), 5% Pd/CaCO3 (2 mg), and EtOAc (5 mL) was hydrogenated under H2 (20 psi) in par-shaker for 9 h. The resulting reaction mixture was filtered through a celite pad, concentrated, and purified by HPLC to give the title compound (8 mg, 40%) as a white solid; 1H NMR (300 MHz, MeOD) δ ppm 0.79 (dd, J=6.41, 2.64 Hz, 6 H), 1.25-1.37 (m, 1 H), 1.45 (ddd, J=13.47, 7.16, 6.88 Hz, 1 H), 1.67-1.77 (m, 1 H), 3.51 (t, J=7.72 Hz, 1 H), 6.56-6.65 (m, 2 H), 7.09-7.18 (m, 5 H), 7.31 (s, 1 H), 7.37 (s, 1 H), 7.54-7.63 (m, 4 H); Calcd for C27H24ClF3O2 (M+Na) 495.14, Found 495.3.

Example 22

4-Methyl-2-{4'-trifluoromethyl-5-[2-(4-trifluoromethyl-phenyl)-vinyl]-biphenyl-3-yl}-pentanoic acid

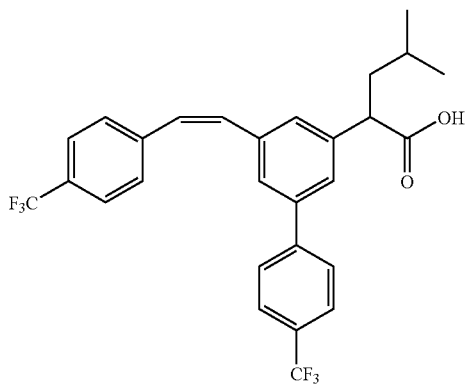 [SMILES: CC(C)CC(C(=O)O)c1cc(/C=C\c2ccc(C(F)(F)F)cc2)cc(-c2ccc(C(F)(F)F)cc2)c1]

A mixture of compound 11 (15 mg, 0.030 mmole), 5% Pd/CaCO₃ (1.5 mg), and MeOH (5 mL) was hydrogenated under H$_2$ (20 psi) in par-shaker for 4 h. The resulting reaction mixture was filtered through a celite pad, concentrated, and purified by HPLC to give the title compound (6 mg, 39%) as a white solid; 1H NMR (400 MHz, MeOD) δ ppm 0.76-0.84 (m, 6 H), 1.30-1.40 (m, 1 H), 1.41-1.51 (m, 1 H), 1.70-1.80 (m, 1 H), 3.50-3.60 (m, 1 H), 6.88 (d, J=12.2 Hz, 1 H), 6.81 (d, J=12.4 Hz, 1 H), 7.11 (s, 1 H), 7.27-7.40 (m, 4 H), 7.48 (d, J=7.83 Hz, 2 H), 7.52-7.62 (m, 5 H); Calcd for C28H24F6O2 (M+H) 506.17, Found 506.1.

Example 23

2-{5-[2-(3,5-Bis-trifluoromethyl-phenyl)-vinyl]-4'-trifluoromethyl-biphenyl-3-yl}-4-methyl-pentanoic acid

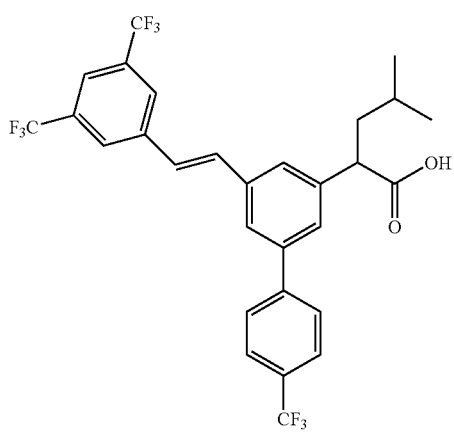 [SMILES: CC(C)CC(C(=O)O)c1cc(/C=C/c2cc(C(F)(F)F)cc(C(F)(F)F)c2)cc(-c2ccc(C(F)(F)F)cc2)c1]

The title compound was prepared from a Nigishi coupling of 4-methyl-2-(5-trifluoromethyl-biphenyl-3-yl)pentanoic acid (intermediate compound 1g) with trans-2-(3,5-bis-trifluoromethylphenyl)-vinyl-boronic acid under the conditions described in Example 14; 1H NMR (400 MHz, MeOD) δ ppm 0.98 (dd, J=6.60, 3.18 Hz, 6 H), 1.56 (dt, J=13.39, 6.63 Hz, 1 H), 1.75 (ddd, J=13.69, 7.21, 6.97 Hz, 1 H), 2.05 (ddd, J=13.57, 7.70, 7.58 Hz, 1 H), 3.82 (t, J=7.70 Hz, 1 H), 7.52 (d, J=16.5 Hz, 1 H), 7.44 (d, J=16.5 Hz, 1 H), 7.60 (s, 1 H), 7.67 (s, 1 H), 7.74-7.84 (m, 6 H), 8.18 (s, 2 H); Calcd for C29H23F9O2 (M+H) 575.16, Found 575.1.

Example 24

2-[5-(2-Biphenyl-4-yl-ethyl)-4'-trifluoromethyl-biphenyl-3-yl]-4-methyl-pentanoic acid

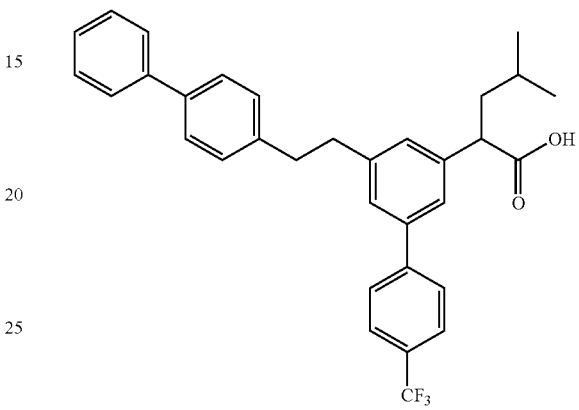

A mixture of compound 14 (20 mg, 0.039 mmole), 10% Pd/C (10 mg), and MeOH (5 mL) was hydrogenated under H$_2$ (40 psi) in par-shaker for 20 h. The resulting reaction mixture was filtered through a celite pad and concentrated to give the title compound (19 mg, 98%) as a white solid; ¹H NMR (300 MHz, MeOD) δ 0.83-0.92 (m, 6 H), 1.46 (ddd, J=13.38, 6.59, 6.41 Hz, 1 H), 1.63 (ddd, J=13.75, 7.16, 6.97 Hz, 1 H), 1.87-1.98 (m, 1 H), 2.94-3.07 (m, 4 H), 3.68 (t, J=7.72 Hz, 1 H), 7.15-7.23 (m, 3 H), 7.25-7.33 (m, 2 H), 7.36-7.44 (m, 3 H), 7.50 (d, J=8.29 Hz, 2 H), 7.57 (d, J=7.54 Hz, 2H), 7.64-7.71 (m, 4H); Calcd for C33H31F3O2 (M+Na) 539.23, Found 539.2.

Example 25

4-Methyl-2-{4'-trifluoromethyl-5-[2-(4-trifluoromethyl-phenyl)-ethyl]-biphenyl-3-yl}-pentanoic acid

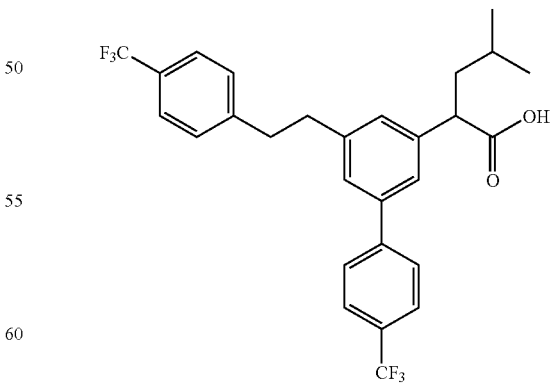

The title compound was prepared from hydrogenation of compound 15 under the conditions described in Example 24; 1H NMR (400 MHz, MeOD) δ ppm 0.83 (d, J=6.60 Hz, 6 H), 1.39-1.50 (m, 2 H), 1.81-1.89 (m, 1 H), 2.89-2.98 (m, 4 H), 3.52 (t, J=7.58 Hz, 1 H), 7.11-7.15 (m, 2 H), 7.26 (d, J=8.07 Hz, 2 H), 7.40-7.47 (m, 3 H), 7.57-7.65 (m, 4 H); Calcd for C28H26F6O2 (M+Na) 531.18, Found 531.2.

Example 26

2-{5-[2-(4-Chloro-phenyl)-ethyl]-4'-trifluoromethyl-biphenyl-3-yl}-4-methyl-pentanoic acid

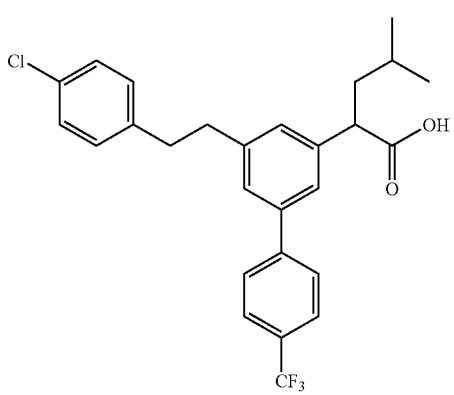 [SMILES: CC(C)CC(C(=O)O)c1cc(CCc2ccc(Cl)cc2)cc(-c2ccc(C(F)(F)F)cc2)c1]

The title compound was prepared from hydrogenation of compound 17 under the conditions described in Example 24; 1H NMR (400 MHz, MeOD) δ ppm 0.95 (dd, J=6.60, 1.71 Hz, 6 H), 1.46-1.53 (m, 1 H), 1.62-1.69 (m, 1 H), 1.91-1.99 (m, 1 H), 2.95-3.04 (m, 4 H), 3.70 (t, J=7.70 Hz, 1 H), 7.15-7.20 (m, 3 H), 7.23-7.28 (m, 2 H), 7.33 (d, J=1.47 Hz, 1 H), 7.44 (d, J=1.71 Hz, 1 H), 7.74 (s, 4 H).

Example 27

2-{5-[2-(4-Fluoro-phenyl)-ethyl]-4'-trifluoromethyl-biphenyl-3-yl}-4-methyl-pentanoic acid

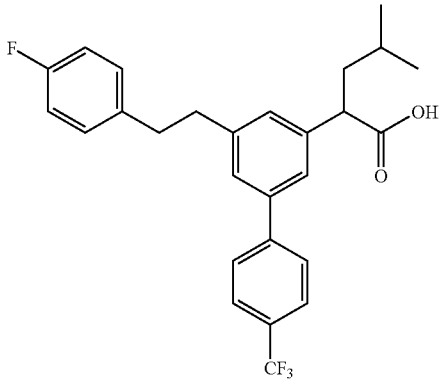 [SMILES: CC(C)CC(C(=O)O)c1cc(CCc2ccc(F)cc2)cc(-c2ccc(C(F)(F)F)cc2)c1]

The title compound was prepared from hydrogenation of compound 18 under the conditions described in Example 24; 1H NMR (400 MHz, MeOD) δ ppm 0.95 (d, J=6.60 Hz, 6 H), 1.40-1.50 (m, 1 H), 1.60-1.70 (m, 1 H), 1.89-2.02 (m, 1 H), 2.90-3.02 (m, 4 H), 3.69 (t, J=7.5 Hz, 1 H), 6.95-7.00 (m, 2 H), 7.10-7.18 (m, 3 H), 7.36 (s, 1 H), 7.44 (s, 1 H), 7.73-7.78 (m, 4 H).

Example 28

4-Methyl-2-[5-(2-p-tolyl-ethyl)-4'-trifluoromethyl-biphenyl-3-yl]-pentanoic acid

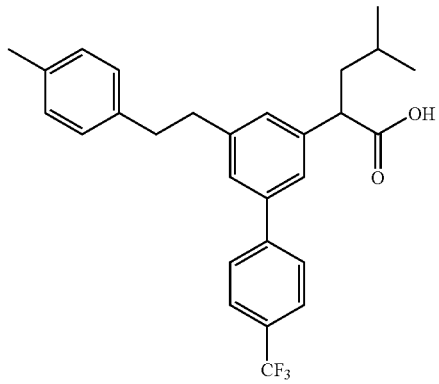 [SMILES: Cc1ccc(CCc2cc(-c3ccc(C(F)(F)F)cc3)cc(C(CC(C)C)C(=O)O)c2)cc1]

The title compound was prepared from hydrogenation of compound 16 under the conditions described in Example 24; 1H NMR (400 MHz, MeOD) δ ppm 0.83 (dd, J=6.60, 1.71 Hz, 6 H), 1.33-1.41 (m, 1 H), 1.53 (ddd, J=13.82, 7.09, 6.97 Hz, 1 H), 1.83 (dt, J=13.63, 7.61 Hz, 1 H), 2.19 (s, 3 H), 2.78-2.90 (m, 4 H), 3.58 (t, J=7.70 Hz, 1 H), 6.91-6.97 (m, 4 H), 7.03 (d, J=1.71 Hz, 1 H), 7.19 (d, J=1.47 Hz, 1 H), 7.32 (d, J=1.71 Hz, 1 H), 7.62 (s, 4 H).

Example 29

2-{5-[2-(3,5-Difluoro-phenyl)-ethyl]-4'-trifluoromethyl-biphenyl-3-yl}-4-methyl-pentanoic acid

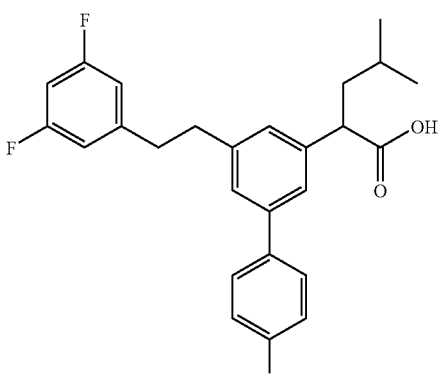

The title compound was prepared from hydrogenation of compound 19 under the conditions described in Example 24; 1H NMR (400 MHz, MeOD) δ ppm 0.83 (dd, J=6.60, 1.96 Hz, 6 H), 1.36 (ddd, J=13.33, 6.85, 6.72 Hz, 1 H), 1.50-1.59 (m, 1 H), 1.79-1.87 (m, 1 H), 2.87-2.90 (m, 4 H), 3.59 (t, J=7.83 Hz, 1 H), 6.62-6.70 (m, 3 H), 7.05 (s, 1 H), 7.28 (d, J=1.47 Hz, 1 H), 7.35 (d, J=1.47 Hz, 1 H), 7.61-7.68 (m, 4 H); Calcd for C27H25F5O2 (M+Na) 499.18, Found 499.2.

Screening of the Compounds of the Invention for γ-Secretase-Modulating Activity

Screening was carried out using SKNBE2 cells carrying the APP 695-wild type, grown in DMEM/NUT-mix F12 (HAM) provided by Gibco (cat no. 31330-38) containing 5% Serum/Fe supplemented with 1% non-essential amino acids. Cells were grown to near confluency.

The screening was performed using the assay as described in Citron et al (1997) Nature Medicine 3: 67.

Examples of the γ-secretase modulating activity of representative products of the invention are shown in the following table.

| Compound # | Structure | Chemical Name | Aβ 42 lowering EC50 (uM) | Aβ % inhibition @ 1 uM |
|---|---|---|---|---|
| 1 | 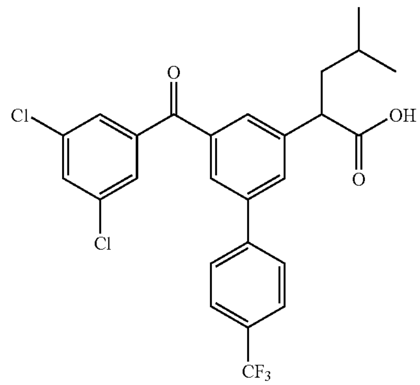 [SMILES: CC(C)CC(C(=O)O)c1cc(C(=O)c2cc(Cl)cc(Cl)c2)cc(-c2ccc(C(F)(F)F)cc2)c1] | 2-[5-(3,5-Dichloro-benzoyl)-4'-trifluoromethyl-biphenyl-3-yl]-4-methyl-pentanoic acid | 0.71 | |
| 2 | 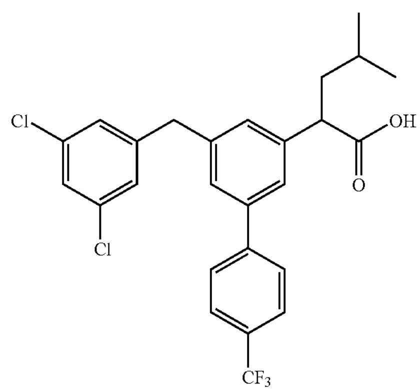 [SMILES: CC(C)CC(C(=O)O)c1cc(Cc2cc(Cl)cc(Cl)c2)cc(-c2ccc(C(F)(F)F)cc2)c1] | 2-[5-(3,5-Dichloro-benzyl)-4'-trifluoromethyl-biphenyl-3-yl]-4-methyl-pentanoic acid | 0.57 | |
| 3 | 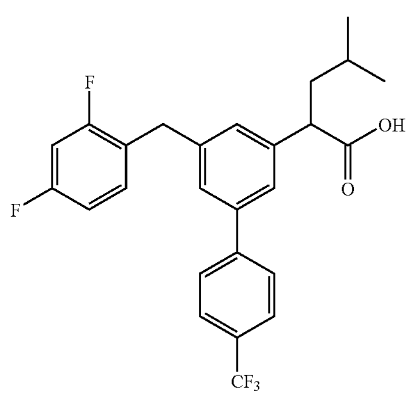 [SMILES: CC(C)CC(C(=O)O)c1cc(Cc2ccc(F)cc2F)cc(-c2ccc(C(F)(F)F)cc2)c1] | 2-[5-(2,4-Difluoro-benzyl)-4'-trifluoromethyl-biphenyl-3-yl]-4-methyl-pentanoic acid | 2.17 | |

-continued

| Compound # | Structure | Chemical Name | Aβ 42 lowering EC50 (uM) | Aβ % inhibition @ 1 uM |
|---|---|---|---|---|
| 4 | 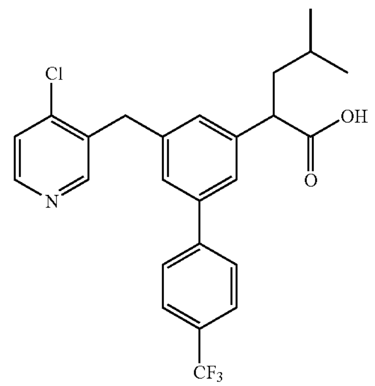 [SMILES: CC(C)CC(C(=O)O)c1cc(Cc2cnccc2Cl)cc(-c2ccc(C(F)(F)F)cc2)c1] | 2-[5-(4-Chloro-pyridin-3-ylmethyl)-4'-trifluoromethyl-biphenyl-3-yl]-4-methyl-pentanoic acid | 2.75 | |
| 5 | 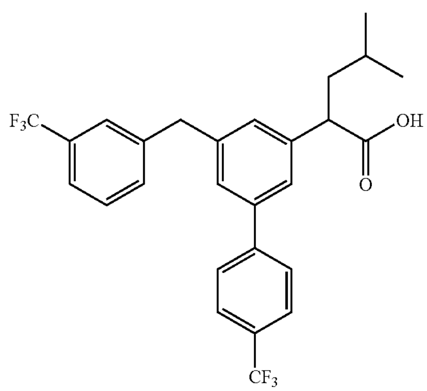 [SMILES: CC(C)CC(C(=O)O)c1cc(Cc2cccc(C(F)(F)F)c2)cc(-c2ccc(C(F)(F)F)cc2)c1] | 4-Methyl-2-[4'-trifluoromethyl-5-(3-trifluoromethyl-benzyl)-biphenyl-3-yl]-pentanoic acid | 1.13 | |
| 6 | 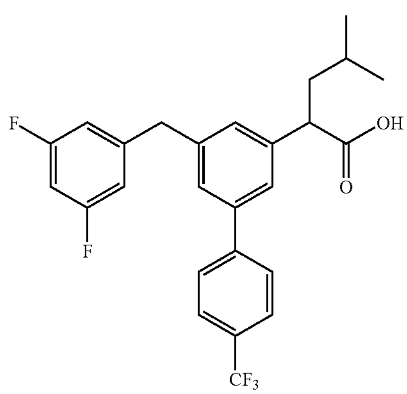 [SMILES: CC(C)CC(C(=O)O)c1cc(Cc2cc(F)cc(F)c2)cc(-c2ccc(C(F)(F)F)cc2)c1] | 2-[5-(3,5-Difluoro-benzyl)-4'-trifluoromethyl-biphenyl-3-yl]-4-methyl-pentanoic acid | 0.74 | |
| 7 | 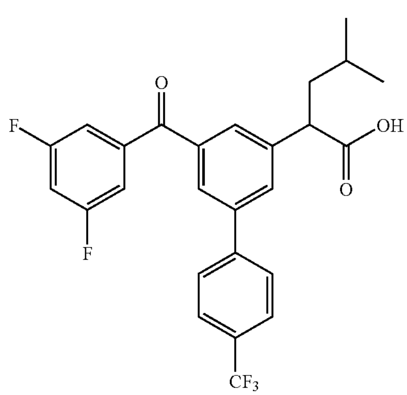 [SMILES: CC(C)CC(C(=O)O)c1cc(C(=O)c2cc(F)cc(F)c2)cc(-c2ccc(C(F)(F)F)cc2)c1] | 2-[5-(3,5-Difluoro-benzoyl)-4'-trifluoromethyl-biphenyl-3-yl]-4-methyl-pentanoic acid | | 50 |

-continued
| Compound # | Structure | Chemical Name | Aβ 42 lowering EC50 (uM) | Aβ % inhibition @ 1 uM |
|---|---|---|---|---|
| 8 | 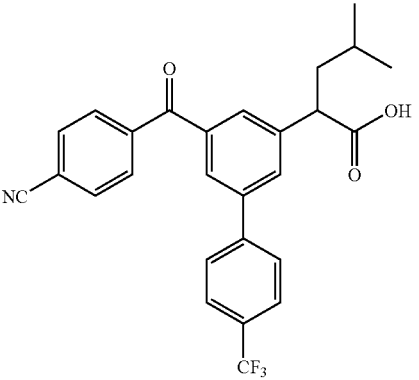 | 2-[5-(4-Cyano-benzoyl)-4'-trifluoromethyl-biphenyl-3-yl]-4-methyl-pentanoic acid | | 25 |
| 9 | 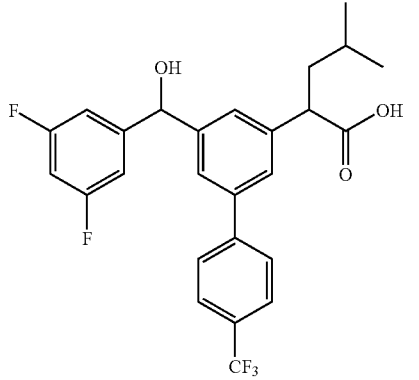 [SMILES: CC(C)CC(C(=O)O)c1cc(-c2ccc(C(F)(F)F)cc2)cc(C(O)c2cc(F)cc(F)c2)c1] | 2-{5-[(3,5-Difluoro-phenyl)-hydroxy-methyl]-4'-trifluoromethyl-biphenyl-3-yl}-4-methyl-pentanoic acid | | 14 |
| 10 | 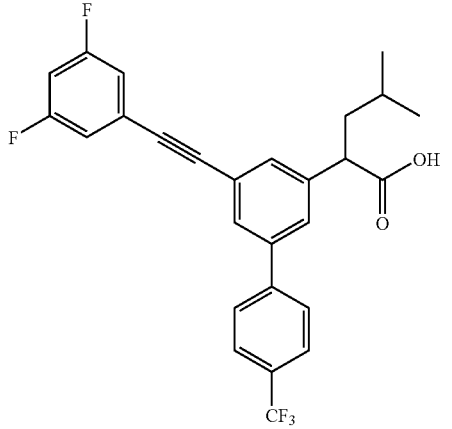 [SMILES: CC(C)CC(C(=O)O)c1cc(C#Cc2cc(F)cc(F)c2)cc(-c2ccc(C(F)(F)F)cc2)c1] | 2-[5-(3,5-Difluoro-phenylethynyl)-4'-trifluoromethyl-biphenyl-3-yl]-4-methyl-pentanoic acid | | 53 |

| Compound # | Structure | Chemical Name | Aβ 42 lowering EC50 (uM) | Aβ % inhibition @ 1 uM |
|---|---|---|---|---|
| 11 | 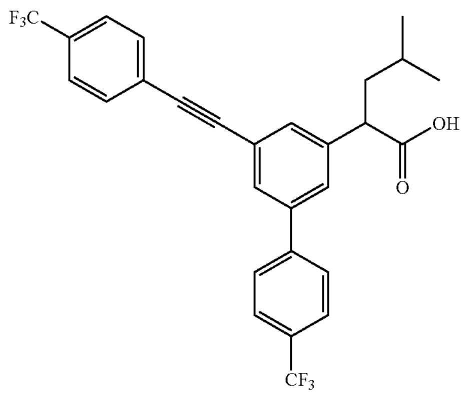 [SMILES: CC(C)CC(C(=O)O)c1cc(C#Cc2ccc(C(F)(F)F)cc2)cc(-c2ccc(C(F)(F)F)cc2)c1] | 4-Methyl-2-[4'-trifluoromethyl-5-(4-trifluoromethyl-phenylethynyl)-biphenyl-3-yl]-pentanoic acid | | 10 |
| 12 | 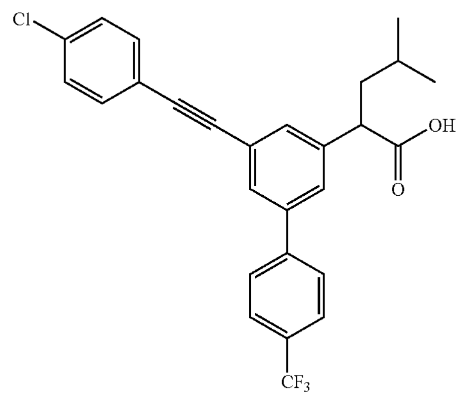 [SMILES: CC(C)CC(C(=O)O)c1cc(C#Cc2ccc(Cl)cc2)cc(-c2ccc(C(F)(F)F)cc2)c1] | 2-[5-(4-Chloro-phenylethynyl)-4'-trifluoromethyl-biphenyl-3-yl]-4-methyl-pentanoic acid | | 18 |
| 13 | 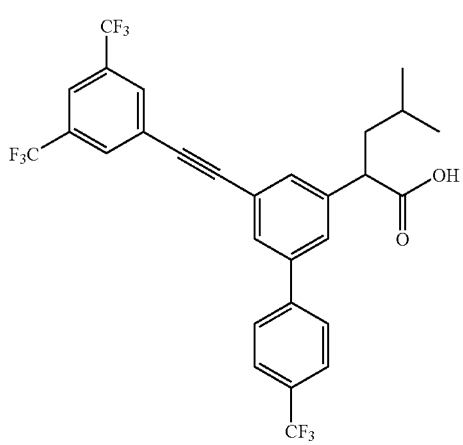 [SMILES: CC(C)CC(C(=O)O)c1cc(C#Cc2cc(C(F)(F)F)cc(C(F)(F)F)c2)cc(-c2ccc(C(F)(F)F)cc2)c1] | 2-[5-(3,5-Bis-trifluoromethyl-phenylethynyl)-4'-trifluoromethyl-biphenyl-3-yl]-4-methyl-pentanoic acid | | 28 |

-continued

| Compound # | Structure | Chemical Name | Aβ 42 lowering EC50 (uM) | Aβ % inhibition @ 1 uM |
|---|---|---|---|---|
| 14 | 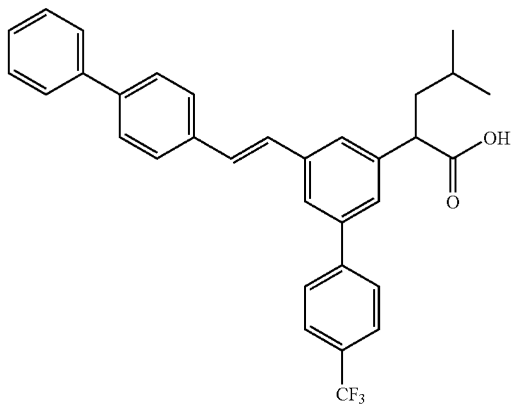 [SMILES: CC(C)CC(C(=O)O)c1cc(/C=C/c2ccc(-c3ccccc3)cc2)cc(-c2ccc(C(F)(F)F)cc2)c1] | 2-[5-(2-Biphenyl-4-yl-vinyl)-4'-trifluoromethyl-biphenyl-3-yl]-4-methyl-pentanoic acid | 0.15 | |
| 15 | 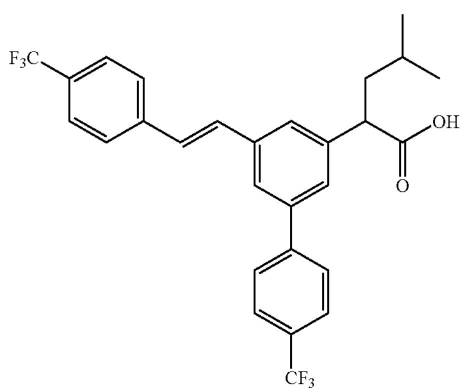 [SMILES: CC(C)CC(C(=O)O)c1cc(/C=C/c2ccc(C(F)(F)F)cc2)cc(-c2ccc(C(F)(F)F)cc2)c1] | 4-Methyl-2-{4'-trifluoromethyl-5-[2-(4-trifluoromethyl-phenyl)-vinyl]-biphenyl-3-yl}-pentanoic acid | 0.4 | |
| 16 | 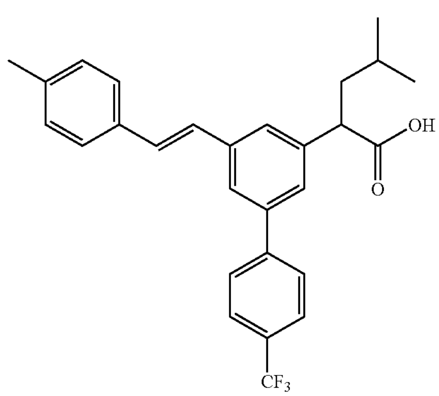 | 4-Methyl-2-[5-(2-p-tolyl-vinyl)-4'-trifluoromethyl-biphenyl-3-yl]-pentanoic acid | 0.66 | |

-continued
| Compound # | Structure | Chemical Name | Aβ 42 lowering EC50 (uM) | Aβ % inhibition @ 1 uM |
|---|---|---|---|---|
| 17 | 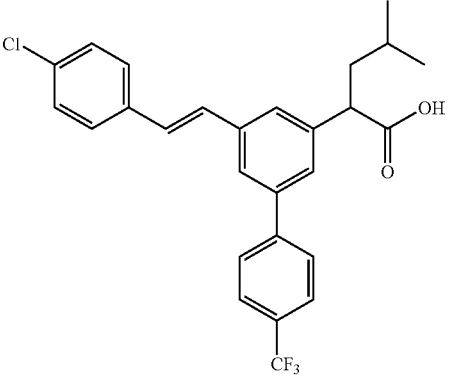 | 2-{5-[2-(4-Chloro-phenyl)-vinyl]-4'-trifluoromethyl-biphenyl-3-yl}-4-methyl-pentanoic acid | 0.36 | |
| 18 | 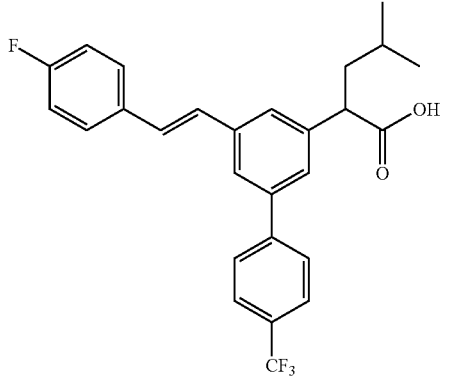 [SMILES: CC(C)CC(C(=O)O)c1cc(/C=C/c2ccc(F)cc2)cc(-c2ccc(C(F)(F)F)cc2)c1] | 2-{5-[2-(4-Fluoro-phenyl)-vinyl]-4'-trifluoromethyl-biphenyl-3-yl}-4-methyl-pentanoic acid | 0.39 | |
| 19 | 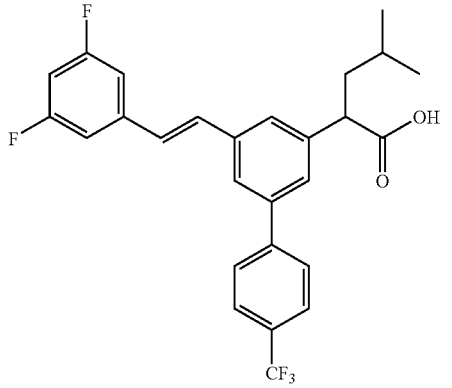 [SMILES: CC(C)CC(C(=O)O)c1cc(/C=C/c2cc(F)cc(F)c2)cc(-c2ccc(C(F)(F)F)cc2)c1] | 2-{5-[2-(3,5-Difluoro-phenyl)-vinyl]-4'-trifluoromethyl-biphenyl-3-yl}-4-methyl-pentanoic acid | 0.45 | |

-continued

| Compound # | Structure | Chemical Name | Aβ 42 lowering EC50 (uM) | Aβ % inhibition @ 1 uM |
|---|---|---|---|---|
| 20 | 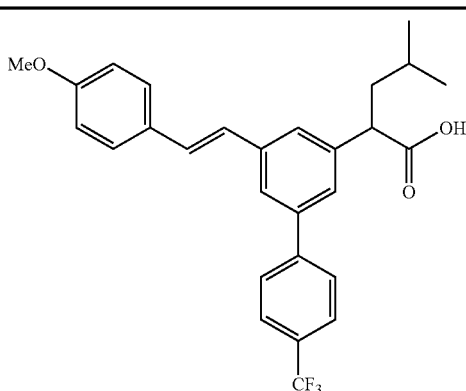 | 2-{5-[2-(4-Methoxy-phenyl)-vinyl]-4'-trifluoromethyl-biphenyl-3-yl}-4-methyl-pentanoic acid | 0.61 | |
| 21 | 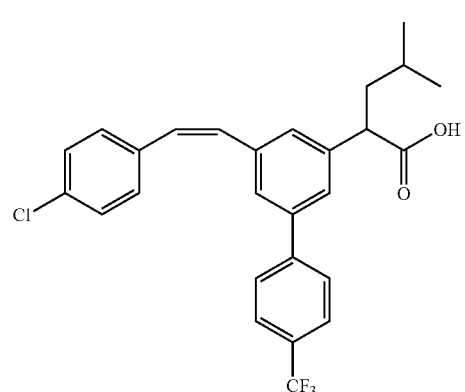 | 2-{5-[2-(4-Chloro-phenyl)-vinyl]-4'-trifluoromethyl-biphenyl-3-yl}-4-methyl-pentanoic acid | | 34 |
| 22 | 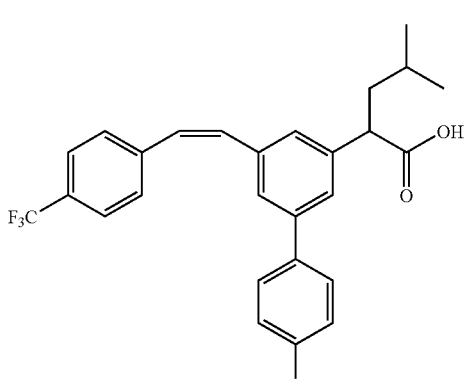 | 4-Methyl-2-{4'-trifluoromethyl-5-[2-(4-trifluoromethyl-phenyl)-vinyl]-biphenyl-3-yl}-pentanoic acid | | 46 |
| 23 | 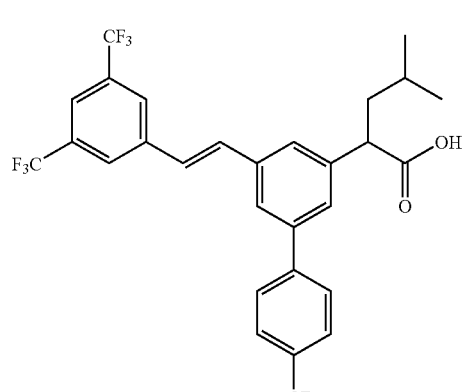 | 2-{5-[2-(3,5-Bis-trifluoromethyl-phenyl)-vinyl]-4'-trifluoromethyl-biphenyl-3-yl}-4-methyl-pentanoic acid | | 72 |

-continued

| Compound # | Structure | Chemical Name | Aβ 42 lowering EC50 (uM) | Aβ % inhibition @ 1 uM |
|---|---|---|---|---|
| 24 | 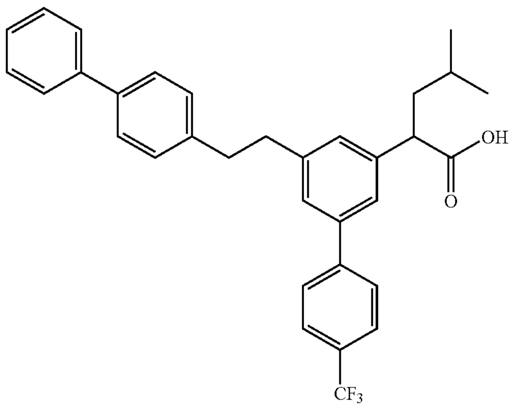 | 2-[5-(2-Biphenyl-4-yl-ethyl)-4'-trifluoromethyl-biphenyl-3-yl]-4-methyl-pentanoic acid | 0.21 | |
| 25 | 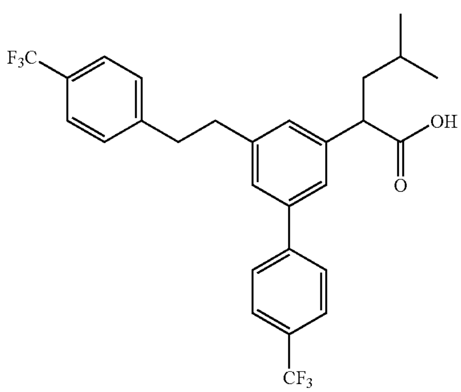 | 4-Methyl-2-{4'-trifluoromethyl-5-[2-(4-trifluoromethyl-phenyl)-ethyl]-biphenyl-3-yl}-pentanoic acid | 0.67 | |
| 26 | 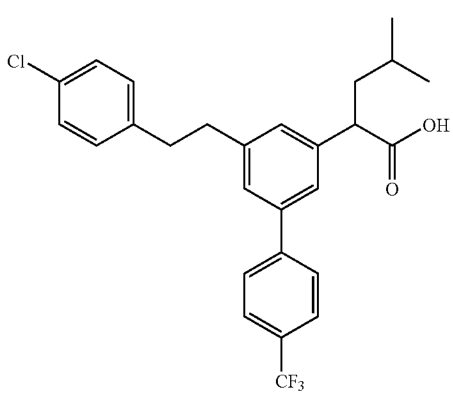 | 2-{5-[2-(4-Chloro-phenyl)-ethyl]-4'-trifluoromethyl-biphenyl-3-yl}-4-methyl-pentanoic acid | 0.74 | |

-continued

| Compound # | Structure | Chemical Name | Aβ 42 lowering EC50 (uM) | Aβ % inhibition @ 1 uM |
|---|---|---|---|---|
| 27 | 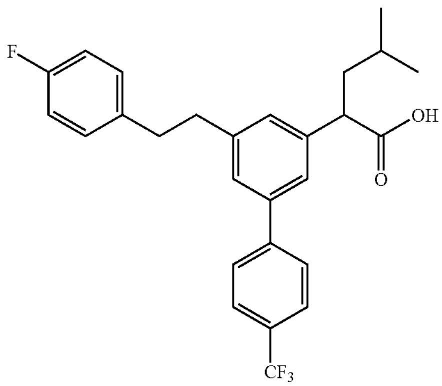 [SMILES: CC(C)CC(C(=O)O)c1cc(CCc2ccc(F)cc2)cc(-c2ccc(C(F)(F)F)cc2)c1] | 2-{5-[2-(4-Fluoro-phenyl)-ethyl]-4'-trifluoromethyl-biphenyl-3-yl}-4-methyl-pentanoic acid | 0.58 | |
| 28 | 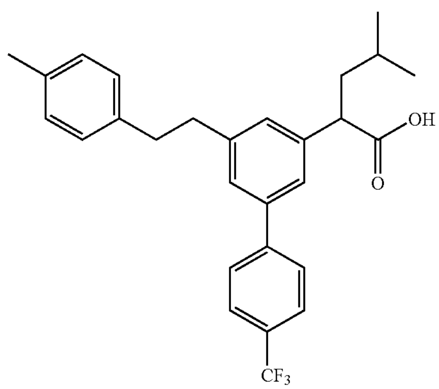 [SMILES: Cc1ccc(CCc2cc(-c3ccc(C(F)(F)F)cc3)cc(C(CC(C)C)C(=O)O)c2)cc1] | 4-Methyl-2-[5-(2-p-tolyl-ethyl)-4'-trifluoromethyl-biphenyl-3-yl]-pentanoic acid | 0.35 | |
| 29 | 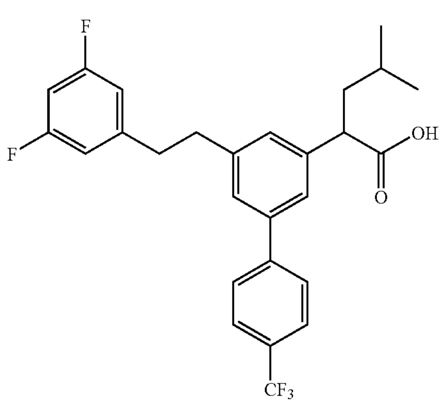 [SMILES: CC(C)CC(C(=O)O)c1cc(CCc2cc(F)cc(F)c2)cc(-c2ccc(C(F)(F)F)cc2)c1] | 2-{5-[2-(3,5-Difluoro-phenyl)-ethyl]-4'-trifluoromethyl-biphenyl-3-yl}-4-methyl-pentanoic acid | 0.41 | |

We claim:
1. A compound having the general Formula (I)

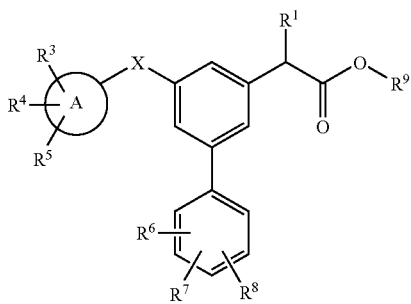

wherein
A is phenyl or pyridyl; and,
(A)
X is C(O) or C≡C;
R$^1$ is selected from the group consisting of H, F, alkyl selected from the group consisting of CH$_3$, C$_2$H$_5$, i-C$_3$H$_7$, n-C$_3$H$_7$, i-C$_4$H$_9$, n-C$_4$H$_9$, sec-C$_4$H$_9$, and tert-C$_4$H$_9$, and, alkenyl selected from C$_2$H$_3$, i-C$_3$H$_5$, n-C$_3$H$_5$, n-C$_4$H$_7$, i-C$_4$H$_7$, sec-C$_4$H$_7$; wherein said alkyl and alkenyl groups are optionally substituted with one, two, or three substituents independently selected from the group consisting of F, Cl, Br, I and CF$_3$;
R$^3$ is OCF$_3$, F, Cl, OCH$_3$, C$_{(1-4)}$alkyl, phenyl, or CN;
R$^6$ is selected from the group consisting of H, F, Cl, Br, I, CN, OH, C(O)N(C$_{(1-4)}$alkyl)$_2$, S(O)$_2$C$_{(1-4)}$alkyl, SO$_2$N(C$_{(1-4)}$alkyl)$_2$, S(O)N(C$_{(1-4)}$alkyl)$_2$, N(C$_{(1-4)}$alkyl)S(O)$_2$C$_{(1-4)}$alkyl, N(C$_{(1-4)}$alkyl)S(O)C$_{(1-4)}$alkyl, S(O)$_2$C$_{(1-4)}$alkyl, N(C$_{(1-4)}$alkyl)S(O)$_2$N(C$_{(1-4)}$alkyl)$_2$, SC$_{(1-4)}$alkyl, N(C$_{(1-4)}$alkyl)$_2$, N(C$_{(1-4)}$alkyl)C(O)C$_{(1-4)}$alkyl, N(C$_{(1-4)}$alkyl)C(O)N(C$_{(1-4)}$alkyl)$_2$, N(C$_{(1-4)}$alkyl)C(O)OC$_{(1-4)}$alkyl, OC(O) N(C$_{(1-4)}$alkyl)$_2$, C(O)C$_{(1-4)}$alkyl, C$_1$-C$_4$-alkyl, and C$_1$-C$_4$-alkoxy; wherein said alkyl and alkoxy are optionally substituted with one, two, or three substituents selected from the group consisting of F, Cl, Br, and I;
R$^4$ is selected from the group consisting of H, F, Cl, OCH$_3$, C$_{(1-4)}$alkyl, and CN;
R$^5$ is selected from the group consisting of H, F, Cl, OCH$_3$, C$_{(1-4)}$alkyl, and CN;
R$^7$ is selected from the group consisting of CF$_3$, H, F, Cl, OCH$_3$, C$_{(1-4)}$alkyl, and CN;
R$^8$ is selected from the group consisting of CF$_3$, H, F, Cl, OCH$_3$, C$_{(1-4)}$alkyl, and CN;
R$^9$ is selected from the group consisting of H, alkyl selected from the group CH$_3$, C$_2$H$_5$, i-C$_3$H$_7$, n-C$_3$H$_7$, i-C$_4$H$_9$, n-C$_4$H$_9$, sec-C$_4$H$_9$, tert-C$_4$H$_9$; alkenyl selected from C$_2$H$_3$, i-C$_3$H$_5$, n-C$_3$H$_5$, n-C$_4$H$_7$, i-C$_4$H$_7$, sec-C$_4$H$_7$; wherein said alkyl and alkenyl groups are optionally substituted with one, two, or three substituents independently selected from the group consisting of F, Cl, Br, I and CF$_3$;

or,
(B)
X is CH$_2$, CH$_2$CH$_2$, CH=CH, or CHOH;
R$^1$ is selected from the group consisting of H, F, alkyl selected from the group CH$_3$, C$_2$H$_5$, i-C$_3$H$_7$, n-C$_3$H$_7$, i-C$_4$H$_9$, n-C$_4$H$_9$, sec-C$_4$H$_9$, tert-C$_4$H$_9$; alkenyl selected from C$_2$H$_3$, i-C$_3$H$_5$, n-C$_3$H$_5$, n-C$_4$H$_7$, i-C$_4$H$_7$, sec-C$_4$H$_7$; wherein said alkyl and alkenyl groups are optionally substituted with one, two, or three substituents independently selected from the group consisting of F, Cl, Br, I and CF$_3$;
R$^3$ is CF$_3$, OCF$_3$, F, Cl, OCH$_3$, C$_{(1-4)}$alkyl, phenyl, or CN;
R$^6$ is selected from the group consisting of H, F, Cl, Br, I, CN, OH, C(O)N(C$_{(1-4)}$alkyl)$_2$, S(O)$_2$C$_{(1-4)}$alkyl, SO$_2$N(C$_{(1-4)}$alkyl)$_2$, S(O)N(C$_{(1-4)}$alkyl)$_2$, N(C$_{(1-4)}$alkyl)S(O)$_2$C$_{(1-4)}$alkyl, N(C$_{(1-4)}$alkyl)S(O)C$_{(1-4)}$alkyl, S(O)$_2$C$_{(1-4)}$alkyl, N(C$_{(1-4)}$alkyl)S(O)$_2$N(C$_{(1-4)}$alkyl)$_2$, SC$_{(1-4)}$alkyl, N(C$_{(1-4)}$alkyl)$_2$, N(C$_{(1-4)}$alkyl)C(O)C$_{(1-4)}$alkyl, N(C$_{(1-4)}$alkyl)C(O)N(C$_{(1-4)}$alkyl)$_2$, N(C$_{(1-4)}$alkyl)C(O)OC$_{(1-4)}$alkyl, OC(O) N(C$_{(1-4)}$alkyl)$_2$, C(O)C$_{(1-4)}$alkyl, C$_1$-C$_4$-alkyl, and C$_1$-C$_4$-alkoxy; wherein said alkyl and alkoxy are optionally substituted with one, two, or three substituents selected from the group consisting of F, Cl, Br, and I;
R$^4$ is selected from the group consisting of CF$_3$, H, F, Cl, OCH$_3$, C$_{(1-4)}$alkyl, and CN;
R$^5$ is selected from the group consisting of CF$_3$, H, F, Cl, OCH$_3$, C$_{(1-4)}$alkyl, and CN;
R$^7$ is selected from the group consisting of CF$_3$, H, F, Cl, OCH$_3$, C$_{(1-4)}$alkyl, and CN;
R$^8$ is selected from the group consisting of CF$_3$, H, F, Cl, OCH$_3$, C$_{(1-4)}$alkyl, and CN;
R$^9$ is selected from the group consisting of H, alkyl selected from the group consisting of CH$_3$, C$_2$H$_5$, i-C$_3$H$_7$, n-C$_3$H$_7$, i-C$_4$H$_9$, n-C$_4$H$_9$, sec-C$_4$H$_9$, and tert-C$_4$H$_9$, and, alkenyl selected from C$_2$H$_3$, i-C$_3$H$_5$, n-C$_3$H$_5$, n-C$_4$H$_7$, i-C$_4$H$_7$, and sec-C$_4$H$_7$; wherein said alkyl and alkenyl groups are optionally substituted with one, two, or three substituents independently selected from the group consisting of F, Cl, Br, I and CF$_3$;
or a pharmaceutically acceptable salt thereof.

2. The compound of claim 1 wherein
R$^1$ is selected from the group consisting of H, F, alkyl selected from the group CH$_3$, C$_2$H$_5$, i-C$_3$H$_7$, n-C$_3$H$_7$, i-C$_4$H$_9$, n-C$_4$H$_9$, sec-C$_4$H$_9$, and tert-C$_4$H$_9$; and alkenyl selected from C$_2$H$_3$, i-C$_3$H$_5$, n-C$_3$H$_5$, n-C$_4$H$_7$, i-C$_4$H$_7$, and sec-C$_4$H$_7$;
R$^4$, R$^5$, R$^6$, R$^7$, and R$^8$ are independently selected from the group consisting of CF$_3$, H, F, Cl, OCH$_3$, C$_{(1-4)}$alkyl, and CN;
R$^9$ is selected from the group consisting of H, CH$_3$, C$_2$H$_5$, i-C$_3$H$_7$, n-C$_3$H$_7$, i-C$_4$H$_9$, n-C$_4$H$_9$, sec-C$_4$H$_9$, and tert-C$_4$H$_9$;
or a pharmaceutically acceptable salt thereof.

3. The compound of claim 2 wherein
R$^3$ is CF$_3$, F, Cl, OCH$_3$, C$_{(1-4)}$alkyl, phenyl, or CN;
R$^4$, R$^5$, R$^6$ R$^7$, and R$^8$ are independently H, CF$_3$, Cl, or F;
or a pharmaceutically acceptable salt thereof.

4. The compound of claim 3 wherein
R$^9$ is H;
or a pharmaceutically acceptable salt thereof.

5. The compound of claim 4 wherein
R$^1$ is CH$_2$CH(CH$_3$)$_2$;
R$^4$ and R$^5$ are independently CF$_3$, Cl, F, or H;
R$^6$ is CF$_3$;
R$^7$ and R$^8$ are H;
or a pharmaceutically acceptable salt thereof.

6. A compound selected from the group consisting of:
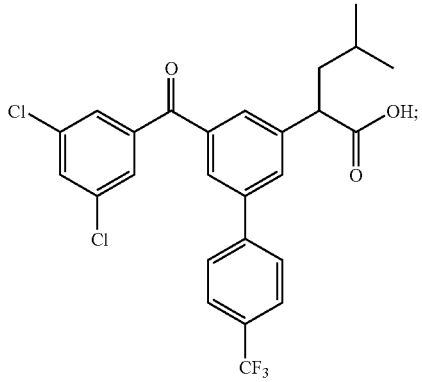
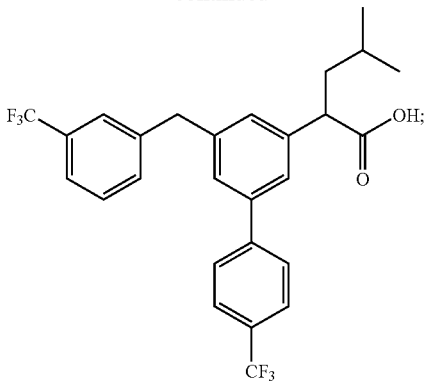
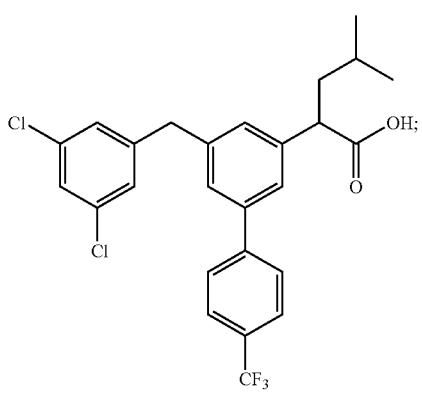
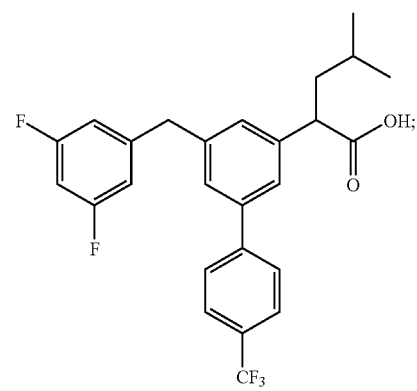
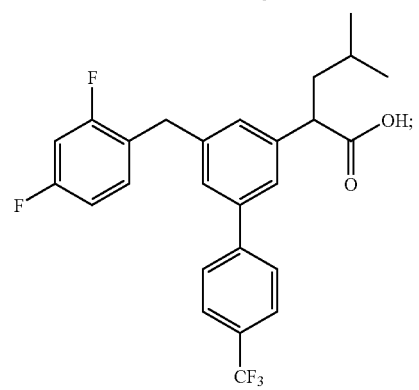
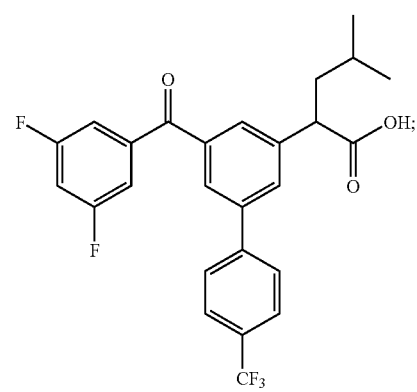
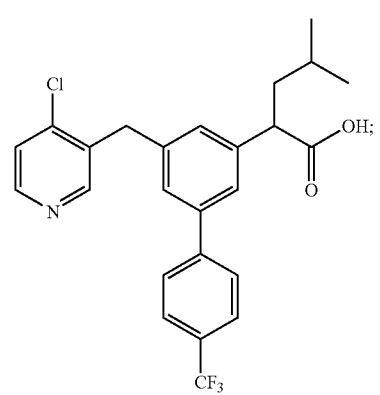
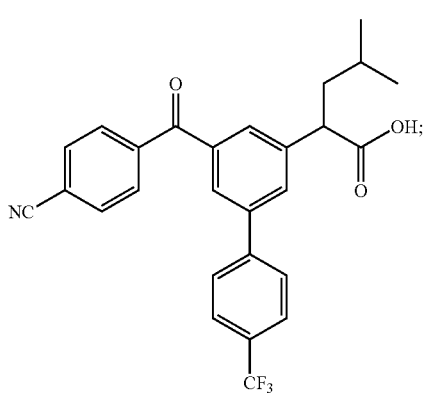

-continued
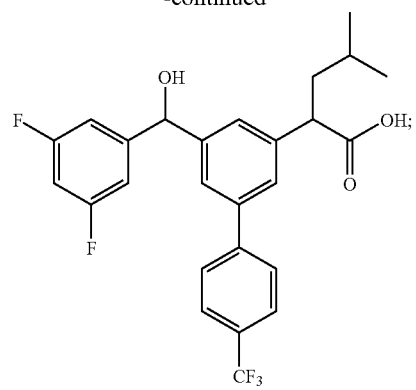
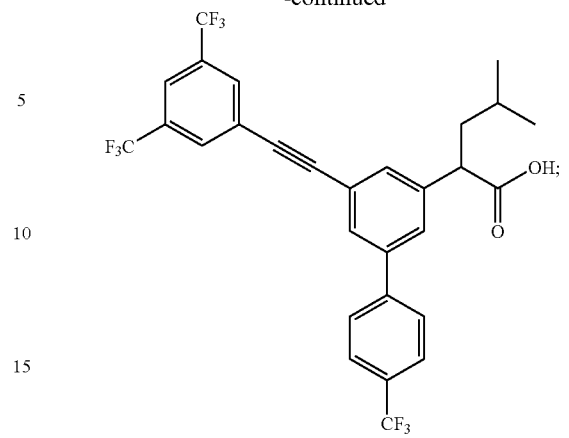
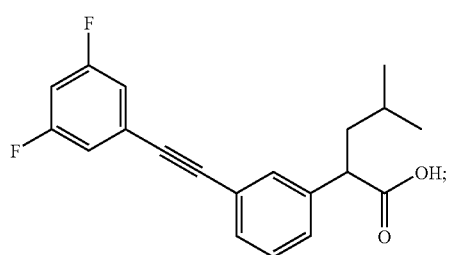
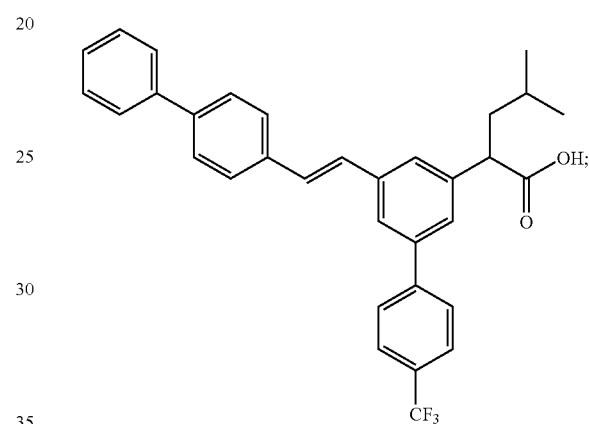
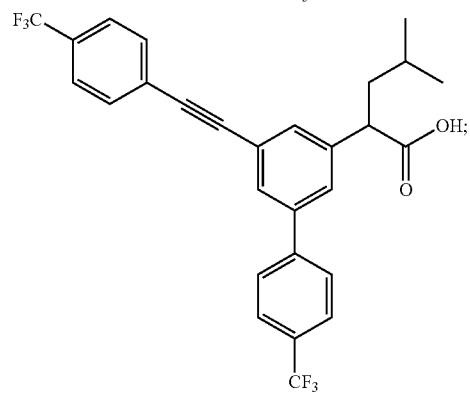
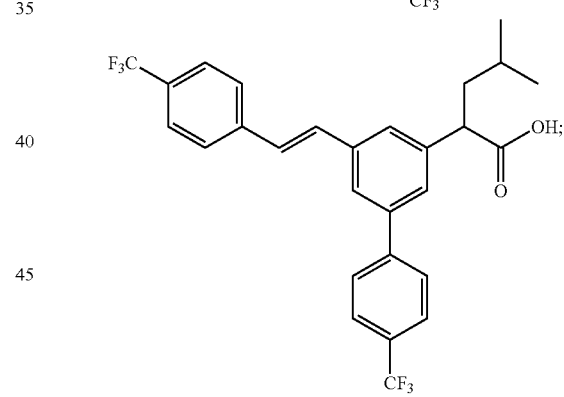
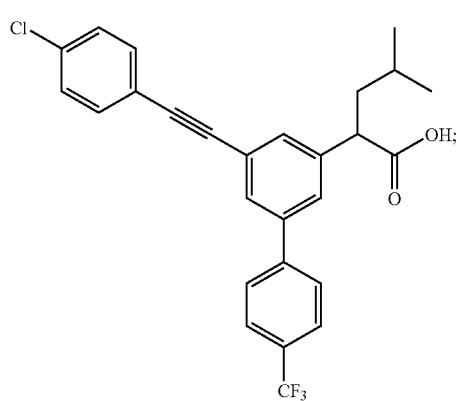
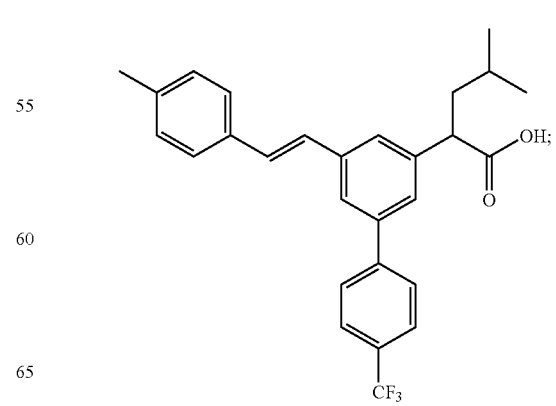

75
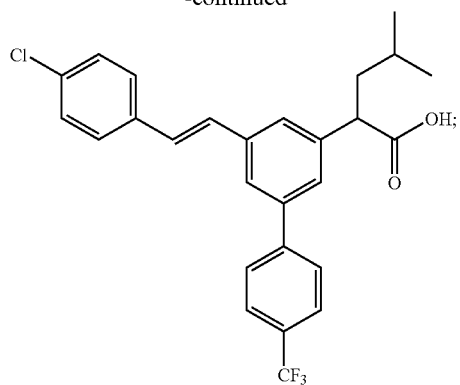
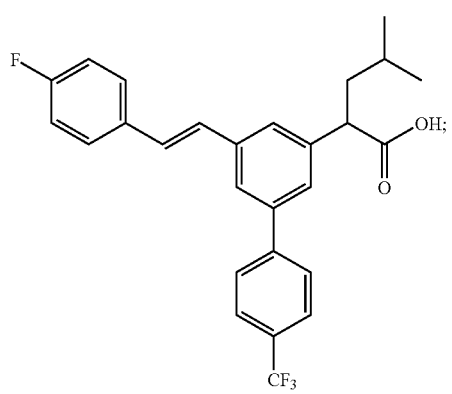
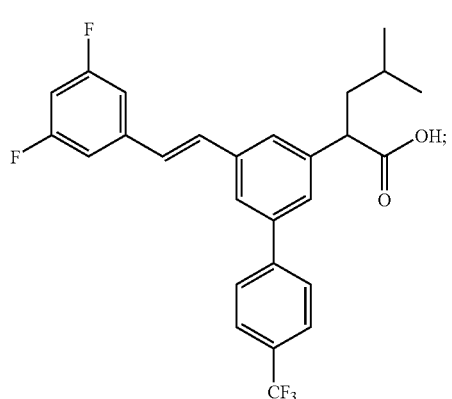
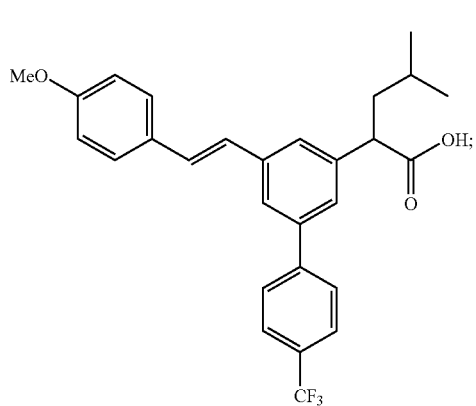
76
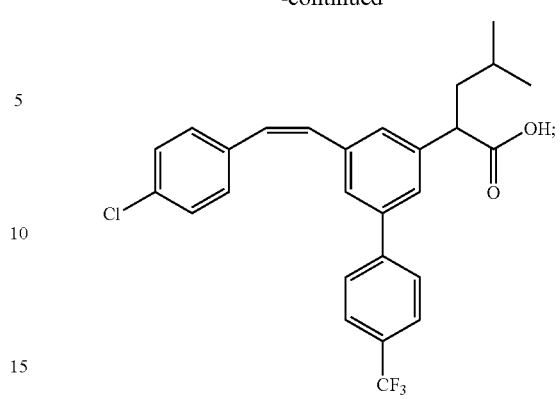
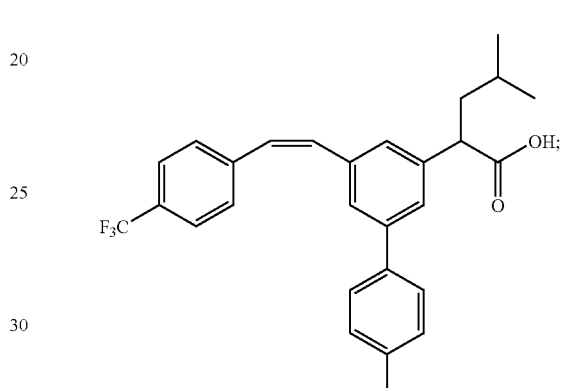
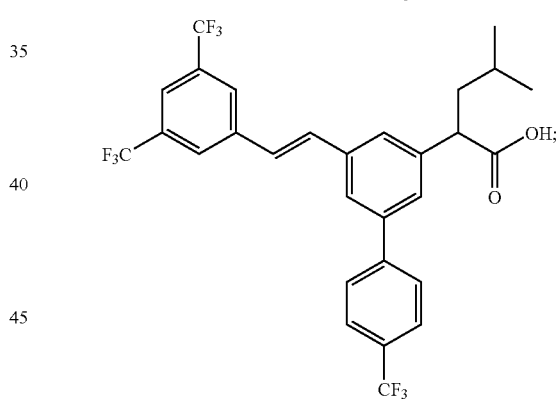
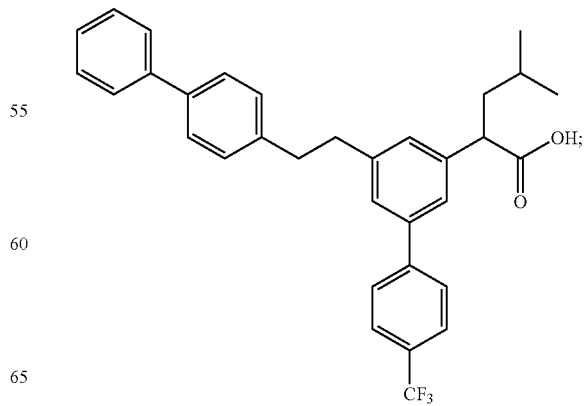

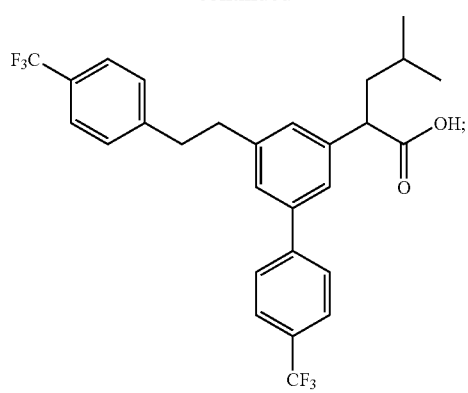

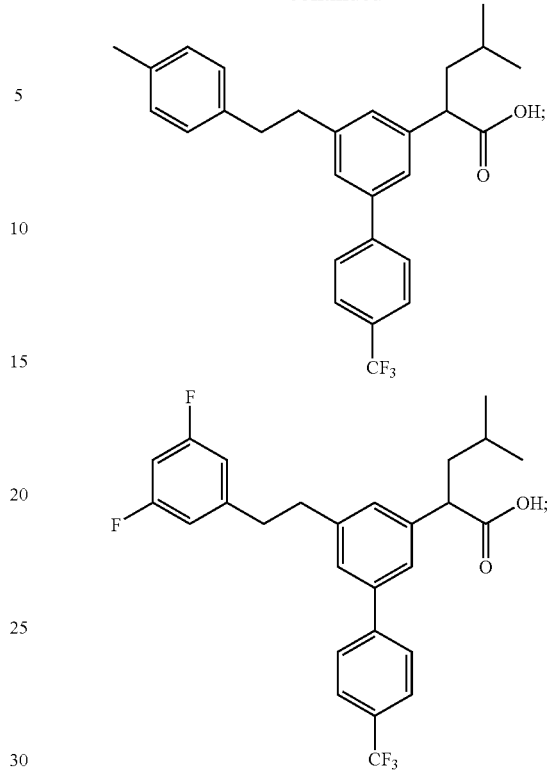

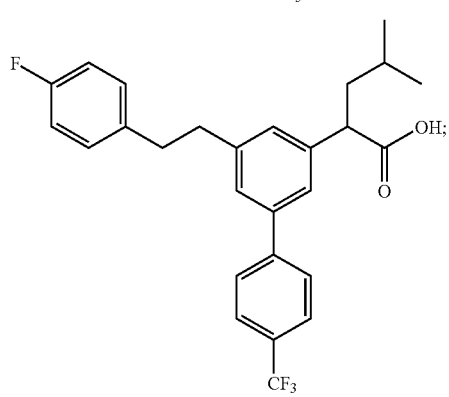

and an ester or pharmaceutically acceptable salt thereof.

7. A pharmaceutical composition comprising a compound according to any of claims 1 to 6 in admixture with an inert carrier.

8. A method of treating a mammal for the modulation of γ-secretase, wherein said method comprises administering to the mammal a therapeutically effective amount of a compound according to any of claims 1 to 6.

9. A method of treating in a mammal a disease associated with an elevated level of Aβ42-production, wherein said method comprises administering to the mammal a therapeutically effective amount of a compound according to any of claims 1 to 6.

10. The method of claim 9, wherein said disease is Alzheimer's disease.

* * * * *